United States Patent
Chytil et al.

(10) Patent No.: US 9,758,529 B2
(45) Date of Patent: Sep. 12, 2017

(54) FUSED DIHYDRO-4H-PYRAZOLO[5,1-C][1,4]OXAZINYL COMPOUNDS AND ANALOGS FOR TREATING CNS DISORDERS

(71) Applicants: Sunovion Pharmaceuticals Inc., Marlborough, MA (US); PGI Drug Discovery LLC, Tarrytown, NY (US)

(72) Inventors: Milan Chytil, Acton, MA (US); Sharon Engel, Hudson, MA (US); Taleen G. Hanania, Valhalla, NY (US); Vadim Alexandrov, Hopewell Junction, NY (US); Emer Leahy, Pound Ridge, NY (US)

(73) Assignees: Sunovion Pharmaceuticals Inc., Marlborough, MA (US); PGI Drug Discovery LLC, Tarrytown, NY (US)

( * ) Notice: Subject to any disclaimer, the term of this patent is extended or adjusted under 35 U.S.C. 154(b) by 0 days.

(21) Appl. No.: 15/041,827

(22) Filed: Feb. 11, 2016

(65) Prior Publication Data
US 2016/0264597 A1 Sep. 15, 2016

Related U.S. Application Data

(60) Provisional application No. 62/115,043, filed on Feb. 11, 2015.

(51) Int. Cl.
| | | |
|---|---|---|
| *C07D 498/04* | (2006.01) | |
| *C07D 498/14* | (2006.01) | |
| *C07D 498/20* | (2006.01) | |
| *C07D 498/22* | (2006.01) | |

(52) U.S. Cl.
CPC ......... *C07D 498/04* (2013.01); *C07D 498/14* (2013.01); *C07D 498/20* (2013.01); *C07D 498/22* (2013.01)

(58) Field of Classification Search
CPC .. C07D 498/04; C07D 498/14; C07D 498/20; C07D 498/22
See application file for complete search history.

(56) References Cited

U.S. PATENT DOCUMENTS

2012/0171199 A1* 7/2012 Dotson ............... C07D 487/14
424/133.1

FOREIGN PATENT DOCUMENTS

| JP | 2014214130 A | 11/2014 |
|---|---|---|
| WO | 2007120594 A1 | 10/2007 |
| WO | 2013067248 A1 | 5/2013 |
| WO | 2013192346 A1 | 12/2013 |

OTHER PUBLICATIONS

Lindvall et. al., Nature, 2006, Nature Publishing Group, vol. 441, pp. 1094-1096.*
Winhusen et. al., Addiction, 2005, Society for the study of addiction, vol. 100(suppl. 1), pp. 68-77.*
Korneev et. al., CAS STN Abstract, publ. 2009, RN 1202851-83-9.*
International Search Report in International Application No. PCT/US2016/017527 mailed Apr. 4, 2016.

* cited by examiner

*Primary Examiner* — Sarah Pihonak
(74) *Attorney, Agent, or Firm* — Heslin, Rothenberg, Farley & Mesiti, P.C.

(57) ABSTRACT

Disclosed are compounds of Formula (I):

and pharmaceutically acceptable salts thereof, wherein Ring B, $A^1$, $A^2$, $R^6$, w and n1 are defined and described herein; compositions thereof; and methods of use thereof. These compounds are useful for treating a variety of neurological and psychiatric disorders, such as those described herein.

54 Claims, No Drawings

FUSED DIHYDRO-4H-PYRAZOLO[5,1-C][1,4]OXAZINYL COMPOUNDS AND ANALOGS FOR TREATING CNS DISORDERS

CROSS REFERENCE TO RELATED APPLICATIONS

This application claims priority to U.S. provisional application No. 62/115,043 filed Feb. 11, 2015, which is hereby incorporated herein by reference in its entirety.

BACKGROUND

Central nervous system disorders affect a wide range of the population with differing severity. Neurological and psychiatric disorders include major depression, schizophrenia, bipolar disorder, obsessive compulsive disorder (OCD), panic disorder, and posttraumatic stress disorder (PTSD), among others. These disorders affect a person's thoughts, mood, behavior and social interactions and can significantly impair daily functioning. See, e.g., *Diagnostic and Statistical Manual of Mental Disorders*, $4^{th}$ Ed., American Psychiatric Association (2000) ("DSM-IV-TR"); *Diagnostic and Statistical Manual of Mental Disorders*, $5^{th}$ Ed., American Psychiatric Association (2013) ("DSM-5").

Bipolar disorder is a serious psychiatric disorder that has a prevalence of approximately 2% of the population, and affects both genders alike. It is a relapsing-remitting condition characterized by cycling between elevated (i.e., manic) and depressed moods, which distinguishes it from other disorders such as major depressive disorder and schizophrenia. Bipolar I is defined by the occurrence of a full manic episode, although most individuals experience significant depression. Symptoms of mania include elevated or irritable mood, hyperactivity, grandiosity, decreased need for sleep, racing thoughts and in some cases, psychosis. The depressive episodes are characterized by anhedonia, sad mood, hopelessness, poor self-esteem, diminished concentration and lethargy. Bipolar II is defined as the occurrence of a major depressive episode and hypomanic (less severe mania) episode although patients spend considerable more time in the depressive state. Other related conditions include cyclothymic disorder.

Schizophrenia is a psychopathic disorder of unknown origin, which usually appears for the first time in early adulthood and is marked by characteristics such as psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g., loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g., catatonia). Other symptoms are also associated with this disorder.

Schizophrenia is classified into subgroups: the paranoid type, characterized by delusions and hallucinations and absence of thought disorder, disorganized behavior, and affective flattening; the disorganized type, also named "hebephrenic schizophrenia," in which thought disorder and flat affect are present together; the cataconic type, in which prominent psychomotor disturbances are evident, and symptoms may include catatonic stupor and waxy flexibility; and the undifferentiated type, in which psychotic symptoms are present but the criteria for paranoid, disorganized, or catatonic types have not been met. The symptoms of schizophrenia normally manifest themselves in three broad categories: positive, negative and cognitive symptoms. Positive symptoms are those which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making.

Neurological and psychiatric disorders can exhibit a variety of symptoms, including cognitive impairment, depressive disorders, and anxiety disorders.

Cognitive impairment includes a decline in cognitive functions or cognitive domains, e.g., working memory, attention and vigilance, verbal learning and memory, visual learning and memory, reasoning and problem solving (e.g., executive function, speed of processing and/or social cognition). In particular, cognitive impairment may indicate deficits in attention, disorganized thinking, slow thinking, difficulty in understanding, poor concentration, impairment of problem solving, poor memory, difficulties in expressing thoughts, and/or difficulties in integrating thoughts, feelings and behavior, or difficulties in extinction of irrelevant thoughts.

Depressive disorders include major depressive disorder and dysthymia, and are associated with depressed mood (sadness), poor concentration, insomnia, fatigue, appetite disturbances, excessive guilt and thoughts of suicide.

Anxiety disorders are disorders characterized by fear, worry, and uneasiness, usually generalized and unfocused as an overreaction to a situation. Anxiety disorders differ in the situations or types of objects that induce fear, anxiety, or avoidance behavior, and the associated cognitive ideation. Anxiety differs from fear in that anxiety is an emotional response to a perceived future threat while fear is associated with a perceived or real immediate threat. They also differ in the content of the associated thoughts or beliefs.

SUMMARY

While medications exist for some aspects of these diseases, there remains a need for effective treatments for various neurological and psychiatric disorders, including mood disorders such as bipolar and related disorders, psychosis and schizophrenia. For example, while mood stabilizers such as lithium and valproate, antidepressants and antipsychotic drugs are used to treat mood disorders, more effective medications are necessary. And current antipsychotics may be successful in treating the positive symptoms of schizophrenia but fare less well for the negative and cognitive symptoms. Additionally, current antidepressants are typically effective only for a proportion of patients suffering from depression.

In some embodiments, the present invention encompasses the insight that compounds of Formula (I):

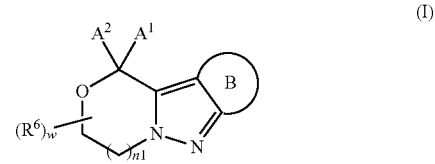

and pharmaceutically acceptable salts thereof, wherein Ring B, $A^1$, $A^2$, $R^6$, w and n1 are defined and described herein, are useful for treating a variety of neurological and psychiatric disorders, such as those described herein.

Also provided herein are methods for the treatment of various neurological and psychiatric disorders using the compounds and compositions provided herein.

DETAILED DESCRIPTION OF CERTAIN EMBODIMENTS

1. General Description of Compounds of the Invention

In some embodiments, the present invention provides a compound of Formula (I):

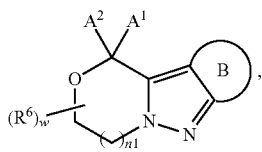

(I)

or a pharmaceutically acceptable salt thereof, wherein:
Ring B is a 6-membered aromatic ring, which ring unsubstituted or substituted with 1 to 4 substituents independently selected from halo, —OH, —$NH_2$, —$CH_3$, —$CH_2F$, —$CHF_2$ and —$CF_3$; or is a 5- or 6-membered heteroaromatic ring having 1 to 3 ring heteroatoms independently selected from O, N and S, which ring is unsubstituted or substituted with 1 to 3 substituents independently selected from halo, —OH, —$NH_2$, —$CH_3$, —$CH_2F$, —$CHF_2$ and —$CF_3$;
$A^1$ is —H or $C_{1-3}$ alkyl; and
$A^2$ is —$C(R^2)(R^8)$—$(CH_2)_p$—$N(R^9)R^{10}$;
or $A^1$ and $A^2$, together with the carbon atom to which they are attached, form

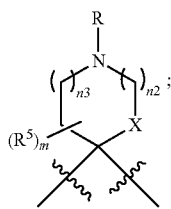

m is 0, 1 or 2;
n1 is 1 or 2;
n2 is 0 or 1;
n3 is 0 or 1;
p is 0 or 1;
R is —H or $C_1$-$C_3$ alkyl; or R is —$CH_2$—(X), —$CH_2CH_2$—(X), —$CH_2$—(Z) or —$CH_2CH_2$—(Z);
each instance of $R^5$ independently is halo, —$CH_3$ or ethyl;
each instance of $R^6$ independently is halo or —$CH_3$;
$R^7$ is —H or $C_1$-$C_3$ alkyl;
$R^8$ is —H or $C_1$-$C_3$ alkyl which is unsubstituted or substituted with $C_3$-$C_6$ cycloalkyl;
$R^9$ is —H, $C_1$-$C_4$ alkyl or $C_3$-$C_6$ cycloalkyl; and
$R^{10}$ is —H or $C_1$-$C_3$ alkyl;
or $R^9$ and $R^8$, together with the atoms to which they are attached, form (i.e., $R^9$ and $R^8$, together with the atoms to which they are attached form a ring such that —$C(R^7)(R^8)$—$(CH_2)_p$—$N(R^9)R^{10}$ is)

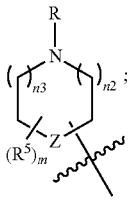

or $R^9$ and $R^{10}$, together with the nitrogen atom to which they are attached, form

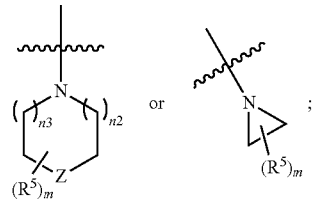

w is 0, 1 or 2;
X is CH or $CH_2$; and
Z is CH, $CH_2$ or O.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in M. Loudon, Organic Chemistry, 5th Ed., Roberts and Company, Greenwood Village, Colo.: 2009; and M. B. Smith, March's Advanced Organic Chemistry: Reactions, Mechanisms and Structure, 7th Ed., John Wiley & Sons, Hoboken: 2013, the entire contents of which are hereby incorporated by reference.

As used herein, the term "halogen" or "halo" means F, Cl, Br, or I.

As used herein, the term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

As used herein, the terms "heteroaryl" and "heteroar-," used alone or as part of a larger moiety, e.g., "heteroaralkyl," or "heteroaralkoxy," refer to groups having 5 to 10 ring atoms, preferably 5, 6, 9 or 10 ring atoms; having 6, 10, or 14π electrons shared in a cyclic array; and having, in addition to carbon atoms, from one to five ring heteroatoms. Heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. A heteroaryl group may be monocyclic or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7- to 10-membered bicyclic heterocyclic moiety that is either saturated or partially unsaturated, and having, in addition to ring carbon atoms, one to four ring heteroatoms. When used in reference to a ring atom of a heterocycle, the term "nitrogen" includes a substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein. A heterocyclyl group may be monocyclic or bicyclic. The term "heterocyclylalkyl" refers to an alkyl group substituted by a heterocyclyl, wherein the alkyl and heterocyclyl portions independently are optionally substituted.

As used herein, the term "unsaturated," as used herein, means that a moiety has one or more units of unsaturation.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein, the term "heteroatom" means one or more of oxygen, sulfur, nitrogen, phosphorus, or silicon (including, any oxidized form of nitrogen, sulfur, phosphorus, boron, or silicon; the quaternized form of any basic nitrogen or; a substitutable nitrogen of a heterocyclic ring, for example N (as in 3,4-dihydro-2H-pyrrolyl), NH (as in pyrrolidinyl) or $^+$NR (as in N-substituted pyrrolidinyl)).

As used herein, the term "aryl" used alone or as part of a larger moiety as in "aralkyl," "aralkoxy," or "aryloxyalkyl," refers to carbocyclic aromatic ring systems having a total of six to fourteen ring atoms. The term "aryl" may be used interchangeably with the term "aryl ring." Examples of "aryl" groups include phenyl, naphthyl, anthracyl and the like, which may be optionally substituted.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Unless otherwise specified, the word "includes" (or any variation thereon, e.g., "include", "including", etc.) is intended to be open-ended. For example, "A includes 1, 2 and 3" means that A includes but is not limited to 1, 2 and 3.

Unless otherwise specified, the phrase "such as" is intended to be open-ended. For example, "A can be a halogen, such as chlorine or bromine" means that A can be, but is not limited to, chlorine or bromine.

3. Description of Exemplary Embodiments

In some embodiments, the present invention provides a compound of Formula (I):

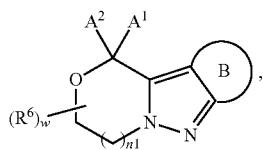

(I)

or a pharmaceutically acceptable salt thereof, wherein:

Ring B is a 6-membered aromatic ring, which ring is unsubstituted or substituted with 1 to 4 substituents independently selected from halo, —OH, —NH$_2$, —CH$_3$, —CH$_2$F, —CHF$_2$ and —CF$_3$; or is a 5- or 6-membered heteroaromatic ring having 1 to 3 ring heteroatoms independently selected from O, N and S, which ring is unsubstituted or substituted with 1 to 3 substituents independently selected from halo, —OH, —NH$_2$, —CH$_3$, —CH$_2$F, —CHF$_2$ and —CF$_3$;

A$^1$ is —H or C$_{1-3}$ alkyl; and

A$^2$ is —C(R$^7$)(R$^8$)—(CH$_2$)$_p$—N(R$^9$)R$^{10}$;

or A$^1$ and A$^2$, together with the carbon atom to which they are attached, form

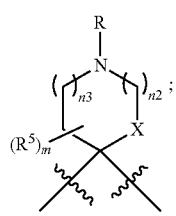

m is 0, 1 or 2;
n1 is 1 or 2;
n2 is 0 or 1;
n3 is 0 or 1;
p is 0 or 1;
R is —H or C$_1$-C$_3$ alkyl; or R is —CH$_2$—(X), —CH$_2$CH$_2$—(X), —CH$_2$—(Z) or —CH$_2$CH$_2$—(Z);
each instance of R$^5$ independently is halo, —CH$_3$ or ethyl;
each instance of R$^6$ independently is halo or —CH$_3$;
R$^2$ is —H or C$_1$-C$_3$ alkyl;
R$^8$ is —H or C$_1$-C$_3$ alkyl which is unsubstituted or substituted with C$_3$-C$_6$ cycloalkyl;
R$^9$ is —H, C$_1$-C$_4$ alkyl or C$_3$-C$_6$ cycloalkyl; and
R$^{10}$ is —H or C$_1$-C$_3$ alkyl;
or R$^9$ and R$^8$, together with the atoms to which they are attached, form (i.e., R$^9$ and R$^8$, together with the atoms to which they are attached form a ring such that —C(R$^2$)(R$^8$)—(CH$_2$)$_p$—N(R$^9$)R$^{10}$ is)

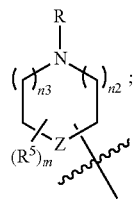

or R$^9$ and R$^{10}$, together with the nitrogen atom to which they are attached, form

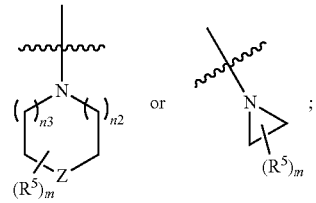

w is 0, 1 or 2;
X is CH or CH$_2$; and
Z is CH, CH$_2$ or O.

Such a compound (including pharmaceutically acceptable salts) is referred to herein as a "provided compound". Provided compounds are also described in U.S. Application No. 62/115,043, filed Feb. 11, 2015, which is hereby incorporated by reference herein in its entirety.

When R is "—CH$_2$—(X)" or "—CH$_2$CH$_2$—(X)", this means that the nitrogen atom bearing R is attached to the carbon atom represented by X with —CH$_2$— or —CH$_2$CH$_2$—, respectively. For example, when A$^1$ and A$^2$, together with the carbon atom to which they are attached, form

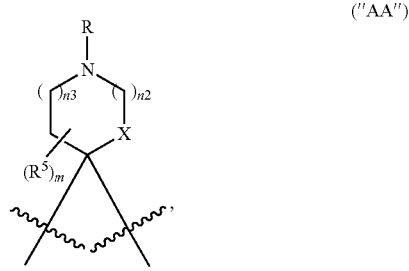

("AA")

if n2 is 1, n3 is 1 and m is 0:
if R is —CH$_2$—(X), then AA is

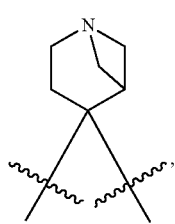 [SMILES: *C1(*)CCN2CC1C2]

, and if R is —CH$_2$CH$_2$—(X), then AA is

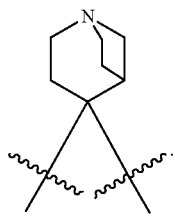 [SMILES: *C1(*)CCN2CCC1C2]

When R is —H or C$_1$-C$_3$ alkyl, then X is CH$_2$.

When R is "—CH$_2$—(Z)" or "—CH$_2$CH$_2$—(Z)", this means that the nitrogen atom bearing R is attached to the carbon atom represented by Z with —CH$_2$— or —CH$_2$CH$_2$—, respectively. For example, when R$^9$ and R$^8$, together with the atoms to which they are attached, form

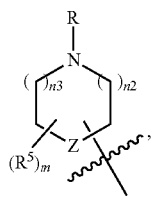
("R98")

if n2 is 1, n3 is 1 and m is 0:
if R is —CH$_2$—(Z), then R98 is

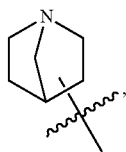

and if R is —CH$_2$CH$_2$—(Z), then R98 is

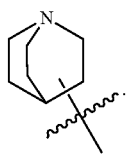

When R is —H or C$_1$-C$_3$ alkyl, then Z is CH$_2$ or 0.

In some embodiments, the present invention provides a compound of Formula (I):

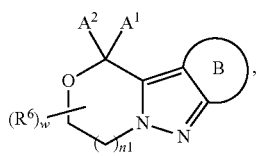
(I)

or a pharmaceutically acceptable salt thereof, wherein:

Ring B is a 6-membered aromatic ring, which ring is unsubstituted or substituted with 1 to 4 substituents independently selected from halo, —OH, —NH$_2$, —CH$_3$, —CH$_2$F, —CHF$_2$ and —CF$_3$; or is a 5- or 6-membered heteroaromatic ring having 1 to 3 ring heteroatoms independently selected from O, N and S, which ring is unsubstituted or substituted with 1 to 3 substituents independently selected from halo, —OH, —NH$_2$, —CH$_3$, —CH$_2$F, —CHF$_2$ and —CF$_3$;

A$^1$ is —H or C$_{1-3}$ alkyl; and

A$^2$ is —C(R$^2$)(R$^8$)—(CH$_2$)$_p$—N(R$^9$)R$^{10}$;

or A$^1$ and A$^2$, together with the carbon atom to which they are attached, form

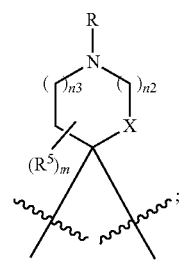

m is 0, 1 or 2;

n1 is 1 or 2;

n2 is 0 or 1;

n3 is 0 or 1;

p is 0 or 1;

R is —H or C$_1$-C$_3$ alkyl; or R is —CH$_2$—(X), —CH$_2$CH$_2$—(X), —CH$_2$—(Z) or —CH$_2$CH$_2$—(Z);

each instance of R$^5$ independently is halo, —CH$_3$ or ethyl;

each instance of R$^6$ independently is halo or —CH$_3$;

R$^7$ is —H or C$_1$-C$_3$ alkyl;

R$^8$ is —H or C$_1$-C$_3$ alkyl which is unsubstituted or substituted with C$_3$-C$_6$ cycloalkyl;

R$^9$ is —H, C$_1$-C$_4$ alkyl or C$_3$-C$_6$ cycloalkyl; and

R$^{10}$ is —H or C$_1$-C$_3$ alkyl;

or R$^9$ and R$^8$, together with the atoms to which they are attached, form (i.e., R$^9$ and R$^8$, together with the atoms to which they are attached form a ring such that —C(R$^7$)(R$^8$)—(CH$_2$)$_p$—N(R$^9$)R$^{10}$ is)

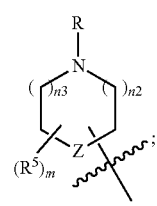

or R$^9$ and R$^{10}$, together with the nitrogen atom to which they are attached, form

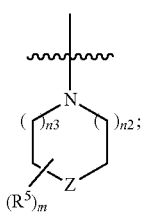

w is 0, 1 or 2;
X is CH or CH$_2$; and
Z is CH, CH$_2$ or O.

As defined above, Ring B is a 6-membered aromatic ring, which ring is unsubstituted or substituted with 1 to 4 substituents independently selected from halo, —OH, —NH$_2$, —CH$_3$, —CH$_2$F, —CHF$_2$ and —CF$_3$; or is a 5- or 6-membered heteroaromatic ring having 1 to 3 ring heteroatoms independently selected from O, N and S, which ring is unsubstituted or substituted with 1 to 3 substituents independently selected from halo, —OH, —NH$_2$, —CH$_3$, —CH$_2$F, —CHF$_2$ and —CF$_3$. This description of Ring B includes the 2 carbon atoms shared with the pyrazole moiety of Formula (I).

In some embodiments, Ring B is a 6-membered aromatic ring, which ring is unsubstituted or substituted with 1 to 4 substituents independently selected from halo, —OH, —NH$_2$, —CH$_3$, —CH$_2$F, —CHF$_2$ and —CF$_3$. In some embodiments, Ring B is a 6-membered aromatic ring, which ring is unsubstituted or substituted with 1 to 3 substituents independently selected from halo, —OH, —NH$_2$, —CH$_3$, —CH$_2$F, —CHF$_2$ and —CF$_3$. In some embodiments, Ring B is a 6-membered aromatic ring, which ring is unsubstituted or substituted with 1 or 2 substituents independently selected from halo, —OH, —NH$_2$, —CH$_3$, —CH$_2$F, —CHF$_2$ and —CF$_3$. In some embodiments, Ring B is a 6-membered aromatic ring, which ring is unsubstituted or substituted with 1 substituent selected from halo, —OH, —NH$_2$, —CH$_3$, —CH$_2$F, —CHF$_2$ and —CF$_3$. In some embodiments, Ring B is an unsubstituted 6-membered aromatic ring.

In some embodiments, Ring B is a 5- or 6-membered heteroaromatic ring having 1 to 3 ring heteroatoms independently selected from O, N and S, which ring is unsubstituted or substituted with 1 to 3 substituents independently selected from halo, —OH, —NH$_2$, —CH$_3$, —CH$_2$F, —CHF$_2$ and —CF$_3$. When the resulting compound is stable, a ring N atom can be substituted with —CH$_3$.

In some embodiments, Ring B is a 5-membered heteroaromatic ring having 1 to 3 ring heteroatoms independently selected from O, N and S, which ring is unsubstituted or substituted with 1 to 3 substituents independently selected from halo, —OH, —NH$_2$, —CH$_3$, —CH$_2$F, —CHF$_2$ and —CF$_3$. In some embodiments, Ring B is a 5-membered heteroaromatic ring having 1 or 2 ring heteroatoms independently selected from O, N and S, which ring is unsubstituted or substituted with 1 to 3 substituents independently selected from halo, —OH, —NH$_2$, —CH$_3$, —CH$_2$F, —CHF$_2$ and —CF$_3$. In some embodiments, Ring B is a 5-membered heteroaromatic ring having 1 ring heteroatom selected from O, N and S, which ring is unsubstituted or substituted with 1 to 3 substituents independently selected from halo, —OH, —NH$_2$, —CH$_3$, —CH$_2$F, —CHF$_2$ and —CF$_3$.

In some embodiments, Ring B is any 5-membered heteroaromatic ring described in the preceding paragraph, which ring is unsubstituted or substituted with 1 or 2 substituents independently selected from halo, —OH, —NH$_2$, —CH$_3$, —CH$_2$F, —CHF$_2$ and —CF$_3$. In some embodiments, Ring B is any 5-membered heteroaromatic ring described in the preceding paragraph, which ring is unsubstituted or substituted with 1 substituent selected from halo, —OH, —NH$_2$, —CH$_3$, —CH$_2$F, —CHF$_2$ and —CF$_3$. In some embodiments, Ring B is any 5-membered heteroaromatic ring described in the preceding paragraph, which ring is unsubstituted.

In some embodiments, Ring B is a 6-membered heteroaromatic ring having 1 to 3 ring heteroatoms independently selected from O, N and S, which ring is unsubstituted or substituted with 1 to 3 substituents independently selected from halo, —OH, —NH$_2$, —CH$_3$, —CH$_2$F, —CHF$_2$ and —CF$_3$. In some embodiments, Ring B is a 6-membered heteroaromatic ring having 1 or 2 ring heteroatoms independently selected from O, N and S, which ring is unsubstituted or substituted with 1 to 3 substituents independently selected from halo, —OH, —NH$_2$, —CH$_3$, —CH$_2$F, —CHF$_2$ and —CF$_3$. In some embodiments, Ring B is a 6-membered heteroaromatic ring having 1 ring heteroatom selected from O, N and S, which ring is unsubstituted or substituted with 1 to 3 substituents independently selected from halo, —OH, —NH$_2$, —CH$_3$, —CH$_2$F, —CHF$_2$ and —CF$_3$.

In some embodiments, Ring B is any 6-membered heteroaromatic ring described in the preceding paragraph, which ring is unsubstituted or substituted with 1 or 2 substituents independently selected from halo, —OH, —NH$_2$, —CH$_3$, —CH$_2$F, —CHF$_2$ and —CF$_3$. In some embodiments, Ring B is any 6-membered heteroaromatic ring described in the preceding paragraph, which ring is unsubstituted or substituted with 1 substituent selected from halo, —OH, —NH$_2$, —CH$_3$, —CH$_2$F, —CHF$_2$ and —CF$_3$. In some embodiments, Ring B is any 6-membered heteroaromatic ring described in the preceding paragraph, which ring is unsubstituted.

As defined above, in some embodiments, A$^1$ is —H or C$_{1-3}$ alkyl. In some embodiments, A$^1$ is —H or —CH$_3$. In some embodiments, A$^1$ is —H.

As defined above, n1 is 1 or 2. In some embodiments, n1 is 1. In some embodiments, n1 is 2.

As defined above, w is 0, 1 or 2. In some embodiments, w is 0 or 1. In some embodiments, w is 0. In some embodiments, w is 1 or 2. In some embodiments, w is 1.

As defined above, each instance of R$^6$ independently is halo or —CH$_3$. In some embodiments, each instance of R$^6$ independently is halo. In some embodiments, each instance of R$^6$ independently is —F or —Cl. In some embodiments, each instance of R$^6$ is —CH$_3$.

As defined above, in some embodiments, A$^2$ is —C(R$^2$)(R$^8$)—(CH$_2$)$_p$—N(R$^9$)R$^{10}$. In some embodiments, p is 0. In some embodiments, R$^2$ is —H or —CH$_3$; and R$^8$ is H or unsubstituted C$_1$-C$_3$ alkyl. In some embodiments, R$^2$ is —H; and R$^8$ is H or —CH$_3$. In some embodiments, R$^9$ is —H, C$_1$-C$_3$ alkyl, cyclopropyl or cyclobutyl; and R$^{10}$ is —H or C$_1$-C$_2$ alkyl. In some embodiments, R$^9$ is —H or C$_1$-C$_3$ alkyl; and R$^{10}$ is —H or —CH$_3$. In some embodiments, p is 0; R$^2$ is —H or —CH$_3$; R$^8$ is H or unsubstituted C$_1$-C$_3$ alkyl; R$^9$ is —H, C$_1$-C$_3$ alkyl, cyclopropyl or cyclobutyl; and R$^{10}$ is —H or C$_1$-C$_2$ alkyl. In some embodiments, p is 0; R$^2$ is —H; R$^8$ is H or —CH$_3$; R$^9$ is —H or C$_1$-C$_3$ alkyl; and R$^{10}$ is —H or —CH$_3$. In some embodiments, R$^9$ and R$^{10}$, together with the nitrogen atom to which they are attached, form

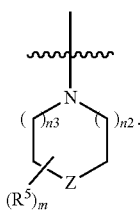

In some embodiments, one of n2 and n3 is 0 and the other is 1. In some embodiments, each of n2 and n3 is 1. In some embodiments, m is 0 or 1. In some embodiments, m is 0. In some embodiments, m is 1 or 2. In some embodiments, m is 1. In some embodiments, $R^5$ is halo. In some embodiments, $R^5$ is —F or —Cl. In some embodiments, $R^5$ is —CH$_3$ or ethyl. In some embodiments, $R^5$ is —CH$_3$. In some embodiments, Z is CH or CH$_2$. In some embodiments, Z is O. In some embodiments, each of n2 and n3 is 1; and Z is O.

As defined above, in some embodiments, $A^2$ is —C($R^7$)($R^8$)—(CH$_2$)$_p$—N($R^9$)$R^{10}$. In some embodiments, p is 0. In some embodiments, $R^7$ is —H or —CH$_3$; and $R^8$ is H or unsubstituted $C_1$-$C_3$ alkyl. In some embodiments, $R^7$ is —H; and $R^8$ is H or —CH$_3$. In some embodiments, $R^9$ is —H, $C_1$-$C_3$ alkyl, cyclopropyl or cyclobutyl; and $R^{10}$ is —H or $C_1$-$C_2$ alkyl. In some embodiments, $R^9$ is —H or $C_1$-$C_3$ alkyl; and $R^{10}$ is —H or —CH$_3$. In some embodiments, p is 0; $R^7$ is —H or —CH$_3$; $R^8$ is H or unsubstituted $C_1$-$C_3$ alkyl; $R^9$ is —H, $C_1$-$C_3$ alkyl, cyclopropyl or cyclobutyl; and $R^{10}$ is —H or $C_1$-$C_2$ alkyl. In some embodiments, p is 0; $R^7$ is —H; $R^8$ is H or —CH$_3$; $R^9$ is —H or $C_1$-$C_3$ alkyl; and $R^{10}$ is —H or —CH$_3$. In some embodiments, $R^9$ and $R^{10}$, together with the nitrogen atom to which they are attached, form

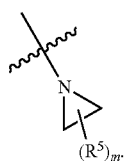

In some embodiments, m is 0 or 1. In some embodiments, m is 0. In some embodiments, m is 1 or 2. In some embodiments, m is 1. In some embodiments, $R^5$ is halo. In some embodiments, $R^5$ is —F or —Cl. In some embodiments, $R^5$ is —CH$_3$ or ethyl. In some embodiments, $R^5$ is —CH$_3$.

In some embodiments, $R^9$ and $R^8$, together with the atoms to which they are attached, form (i.e., $R^9$ and $R^8$, together with the atoms to which they are attached form a ring such that —C($R^2$)($R^8$)—(CH$_2$)$_p$—N($R^9$)$R^{10}$ is)

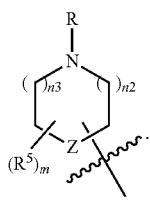

In some embodiments, each of n2 and n3 is 0. In some embodiments, one of n2 and n3 is 0 and the other is 1. In some embodiments, each of n2 and n3 is 1. In some embodiments, m is 0 or 1. In some embodiments, m is 0. In some embodiments, m is 1 or 2. In some embodiments, m is 1. In some embodiments, $R^5$ is halo. In some embodiments, $R^5$ is —F or —Cl. In some embodiments, $R^5$ is —CH$_3$ or ethyl. In some embodiments, $R^5$ is —CH$_3$. In some embodiments, R is —H or $C_1$-$C_3$ alkyl. In some embodiments, R is —H or —CH$_3$. In some embodiments, R is —H. In some embodiments, R is —CH$_3$. In some embodiments, R is —CH$_2$—(Z) or —CH$_2$CH$_2$—(Z). In some embodiments, R is —CH$_2$—(Z). In some embodiments, R is —CH$_2$CH$_2$—(Z). In some embodiments, Z is CH or CH$_2$. In some embodiments, Z is O. In some embodiments, each of n2 and n3 is 1; and Z is O.

As defined above, in some embodiments, or $A^1$ and $A^2$, together with the carbon atom to which they are attached, form

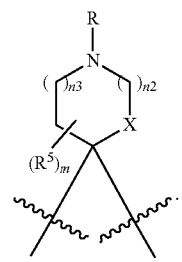

In some embodiments, each of n2 and n3 is 0. In some embodiments, one of n2 and n3 is 0 and the other is 1. In some embodiments, each of n2 and n3 is 1. In some embodiments, m is 0 or 1. In some embodiments, m is 0. In some embodiments, m is 1 or 2. In some embodiments, m is 1. In some embodiments, $R^5$ is halo. In some embodiments, $R^5$ is —F or —Cl. In some embodiments, $R^5$ is —CH$_3$ or ethyl. In some embodiments, $R^5$ is —CH$_3$. In some embodiments, R is —H or $C_1$-$C_3$ alkyl. In some embodiments, R is —H or —CH$_3$. In some embodiments, R is —H. In some embodiments, R is —CH$_3$. In some embodiments, R is —CH$_2$—(X) or —CH$_2$CH$_2$—(X). In some embodiments, R is —CH$_2$—(X).

In some embodiments, a provided compound is a compound of Formula (I-1):

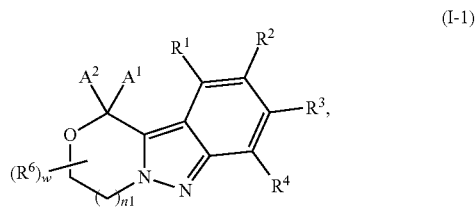

(I-1)

or a pharmaceutically acceptable salt thereof, wherein each of $A^1$, $A^2$, n1, $R^6$ and w is as described in embodiments for Formula (I), supra, or described in embodiments herein, both singly and in combination; and $R^1$, $R^2$, $R^3$ and $R^4$ are independently —H, halo, —OH, —NH$_2$, —CH$_3$, —CH$_2$F, —CHF$_2$ or —CF$_3$.

In some embodiments, at least two of $R^1$, $R^2$, $R^3$ and $R^4$ are —H. In some embodiments, at least three of $R^1$, $R^2$, $R^3$ and $R^4$ are —H. In some embodiments, each of $R^1$, $R^2$, $R^3$ and $R^4$ is —H. In some embodiments, $R^1$, $R^2$, $R^3$ and $R^4$ are independently —H, halo or —CH₃. In some embodiments, R¹, R², R³ and R⁴ are independently —H, —F or —Cl. In some embodiments, each of R¹, R³ and R⁴ is —H. In some embodiments, each of R¹, R³ and R⁴ is —H; and R² is —H, halo or —CH₃. In some embodiments, each of R¹, R³ and R⁴ is —H; and R² is H, —F or —Cl. In some embodiments, each of R¹, R² and R⁴ is —H. In some embodiments, each of R¹, R² and R⁴ is —H; and R³ is —H, halo or —CH₃. In some embodiments, each of R¹, R² and R⁴ is —H; and R³ is H, —F or —Cl.

In some embodiments, a provided compound is a compound of Formula (I-1-A):

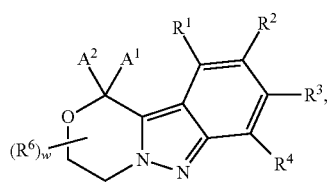

(I-1-A)

or a pharmaceutically acceptable salt thereof, wherein each of A¹, A², R⁶ and w is as described in embodiments for Formula (I), supra, or described in embodiments herein, both singly and in combination; and each of R¹, R², R³ and R⁴ is as described in embodiments for Formula (I-1), supra, or described in embodiments herein, both singly and in combination.

In some embodiments, a provided compound is a compound of Formula (I-1-B):

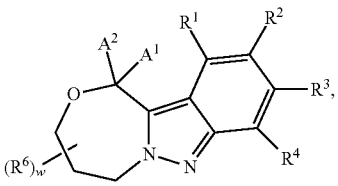

(I-1-B)

or a pharmaceutically acceptable salt thereof, wherein each of A¹, A², R⁶ and w is as described in embodiments for Formula (I), supra, or described in embodiments herein, both singly and in combination; and each of R¹, R², R³ and R⁴ is as described in embodiments for Formula (I-1), supra, or described in embodiments herein, both singly and in combination.

In some embodiments, a provided compound is a compound of Formula (I-2):

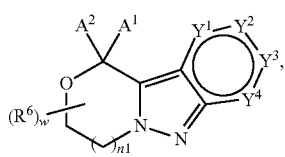

(I-2)

or a pharmaceutically acceptable salt thereof, wherein each of A¹, A², n1, R⁶ and w is as described in embodiments for Formula (I), supra, or described in embodiments herein, both singly and in combination;

Y¹ is N or CR¹';
Y² is N or CR²';
Y³ is N or CR³'; and
Y⁴ is N or CR⁴';
    wherein 1 to 3 of Y¹, Y², Y³ and Y⁴ are N; and
    R¹', R²', R³' and R⁴' are independently —H, halo, —OH, —NH₂, —CH₃, —CH₂F, —CHF₂ or —CF₃.

In some embodiments, R¹', R²', R³' and R⁴' are independently —H, halo or —CH₃. In some embodiments, R¹', R²', R³' and R⁴' are independently —H, —F or —Cl.

In some embodiments, 2 of Y¹, Y², Y³ and Y⁴ are N. In some embodiments, 2 of Y¹, Y², Y³ and Y⁴ are N; and R¹', R²', R³' and R⁴' are independently —H, halo or —CH₃. In some embodiments, 2 of Y¹, Y², Y³ and Y⁴ are N; and R¹', R²', R³' and R⁴' are independently —H, —F or —Cl. In some embodiments, 2 of Y¹, Y², Y³ and Y⁴ are N; and at least 1 of Y¹, Y², Y³ and Y⁴ is CH.

In some embodiments, 1 of Y¹, Y², Y³ and Y⁴ is N. In some embodiments, 1 of Y¹, Y², Y³ and Y⁴ is N; and R¹', R²', R³' and R⁴' are independently —H, halo or —CH₃. In some embodiments, 1 of Y¹, Y², Y³ and Y⁴ is N; and R¹', R²', R³' and R⁴' are independently —H, —F or —Cl. In some embodiments, 1 of Y¹, Y², Y³ and Y⁴ is N; and at least 2 of Y¹, Y², Y³ and Y⁴ are CH. In some embodiments, Y² is N; and R¹', R³' and R⁴' are independently —H, halo or —CH₃. In some embodiments, Y² is N; and R¹', R³' and R⁴' are independently —H, —F or —Cl. In some embodiments, Y³ is N; and R¹', R²' and R⁴' are independently —H, halo or —CH₃. In some embodiments, Y³ is N; and R¹', R²' and R⁴' are independently —H, —F or —Cl.

In some embodiments, a provided compound is a compound of Formula (I-2-A):

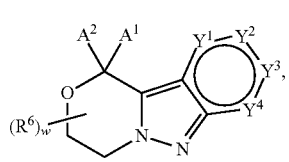

(I-2-A)

or a pharmaceutically acceptable salt thereof, wherein each of A¹, A², R⁶ and w is as described in embodiments for Formula (I), supra, or described in embodiments herein, both singly and in combination; and each of Y¹, Y², Y³ and Y⁴ is as described in embodiments for Formula (I-2), supra, or described in embodiments herein, both singly and in combination.

In some embodiments, a provided compound is a compound of Formula (I-2-B):

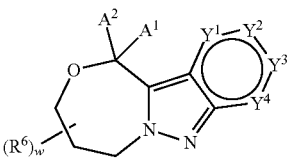

(I-2-B)

or a pharmaceutically acceptable salt thereof, wherein each of A¹, A², R⁶ and w is as described in embodiments for Formula (I), supra, or described in embodiments herein, both singly and in combination; and each of Y¹, Y², Y³ and Y⁴ is as described in embodiments for Formula (I-2), supra, or described in embodiments herein, both singly and in combination.

In some embodiments, a provided compound is a compound of Formula (I-2-i):

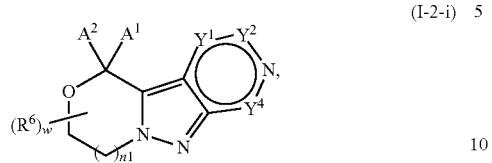

(I-2-i)

or a pharmaceutically acceptable salt thereof, wherein each of $A^1$, $A^2$, n1, $R^6$ and w is as described in embodiments for Formula (I), supra, or described in embodiments herein, both singly and in combination; and each of $Y^1$, $Y^2$ and $Y^4$ is as described in embodiments for Formula (I-2), supra, or described in embodiments herein, both singly and in combination.

In some embodiments, a provided compound is a compound of Formula (I-3):

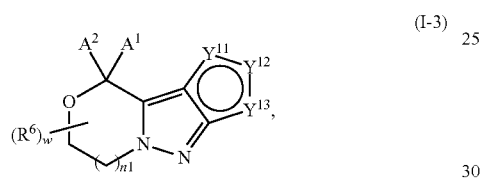

(I-3)

or a pharmaceutically acceptable salt thereof, wherein each of $A^1$, $A^2$, n1, $R^6$ and w is as described in embodiments for Formula (I), supra, or described in embodiments herein, both singly and in combination;

$Y^{11}$ is $CR^{1'''}$ or a heteroatom selected from O, S, N and $NR^{11}$;
$Y^{12}$ is $CR^{2'''}$ or a heteroatom selected from O, S, N and $NR^{12}$; and
$Y^{13}$ is $CR^{3'''}$ or a heteroatom selected from O, S, N and $NR^{13}$;
wherein at least one of $Y^{11}$, $Y^{12}$, and $Y^{13}$ is a heteroatom;
$R^{1'''}$, $R^{2'''}$ and $R^{3'''}$ are independently —H, halo, —OH, —NH$_2$, —CH$_3$, —CH$_2$F, —CHF$_2$ or —CF$_3$; and $R^{11}$, $R^{12}$ and $R^{13}$ are independently —H or —CH$_3$.

In some embodiments, $R^{1'''}$, $R^{2'''}$ and $R^{3'''}$ are independently —H, halo, or —CH$_3$. In some embodiments, $R^{1'''}$, $R^{2'''}$ and $R^{3'''}$ are independently —H, —F or —Cl.

In some embodiments, 2 of $Y^{11}$, $Y^{12}$ and $Y^{13}$ are heteroatoms. In some embodiments, 2 of $Y^{11}$, $Y^{12}$ and $Y^{13}$ are heteroatoms; and $R^{1'''}$, $R^{2'''}$ and $R^{3'''}$ are independently —H, halo, or —CH$_3$. In some embodiments, 2 of $Y^{11}$, $Y^{12}$ and $Y^{13}$ are heteroatoms; and $R^{1'''}$, $R^{2'''}$ and $R^{3'''}$ are independently —H, —F or —Cl. In some embodiments, 2 of $Y^{11}$, $Y^{12}$ and $Y^{13}$ are heteroatoms; and 1 of $Y^{11}$, $Y^{12}$ and $Y^{13}$ is CH.

In some embodiments, 1 of $Y^{11}$, $Y^{12}$ and $Y^{13}$ is a heteroatom. In some embodiments, 1 of $Y^{11}$, $Y^{12}$ and $Y^{13}$ is a heteroatom; and $R^{1'''}$, $R^{2'''}$ and $R^{3'''}$ are independently —H, halo, or —CH$_3$. In some embodiments, 1 of $Y^{11}$, $Y^{12}$ and $Y^{13}$ is a heteroatom; and $R^{1'''}$, $R^{2'''}$ and $R^{3'''}$ are independently —H, —F or —Cl. In some embodiments, 1 of $Y^{11}$, $Y^{12}$ and $Y^{13}$ is a heteroatom; and at least 1 of $Y^{11}$, $Y^{12}$ and $Y^{13}$ is CH. In some embodiments, $Y^{11}$ is a heteroatom. In some embodiments, $Y^{11}$ is a heteroatom; and $R^{2'''}$ and $R^{3'''}$ are independently —H, halo, or —CH$_3$. In some embodiments, $Y^{11}$ is a heteroatom; and $R^{2'''}$ and $R^{3'''}$ are independently —H, —F or —Cl. In some embodiments, $Y^{11}$ is a heteroatom; and at least 1 of $Y^{12}$ and $Y^{13}$ is CH.

In some embodiments, a provided compound is a compound of Formula (I-3-A):

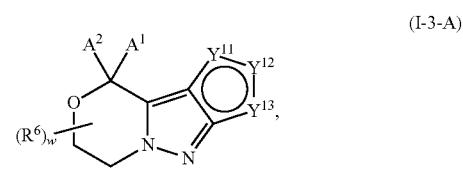

(I-3-A)

or a pharmaceutically acceptable salt thereof, wherein each of $A^1$, $A^2$, $R^6$ and w is as described in embodiments for Formula (I), supra, or described in embodiments herein, both singly and in combination; and each of $Y^{11}$, $Y^{12}$ and $Y^{13}$ is as described in embodiments for Formula (I-3), supra, or described in embodiments herein, both singly and in combination.

In some embodiments, a provided compound is a compound of Formula (I-3-B):

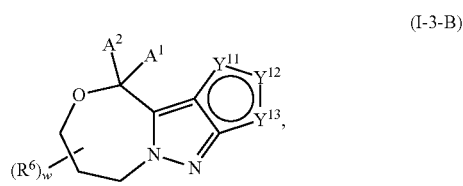

(I-3-B)

or a pharmaceutically acceptable salt thereof, wherein each of $A^1$, $A^2$, $R^6$ and w is as described in embodiments for Formula (I), supra, or described in embodiments herein, both singly and in combination; and each of $Y^{11}$, $Y^{12}$ and $Y^{13}$ is as described in embodiments for Formula (I-3), supra, or described in embodiments herein, both singly and in combination.

In some embodiments, a provided compound is a compound of Formula (I-3-i):

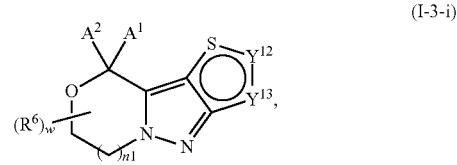

(I-3-i)

or a pharmaceutically acceptable salt thereof, wherein each of $A^1$, $A^2$, n1, $R^6$ and w is as described in embodiments for Formula (I), supra, or described in embodiments herein, both singly and in combination; and each of $Y^{12}$ and $Y^{13}$ is as described in embodiments for Formula (I-3), supra, or described in embodiments herein, both singly and in combination.

In some embodiments, a provided compound is a compound of Formula (I-3-ii):

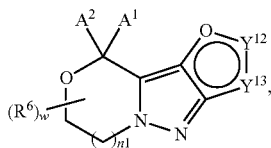

(I-3-ii)

or a pharmaceutically acceptable salt thereof, wherein each of $A^1$, $A^2$, n1, $R^6$ and w is as described in embodiments for Formula (I), supra, or described in embodiments herein, both singly and in combination; and each of $Y^{12}$ and $Y^{13}$ is as described in embodiments for Formula (I-3), supra, or described in embodiments herein, both singly and in combination.

In some embodiments, a provided compound is a compound of Formula (I-3-iii):

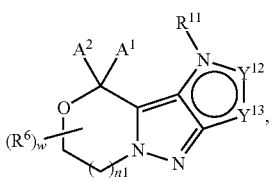

(I-3-iii)

or a pharmaceutically acceptable salt thereof, wherein each of $A^1$, $A^2$, n1, $R^6$ and w is as described in embodiments for Formula (I), supra, or described in embodiments herein, both singly and in combination; and each of $Y^{12}$ and $Y^{13}$ is as described in embodiments for Formula (I-3), supra, or described in embodiments herein, both singly and in combination. In some embodiments, $R^{11}$ is —H.

In some embodiments, a provided compound is a compound of Formula (II):

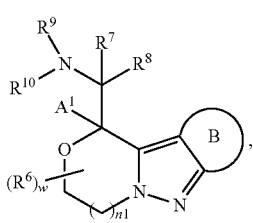

(II)

or a pharmaceutically acceptable salt thereof, wherein each of Ring B, $A^1$, n1, $R^6$, $R^7$, $R^8$, $R^9$, $R^{10}$ and w is as described in embodiments for Formula (I), supra, or described in embodiments herein, both singly and in combination.

In some embodiments, a provided compound is a compound of Formula (II-1):

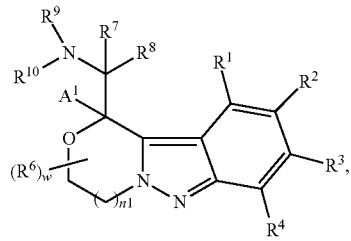

(II-1)

or a pharmaceutically acceptable salt thereof, wherein each of $A^1$, n1, $R^6$, $R^7$, $R^8$, $R^9$, $R^{10}$ and w is as described in embodiments for Formula (I), supra, or described in embodiments herein, both singly and in combination; and each of $R^1$, $R^2$, $R^3$ and $R^4$ is as described in embodiments for Formula (I-1), supra, or described in embodiments herein, both singly and in combination.

In some embodiments, w is 0. In some embodiments, each of $R^1$ and $R^4$ is —H. In some embodiments, w is 0; and each of $R^1$ and $R^4$ is —H. In some embodiments, $R^2$ is —H; and $R^8$ is —H or —CH$_3$. In some embodiments, w is 0; each of $R^1$ and $R^4$ is —H; $R^2$ is —H; and $R^8$ is —H or —CH$_3$. In some embodiments, $A^1$ is —H or —CH$_3$. In some embodiments, w is 0; each of $R^1$ and $R^4$ is —H; $R^2$ is —H; $R^8$ is —H or —CH$_3$; and $A^1$ is —H. In some embodiments, w is 0; each of $R^1$, $R^2$ and $R^4$ is —H; $R^2$ is —H; $R^8$ is —H or —CH$_3$; and $A^1$ is —H. In some embodiments, w is 0; each of $R^1$, $R^2$ and $R^4$ is —H; $R^3$ is halo; $R^2$ is —H; $R^8$ is —H or —CH$_3$; and $A^1$ is —H. In some embodiments, w is 0; each of $R^1$, $R^2$ and $R^4$ is —H; $R^3$ is —F or —Cl; $R^2$ is —H; $R^8$ is —H or —CH$_3$; and $A^1$ is —H. In some embodiments, w is 0; each of $R^1$, $R^3$ and $R^4$ is —H; $R^2$ is —H; $R^8$ is —H or —CH$_3$; and $A^1$ is —H. In some embodiments, w is 0; each of $R^1$, $R^3$ and $R^4$ is —H; $R^2$ is halo; $R^2$ is —H; $R^8$ is —H or —CH$_3$; and $A^1$ is —H. In some embodiments, w is 0; each of $R^1$, $R^3$ and $R^4$ is —H; $R^2$ is —F or —Cl; $R^2$ is —H; $R^8$ is —H or —CH$_3$; and $A^1$ is —H. In some embodiments, w is 0; each of $R^1$, $R^2$, $R^3$ and $R^4$ is —H; $R^2$ is —H; $R^8$ is —H or —CH$_3$; and $A^1$ is —H.

In some embodiments, n1 is 1. In some embodiments, n1 is 1; w is 0; each of $R^1$, $R^2$ and $R^4$ is —H; $R^2$ is —H; $R^8$ is —H or —CH$_3$; and $A^1$ is —H. In some embodiments, n1 is 1; w is 0; each of $R^1$, $R^2$ and $R^4$ is —H; $R^3$ is halo; $R^2$ is —H; $R^8$ is —H or —CH$_3$; and $A^1$ is —H. In some embodiments, n1 is 1; w is 0; each of $R^1$, $R^2$ and $R^4$ is —H; $R^3$ is —F or —Cl; $R^2$ is —H; $R^8$ is —H or —CH$_3$; and $A^1$ is —H. In some embodiments, n1 is 1; w is 0; each of $R^1$, $R^3$ and $R^4$ is —H; $R^2$ is —H; $R^8$ is —H or —CH$_3$; and $A^1$ is —H. In some embodiments, n1 is 1; w is 0; each of $R^1$, $R^3$ and $R^4$ is —H; $R^2$ is halo; $R^2$ is —H; $R^8$ is —H or —CH$_3$; and $A^1$ is —H. In some embodiments, n1 is 1; w is 0; each of $R^1$, $R^3$ and $R^4$ is —H; $R^2$ is —F or —Cl; $R^2$ is —H; $R^8$ is —H or —CH$_3$; and $A^1$ is —H. In some embodiments, n1 is 1; w is 0; each of $R^1$, $R^2$, $R^3$ and $R^4$ is —H; $R^2$ is —H; $R^8$ is —H or —CH$_3$; and $A^1$ is —H.

In some embodiments, n1 is 2. In some embodiments, n1 is 2; w is 0; each of $R^1$, $R^2$ and $R^4$ is —H; $R^2$ is —H; $R^8$ is —H or —CH$_3$; and $A^1$ is —H. In some embodiments, n1 is 2; w is 0; each of $R^1$, $R^2$ and $R^4$ is —H; $R^3$ is halo; $R^2$ is —H; $R^8$ is —H or —CH$_3$; and $A^1$ is —H. In some embodiments, n1 is 2; w is 0; each of $R^1$, $R^2$ and $R^4$ is —H; $R^3$ is —F or —Cl; $R^2$ is —H; $R^8$ is —H or —CH$_3$; and $A^1$ is —H. In some embodiments, n1 is 2; w is 0; each of $R^1$, $R^3$ and $R^4$ is —H; $R^2$ is —H; $R^8$ is —H or —CH$_3$; and $A^1$ is —H. In some embodiments, n1 is 2; w is 0; each of $R^1$, $R^3$ and $R^4$ is —H; $R^2$ is halo; $R^2$ is —H; $R^8$ is —H or —CH$_3$; and $A^1$ is —H. In some embodiments, n1 is 2; w is 0; each of $R^1$, $R^3$ and $R^4$ is —H; $R^2$ is —F or —Cl; $R^2$ is —H; $R^8$ is —H or —CH$_3$; and $A^1$ is —H. In some embodiments, n1 is 2; w is 0; each of $R^1$, $R^2$, $R^3$ and $R^4$ is —H; $R^2$ is —H; $R^8$ is —H or —CH$_3$; and $A^1$ is —H.

In some embodiments, $R^9$ and $R^{10}$, together with the nitrogen atom to which they are attached, form

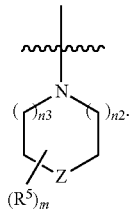

In some embodiments, $R^9$ and $R^{10}$, together with the nitrogen atom to which they are attached, form

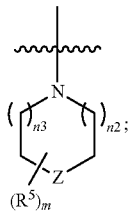

and (a) w is 0; (b) each of $R^1$ and $R^4$ is —H; (c) w is 0; and each of $R^1$ and $R^4$ is —H; (d) $A^1$ is —H or —CH$_3$; (e) w is 0; each of $R^1$ and $R^4$ is —H; and $A^1$ is —H; (f) m is 0; (g) w is 0; each of $R^1$ and $R^4$ is —H; $A^1$ is —H; and m is 0; (h) w is 0; each of $R^1$, $R^2$ and $R^4$ is —H; $A^1$ is —H; and m is 0; (i) w is 0; each of $R^1$, $R^3$ and $R^4$ is —H; $A^1$ is —H; and m is 0; (j) w is 0; each of $R^1$, $R^2$, $R^3$ and $R^4$ is —H; $A^1$ is —H; and m is 0; (k) one of n2 and n3 is 0 and the other is 1; (l) w is 0; each of $R^1$, $R^2$, $R^3$ and $R^4$ is —H; $A^1$ is —H; m is 0; and one of n2 and n3 is 0 and the other is 1; (m) w is 0; each of $R^1$, $R^2$, $R^3$ and $R^4$ is —H; $A^1$ is —H; m is 0; one of n2 and n3 is 0 and the other is 1; and Z is CH$_2$; (n) each of n2 and n3 is 1; (o) w is 0; each of $R^1$, $R^2$, $R^3$ and $R^4$ is —H; $A^1$ is —H; m is 0; and each of n2 and n3 is 1; or (p) w is 0; each of $R^1$, $R^2$, $R^3$ and $R^4$ is —H; $A^1$ is —H; m is 0; each of n2 and n3 is 1; and Z is O.

In some embodiments, $R^9$ and $R^{10}$, together with the nitrogen atom to which they are attached, form

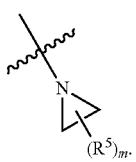

In some embodiments, $R^9$ and $R^{10}$, together with the nitrogen atom to which they are attached, form

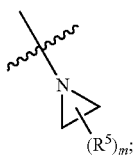

and (a) w is 0; (b) each of $R^1$ and $R^4$ is —H; (c) w is 0; and each of $R^1$ and $R^4$ is —H; (d) $A^1$ is —H or —CH$_3$; (e) w is 0; each of $R^1$ and $R^4$ is —H; and $A^1$ is —H; (f) m is 0; (g) w is 0; each of $R^1$ and $R^4$ is —H; $A^1$ is —H; and m is 0; (h) w is 0; each of $R^1$, $R^2$ and $R^4$ is —H; $A^1$ is —H; and m is 0; (i) w is 0; each of $R^1$, $R^3$ and $R^4$ is —H; $A^1$ is —H; and m is 0; or (j) w is 0; each of $R^1$, $R^2$, $R^3$ and $R^4$ is —H; $A^1$ is —H; and m is 0.

In some embodiments, a provided compound is a compound of Formula (II-1a):

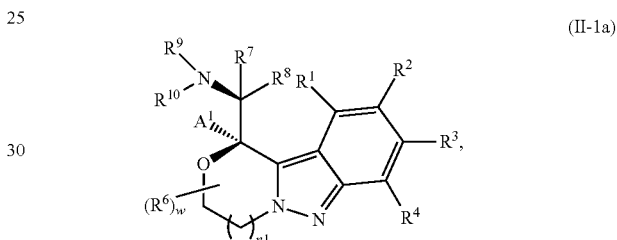

or a pharmaceutically acceptable salt thereof, wherein each of $A^1$, n1, $R^6$, $R^7$, $R^8$, $R^9$, $R^{10}$ and w is as described in embodiments for Formula (I) or (II-1), supra, or described in embodiments herein, both singly and in combination; and each of $R^1$, $R^2$, $R^3$ and $R^4$ is as described in embodiments for Formula (I-1) or (II-1), supra, or described in embodiments herein, both singly and in combination.

In some embodiments, a provided compound is a compound of Formula (II-1b):

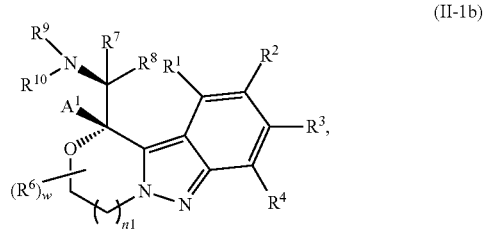

or a pharmaceutically acceptable salt thereof, wherein each of $A^1$, n1, $R^6$, $R^7$, $R^8$, $R^9$, $R^{10}$ and w is as described in embodiments for Formula (I) or (II-1), supra, or described in embodiments herein, both singly and in combination; and each of $R^1$, $R^2$, $R^3$ and $R^4$ is as described in embodiments for Formula (I-1) or (II-1), supra, or described in embodiments herein, both singly and in combination.

In some embodiments, a provided compound is a compound of Formula (II-2):

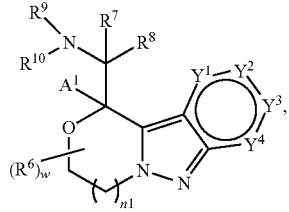

(II-2)

or a pharmaceutically acceptable salt thereof, wherein each of $A^1$, n1, $R^6$, $R^7$, $R^8$, $R^9$, $R^{10}$ and w is as described in embodiments for Formula (I), supra, or described in embodiments herein, both singly and in combination; and each of $Y^1$, $Y^2$, $Y^3$ and $Y^4$ is as described in embodiments for Formula (I-2), supra, or described in embodiments herein, both singly and in combination.

In some embodiments, w is 0. In some embodiments, each of $Y^1$ and $Y^4$ is CH. In some embodiments, w is 0; and each of $Y^1$ and $Y^4$ is CH. In some embodiments, $R^2$ is —H; and $R^8$ is —H or —CH$_3$. In some embodiments, w is 0; each of $Y^1$ and $Y^4$ is CH; and $R^8$ is —H or —CH$_3$. In some embodiments, $A^1$ is —H or —CH$_3$. In some embodiments, w is 0; each of $Y^1$ and $Y^4$ is CH; $R^2$ is —H; $R^8$ is —H or —CH$_3$; and $A^1$ is —H. In some embodiments, w is 0; each of $Y^1$, $Y^2$ and $Y^4$ is CH; $R^2$ is —H; $R^8$ is —H or —CH$_3$; and $A^1$ is —H. In some embodiments, w is 0; each of $Y^1$, $Y^2$ and $Y^4$ is CH; $R^2$ is —H; $R^8$ is —H or —CH$_3$; $A^1$ is —H; and n1 is 1.

In some embodiments, a provided compound is a compound of Formula (II-3):

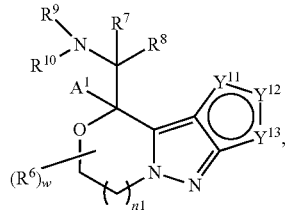

(II-3)

or a pharmaceutically acceptable salt thereof, wherein each of $A^1$, n1, $R^6$, $R^7$, $R^8$, $R^9$, $R^{10}$ and w is as described in embodiments for Formula (I), supra, or described in embodiments herein, both singly and in combination; and each of $Y^{11}$, $Y^{12}$ and $Y^{13}$ is as described in embodiments for Formula (I-3), supra, or described in embodiments herein, both singly and in combination.

In some embodiments, w is 0. In some embodiments, each of $Y^{12}$ and $Y^{13}$ is CH. In some embodiments, w is 0; and each of $Y^{12}$ and $Y^{13}$ is CH. In some embodiments, $R^7$ is —H; and $R^8$ is —H or —CH$_3$. In some embodiments, w is 0; each of e and e is CH; and $R^8$ is —H or —CH$_3$. In some embodiments, $A^1$ is —H or —CH$_3$. In some embodiments, w is 0; each of $Y^{12}$ and $Y^{13}$ is CH; $R^7$ is —H; $R^8$ is —H or —CH$_3$; and $A^1$ is —H. In some embodiments, w is 0; each of $Y^{12}$ and $Y^{13}$ is CH; $R^7$ is —H; $R^8$ is —H or —CH$_3$; $A^1$ is —H; and n1 is 1.

In some embodiments, a provided compound is a compound of Formula (III):

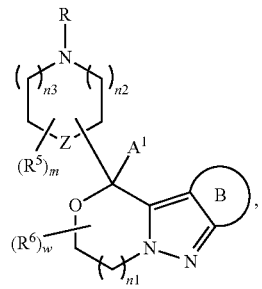

(III)

or a pharmaceutically acceptable salt thereof, wherein each of Ring B, $A^1$, m, n1, n2, n3, R, $R^5$, $R^6$, w and Z is as described in embodiments for Formula (I), supra, or described in embodiments herein, both singly and in combination.

In some embodiments, a provided compound is a compound of Formula (III-1):

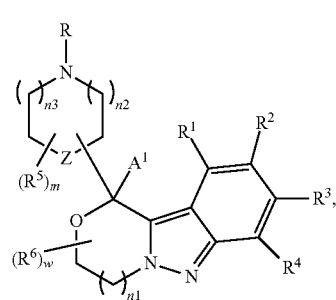

(III-1)

or a pharmaceutically acceptable salt thereof, wherein each of $A^1$, m, n1, n2, n3, R, $R^5$, $R^6$, w and Z is as described in embodiments for Formula (I), supra, or described in embodiments herein, both singly and in combination; and each of $R^1$, $R^2$, $R^3$ and $R^4$ is as described in embodiments for Formula (I-1), supra, or described in embodiments herein, both singly and in combination.

In some embodiments, (a) w is 0; (b) each of $R^1$ and $R^4$ is —H; (c) w is 0; and each of $R^1$ and $R^4$ is —H; (d) $A^1$ is —H or —CH$_3$; (e) w is 0; each of $R^1$ and $R^4$ is —H; and $A^1$ is —H; (f) m is 0; (g) w is 0; each of $R^1$ and $R^4$ is —H; $A^1$ is —H; and m is 0; (h) w is 0; each of $R^1$, $R^2$ and $R^4$ is —H; $A^1$ is —H; and m is 0; (i) w is 0; each of $R^1$, $R^3$ and $R^4$ is —H; $A^1$ is —H; and m is 0; (j) w is 0; each of $R^1$, $R^2$, $R^3$ and $R^4$ is —H; $A^1$ is —H; and m is 0; (k) R is —H or —CH$_3$; (l) w is 0; each of $R^1$, $R^2$, $R^3$ and $R^4$ is —H; $A^1$ is —H; m is 0; and R is —H or —CH$_3$; (m) one of n2 and n3 is 0 and the other is 1; (n) w is 0; each of $R^1$, $R^2$, $R^3$ and $R^4$ is —H; $A^1$ is —H; m is 0; R is —H or —CH$_3$; and one of n2 and n3 is 0 and the other is 1; (o) w is 0; each of $R^1$, $R^2$, $R^3$ and $R^4$ is —H; $A^1$ is —H; m is 0; R is —H or —CH$_3$; one of n2 and n3 is 0 and the other is 1; and Z is CH or CH$_2$; (p) each of n2 and n3 is 1; (q) w is 0; each of $R^1$, $R^2$, $R^3$ and $R^4$ is —H; $A^1$ is —H; m is 0; R is —H or —CH$_3$; and each of n2 and n3 is 1; (r) w is 0; each of $R^1$, $R^2$, $R^3$ and $R^4$ is —H; $A^1$ is —H; m is 0; R is —H or —CH$_3$; each of n2 and n3 is 1; and Z is CH or CH$_2$; or (s) w is 0; each of $R^1$, $R^2$, $R^3$ and $R^4$ is —H; $A^1$ is —H; m is 0; R is —H or —CH$_3$; each of n2 and n3 is 1; and Z is O.

In some embodiments, n1 is 1; and (a) w is 0; (b) each of $R^1$ and $R^4$ is —H; (c) w is 0; and each of $R^1$ and $R^4$ is —H;

(d) $A^1$ is —H or —CH$_3$; (e) w is 0; each of $R^1$ and $R^4$ is —H; and $A^1$ is —H; (f) m is 0; (g) w is 0; each of $R^1$ and $R^4$ is —H; $A^1$ is —H; and m is 0; (h) w is 0; each of $R^1$, $R^2$ and $R^4$ is —H; $A^1$ is —H; and m is 0; (i) w is 0; each of $R^1$, $R^3$ and $R^4$ is —H; $A^1$ is —H; and m is 0; (j) w is 0; each of $R^1$, $R^2$, $R^3$ and $R^4$ is —H; $A^1$ is —H; and m is 0; (k) R is —H or —CH$_3$; (l) w is 0; each of $R^1$, $R^2$, $R^3$ and $R^4$ is —H; $A^1$ is —H; m is 0; and R is —H or —CH$_3$; (m) one of n2 and n3 is 0 and the other is 1; (n) w is 0; each of $R^1$, $R^2$, $R^3$ and $R^4$ is —H; $A^1$ is —H; m is 0; R is —H or —CH$_3$; and one of n2 and n3 is 0 and the other is 1; (o) w is 0; each of $R^1$, $R^2$, $R^3$ and $R^4$ is —H; $A^1$ is —H; m is 0; R is —H or —CH$_3$; one of n2 and n3 is 0 and the other is 1; and Z is CH or CH$_2$; (p) each of n2 and n3 is 1; (q) w is 0; each of $R^1$, $R^2$, $R^3$ and $R^4$ is —H; $A^1$ is —H; m is 0; R is —H or —CH$_3$; and each of n2 and n3 is 1; (r) w is 0; each of $R^1$, $R^2$, $R^3$ and $R^4$ is —H; $A^1$ is —H; m is 0; R is —H or —CH$_3$; each of n2 and n3 is 1; and Z is CH or CH$_2$; or (s) w is 0; each of $R^1$, $R^2$, $R^3$ and $R^4$ is —H; $A^1$ is —H; m is 0; R is —H or —CH$_3$; each of n2 and n3 is 1; and Z is O.

In some embodiments, a provided compound is a compound of Formula (III-1a):

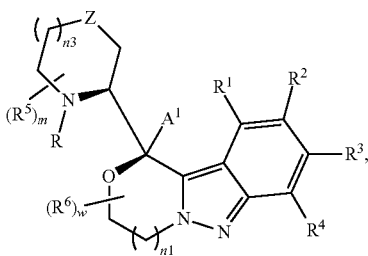

(III-1a)

or a pharmaceutically acceptable salt thereof, wherein each of $A^1$, m, n1, n3, R, $R^5$, $R^6$, w and Z is as described in embodiments for Formula (I) or (III-1), supra, or described in embodiments herein, both singly and in combination; and each of $R^1$, $R^2$, $R^3$ and $R^4$ is as described in embodiments for Formula (I-1) or (III-1), supra, or described in embodiments herein, both singly and in combination.

In some embodiments, a provided compound is a compound of Formula (III-1b):

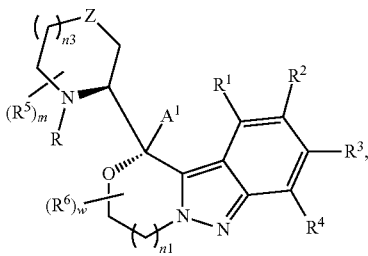

(III-1b)

or a pharmaceutically acceptable salt thereof, wherein each of $A^1$, m, n1, n3, R, $R^5$, $R^6$, w and Z is as described in embodiments for Formula (I) or (III-1), supra, or described in embodiments herein, both singly and in combination; and each of $R^1$, $R^2$, $R^3$ and $R^4$ is as described in embodiments for Formula (I-1) or (III-1), supra, or described in embodiments herein, both singly and in combination.

In some embodiments, a provided compound is a compound of Formula (III-1c):

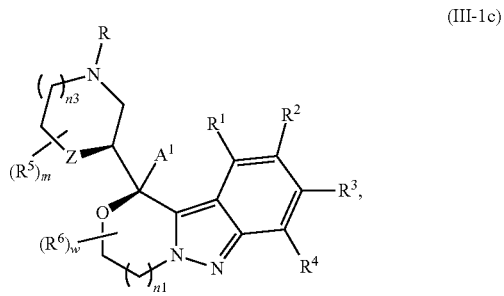

(III-1c)

or a pharmaceutically acceptable salt thereof, wherein each of $A^1$, m, n1, n3, R, $R^5$, $R^6$, w and Z is as described in embodiments for Formula (I) or (III-1), supra, or described in embodiments herein, both singly and in combination; and each of $R^1$, $R^2$, $R^3$ and $R^4$ is as described in embodiments for Formula (I-1) or (III-1), supra, or described in embodiments herein, both singly and in combination.

In some embodiments, a provided compound is a compound of Formula (III-1d):

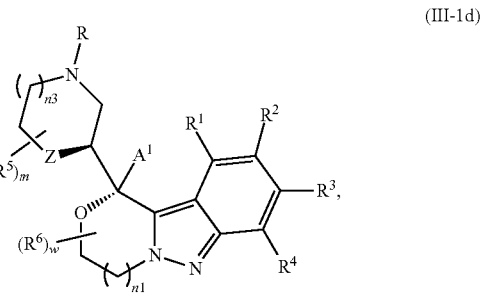

(III-1d)

or a pharmaceutically acceptable salt thereof, wherein each of $A^1$, m, n1, n3, R, $R^5$, $R^6$, w and Z is as described in embodiments for Formula (I) or (III-1), supra, or described in embodiments herein, both singly and in combination; and each of $R^1$, $R^2$, $R^3$ and $R^4$ is as described in embodiments for Formula (I-1) or (III-1), supra, or described in embodiments herein, both singly and in combination.

In some embodiments, a provided compound is a compound of Formula (III-2):

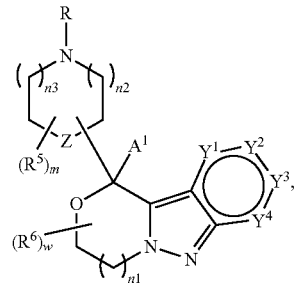

(III-2)

or a pharmaceutically acceptable salt thereof, wherein each of $A^1$, m, n1, n2, n3, R, $R^5$, $R^6$, w and Z is as described in embodiments for Formula (I), supra, or described in embodiments herein, both singly and in combination; and each of $Y^1$, $Y^2$, $Y^3$ and $Y^4$ is as described in embodiments for Formula (I-2), supra, or described in embodiments herein, both singly and in combination.

In some embodiments, a provided compound is a compound of Formula (III-3):

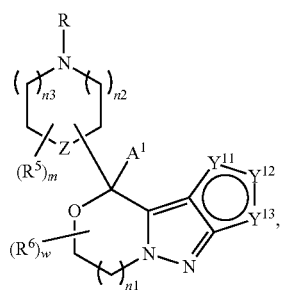

or a pharmaceutically acceptable salt thereof, wherein each of $A^1$, m, n1, n2, n3, R, $R^5$, $R^6$, w and Z is as described in embodiments for Formula (I), supra, or described in embodiments herein, both singly and in combination; and each of $Y^{11}$, $Y^{12}$ and $Y^{13}$ is as described in embodiments for Formula (I-3), supra, or described in embodiments herein, both singly and in combination.

In some embodiments, a provided compound is a compound of Formula (IV):

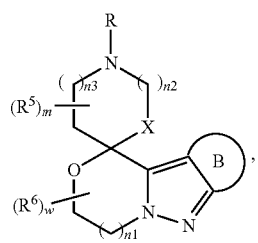

or a pharmaceutically acceptable salt thereof, wherein each of Ring B, m, n1, n2, n3, R, $R^5$, $R^6$, w and X is as described in embodiments for Formula (I), supra, or described in embodiments herein, both singly and in combination.

In some embodiments, a provided compound is a compound of Formula (IV-1):

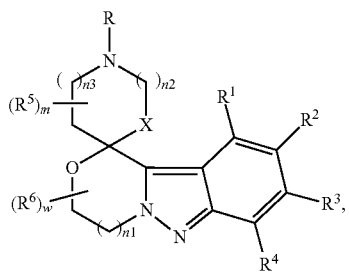

or a pharmaceutically acceptable salt thereof, wherein each of m, n1, n2, n3, R, $R^5$, $R^6$, w and X is as described in embodiments for Formula (I), supra, or described in embodiments herein, both singly and in combination; and each of $R^1$, $R^2$, $R^3$ and $R^4$ is as described in embodiments for Formula (I-1), supra, or described in embodiments herein, both singly and in combination.

In some embodiments, (a) w is 0; (b) each of $R^1$ and $R^4$ is —H; (c) w is 0; and each of $R^1$ and $R^4$ is —H; (d) m is 0; (e) w is 0; each of $R^1$ and $R^4$ is —H; and m is 0; (f) w is 0; each of $R^1$, $R^2$ and $R^4$ is —H; and m is 0; (g) w is 0; each of $R^1$, $R^3$ and $R^4$ is —H; and m is 0; (h) w is 0; each of $R^1$, $R^2$, $R^3$ and $R^4$ is —H; and m is 0; (i) R is —H or —CH$_3$; (j) w is 0; each of $R^1$, $R^2$, $R^3$ and $R^4$ is —H; m is 0; and R is —H or —CH$_3$; (k) each of n2 and n3 is 0; (l) w is 0; each of $R^1$, $R^2$, $R^3$ and $R^4$ is —H; m is 0; R is —H or —CH$_3$; and each of n2 and n3 is 0; (m) one of n2 and n3 is 0 and the other is 1; (n) w is 0; each of $R^1$, $R^2$, $R^3$ and $R^4$ is —H; m is 0; R is —H or —CH$_3$; and one of n2 and n3 is 0 and the other is 1; (o) each of n2 and n3 is 1; or (p) w is 0; each of $R^1$, $R^2$, $R^3$ and $R^4$ is —H; m is 0; R is —H or —CH$_3$; and each of n2 and n3 is 1.

In some embodiments, n1 is 1; and (a) w is 0; (b) each of $R^1$ and $R^4$ is —H; (c) w is 0; and each of $R^1$ and $R^4$ is —H; (d) m is 0; (e) w is 0; each of $R^1$ and $R^4$ is —H; and m is 0; (f) w is 0; each of $R^1$, $R^2$ and $R^4$ is —H; and m is 0; (g) w is 0; each of $R^1$, $R^3$ and $R^4$ is —H; and m is 0; (h) w is 0; each of $R^1$, $R^2$, $R^3$ and $R^4$ is —H; and m is 0; (i) R is —H or —CH$_3$; (j) w is 0; each of $R^1$, $R^2$, $R^3$ and $R^4$ is —H; m is 0; and R is —H or —CH$_3$; (k) each of n2 and n3 is 0; (l) w is 0; each of $R^1$, $R^2$, $R^3$ and $R^4$ is —H; m is 0; R is —H or —CH$_3$; and each of n2 and n3 is 0; (m) one of n2 and n3 is 0 and the other is 1; (n) w is 0; each of $R^1$, $R^2$, $R^3$ and $R^4$ is —H; m is 0; R is —H or —CH$_3$; and one of n2 and n3 is 0 and the other is 1; (o) each of n2 and n3 is 1; or (p) w is 0; each of $R^1$, $R^2$, $R^3$ and $R^4$ is —H; m is 0; R is —H or —CH$_3$; and each of n2 and n3 is 1.

In some embodiments, a provided compound is a compound of Formula (IV-2):

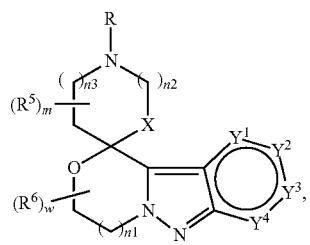

or a pharmaceutically acceptable salt thereof, wherein each of m, n1, n2, n3, R, $R^5$, $R^6$, w and X is as described in embodiments for Formula (I), supra, or described in embodiments herein, both singly and in combination; and each of $Y^1$, $Y^2$, $Y^3$ and $Y^4$ is as described in embodiments for Formula (I-2), supra, or described in embodiments herein, both singly and in combination.

In some embodiments, a provided compound is a compound of Formula (IV-3):

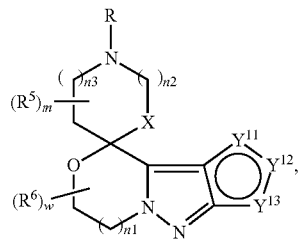

or a pharmaceutically acceptable salt thereof, wherein each of m, n1, n2, n3, R, $R^5$, $R^6$, w and X is as described in embodiments for Formula (I), supra, or described in embodiments herein, both singly and in combination; and each of $Y^{11}$, $Y^{12}$ and $Y^{13}$ is as described in embodiments for Formula (I-3), supra, or described in embodiments herein, both singly and in combination.

Exemplary compounds of formula (I) are set forth in Table 1, below.

TABLE 1

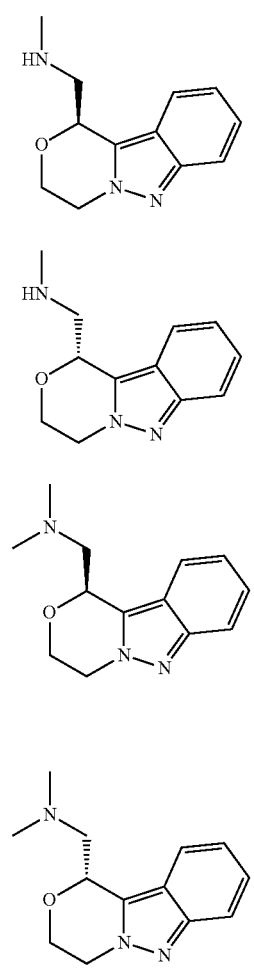

TABLE 1-continued

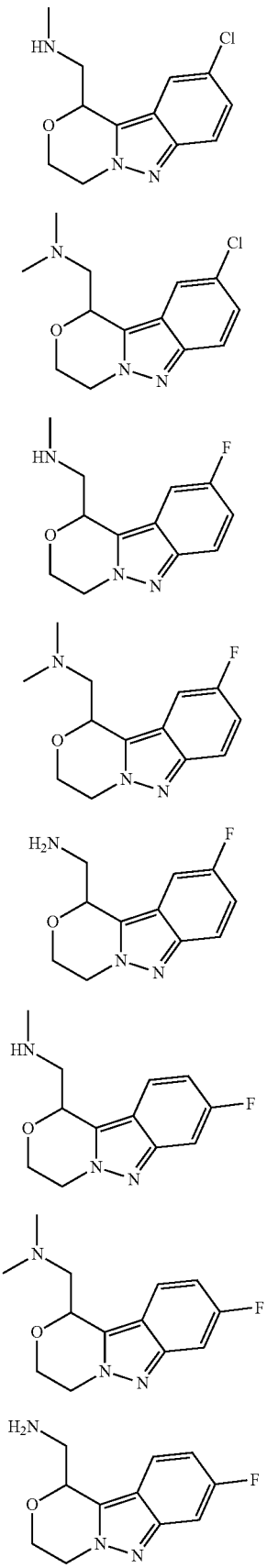

TABLE 1-continued
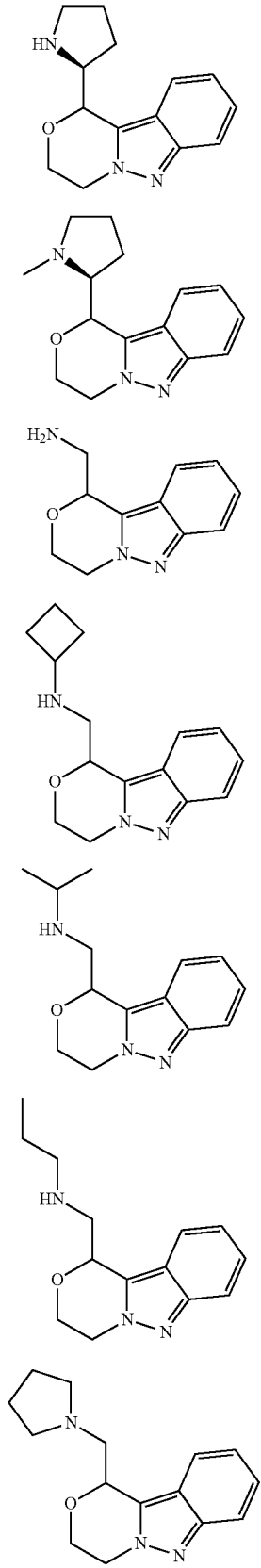
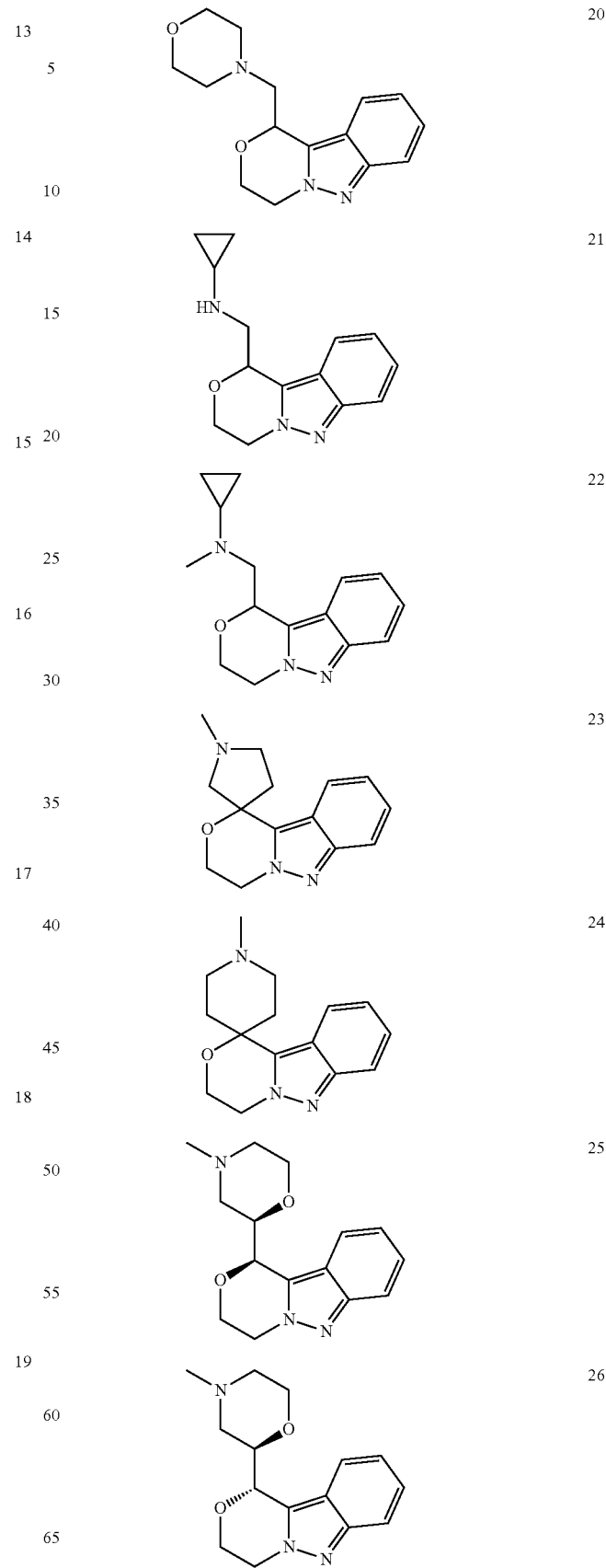

TABLE 1-continued
| | |
|---|---|
| 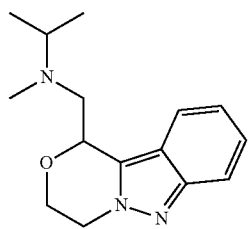 [SMILES: CC(C)N(C)CC1OCCn2nc3ccccc3c21] | 27 |
| 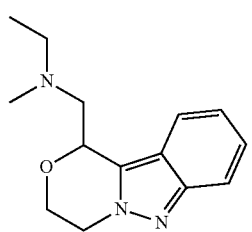 [SMILES: CCN(C)CC1OCCn2nc3ccccc3c21] | 28 |
| 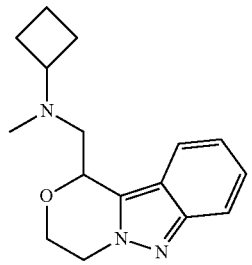 [SMILES: CN(CC1OCCn2nc3ccccc3c21)C1CCC1] | 29 |
| 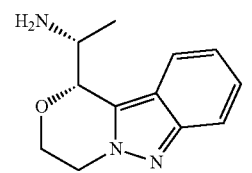 [SMILES: C[C@@H](N)[C@H]1OCCn2nc3ccccc3c21] | 30 |
| 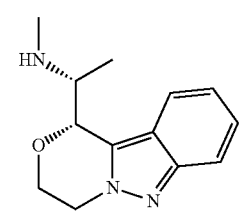 [SMILES: CN[C@H](C)[C@H]1OCCn2nc3ccccc3c21] | 31 |
| 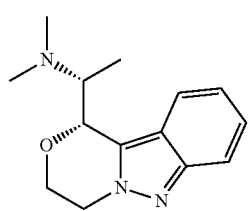 [SMILES: C[C@H]([C@H]1OCCn2nc3ccccc3c21)N(C)C] | 32 |
| 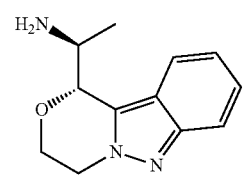 [SMILES: C[C@H](N)[C@H]1OCCn2nc3ccccc3c21] | 33 |
TABLE 1-continued
| | |
|---|---|
| 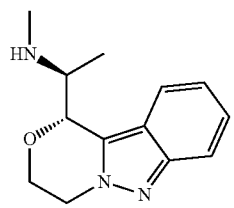 [SMILES: CN[C@@H](C)[C@H]1OCCn2nc3ccccc3c21] | 34 |
| 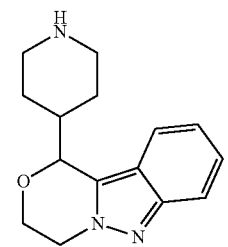 [SMILES: c1ccc2c3n(nc2c1)CCOC3C1CCNCC1] | 35 |
| 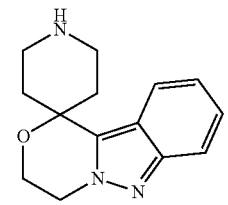 [SMILES: c1ccc2c3n(nc2c1)CCOC31CCNCC1] | 36 |
| 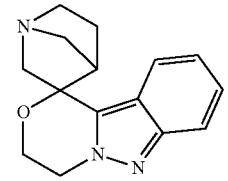 [SMILES: c1ccc2c3n(nc2c1)CCOC31CN2CCC1C2] | 37 |
| 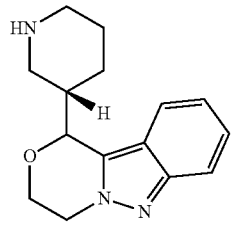 [SMILES: c1ccc2c3n(nc2c1)CCOC3[C@H]1CCCNC1] | 38 |
| 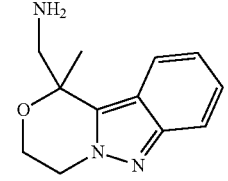 [SMILES: CC1(CN)OCCn2nc3ccccc3c21] | 39 |
| 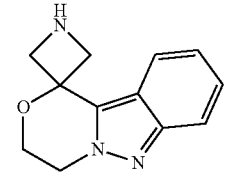 [SMILES: c1ccc2c3n(nc2c1)CCOC31CNC1] | 40 |

TABLE 1-continued
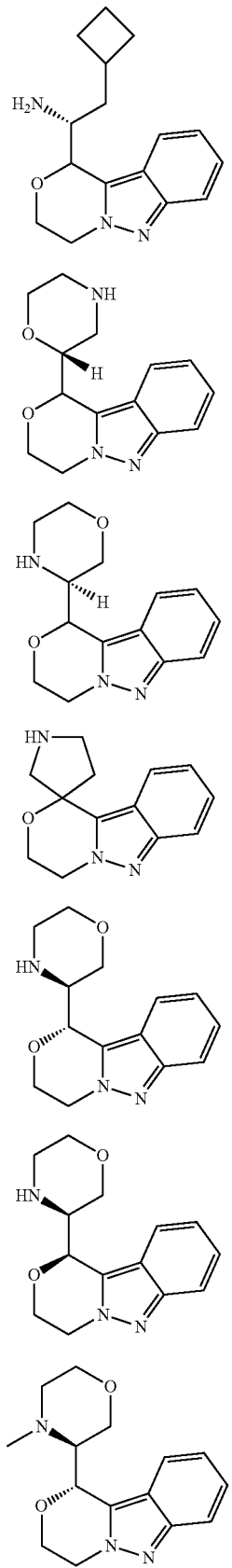
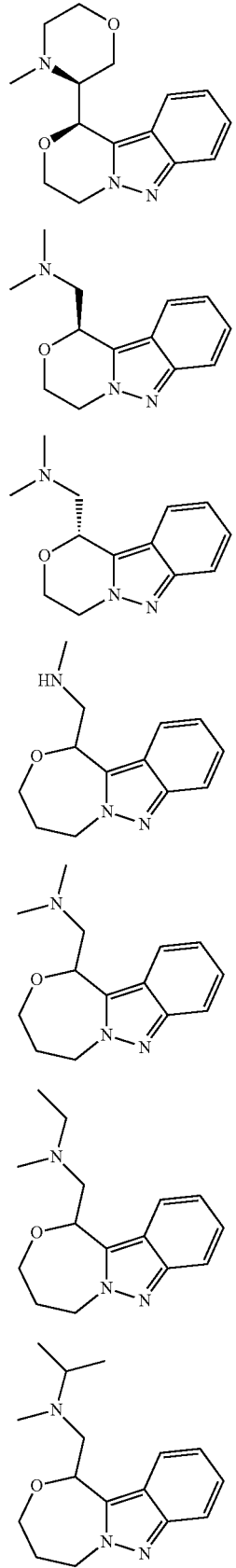

TABLE 1-continued
| | |
|---|---|
| 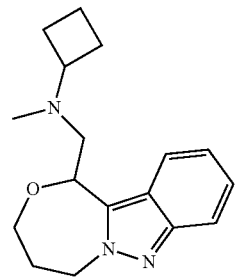 [SMILES: CN(CC1OCCCn2nc3ccccc3c21)C1CCC1] | 55 |
| 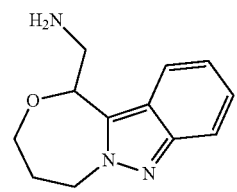 [SMILES: NCC1OCCCn2nc3ccccc3c21] | 56 |
| 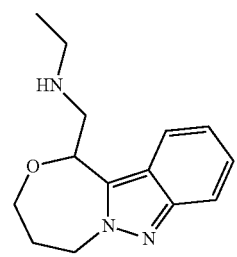 [SMILES: CCNCC1OCCCn2nc3ccccc3c21] | 57 |
| 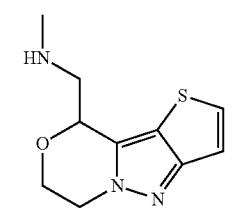 | 58 |
| 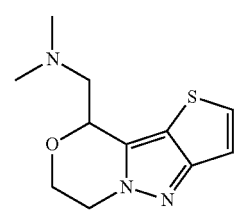 [SMILES: CN(C)CC1OCCn2nc3ccsc3c21] | 59 |
| 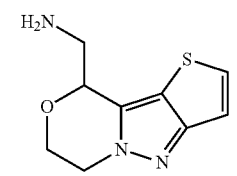 [SMILES: NCC1OCCn2nc3ccsc3c21] | 60 |
| 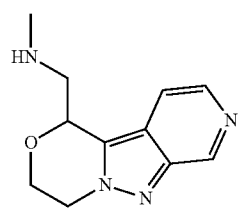 | 61 |
TABLE 1-continued
| | |
|---|---|
| 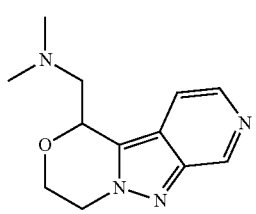 | 62 |
| 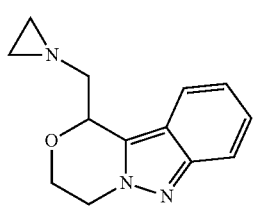 [SMILES: c1ccc2c3n(nc2c1)CCOC3CN1CC1] | 63 |
| 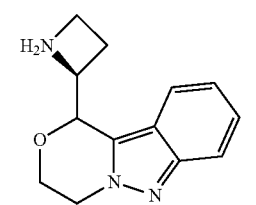 [SMILES: c1ccc2c3n(nc2c1)CCOC3[C@@H]1CCN1] | 64 |
| 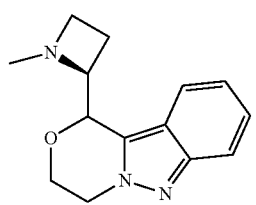 [SMILES: CN1CC[C@H]1C1OCCn2nc3ccccc3c21] | 65 |
| 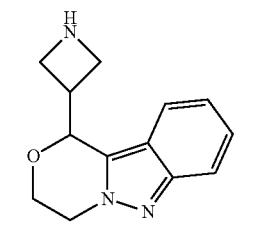 [SMILES: c1ccc2c3n(nc2c1)CCOC3C1CNC1] | 66 |
| 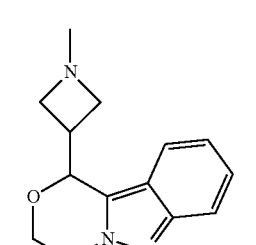 | 67 |
| 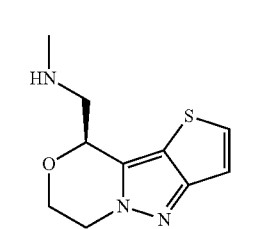 | 68 |

TABLE 1-continued

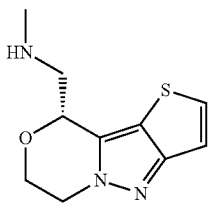

69

In some embodiments, the present invention provides a compound selected from those depicted in Table 1, above, or a pharmaceutically acceptable salt thereof. In some embodiments, the pharmaceutically acceptable salt is a hydrochloride salt.

4. Uses, Formulation and Administration and Pharmaceutically Acceptable Compositions According to another embodiment, the invention provides a composition comprising a compound of this invention, or a pharmaceutically acceptable salt, ester, or salt of ester thereof, and a pharmaceutically acceptable carrier, adjuvant, or vehicle. In some embodiments, the amount of compound in compositions of this invention is such that is effective to treat, prevent, and/or manage various neurological and/or psychiatric disorders and/or symptoms in a patient. In some embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon a variety of factors, including the host treated and the particular mode of administration. Preferably, provided compositions should be formulated so that a dosage of between 0.01-100 mg/kg body weight/day of a compound of the present invention can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

5. Uses of Compounds and Pharmaceutically Acceptable Compositions

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating a neurological or psychiatric disorder.

In some embodiments, the compounds and compositions, according to the method of the present invention, may be administered using any amount and any route of administration effective for treating a neurological and/or psychiatric disorder in a patient.

In some embodiments, the neurological or psychiatric disorder is selected from a psychosis, including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both positive, negative, and cognitive symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Down syndrome, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, Parkinsonism-ALS dementia complex and basal ganglia calcification), medication-induced Parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias {including drug e.g. L-DOPA induced dyskinesia tremor (such as rest tremor, postural tremor, intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia) }; urinary incontinence; neuronal damage including ocular damage, retinopathy or macular degeneration of the eye, tinnitus, hearing impairment and loss, and brain edema; emesis; and sleep disorders including insomnia and narcolepsy.

In some embodiments, the neurological or psychiatric disorder is Alzheimer's Disease, Parkinson's Disease, depression, cognitive impairment, stroke, schizophrenia, Down Syndrome, or Fetal Alcohol Syndrome. In some embodiments, the neurological or psychiatric disorder is Alzheimer's Disease. In some embodiments, the neurological or psychiatric disorder is Parkinson's Disease. In some embodiments, the neurological or psychiatric disorder is depression. In some embodiments, the neurological or psychiatric disorder is cognitive impairment. In some embodiments, the cognitive impairment is cognitive dysfunction associated with depression, for example, major depressive disorder. In some embodiments, the neurological or psychiatric disorder is stroke. In some embodiments, the neurological or psychiatric disorder is schizophrenia. In some embodiments, the neurological or psychiatric disorder is Down Syndrome. In some embodiments, the neurological or psychiatric disorder is Fetal Alcohol Syndrome.

In some embodiments, the neurological or psychiatric disorder involves a deficit in cognition (cognitive domains as defined by the DSM-5 are: complex attention, executive function, learning and memory, language, perceptual-motor, social cognition). In some embodiments, the neurological or psychiatric disorder is associated with a deficit in dopamine signaling. In some embodiments, the neurological or psychiatric disorder is associated with basal ganglia dysfunction. In some embodiments, the neurological or psychiatric disorder is associated with dysregulated locomotor activity. In some embodiments, the neurological or psychiatric disorder is associated with impairment of prefrontal cortex functioning.

In some embodiments, the present invention provides a method of treating one or more symptoms of a neurological and/or psychiatric disorder provided herein. Such disorders include mood disorders, including bipolar I disorder, bipolar II disorder, bipolar depression, mania, cyclothymic disorder, substance/medication-induced bipolar and related disorders, bipolar and related disorder due to another medical condition, other specified bipolar and related disorder, and unspecified bipolar and related disorders; psychotic disorders, including schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), schizoaffective disorder, aggression, delirium, Parkinson's psychosis, excitative psychosis, Tourette's syndrome, and organic or NOS psychosis; depressive disorders, including disruptive mood dysregulation disorder, major depressive disorder (MDD) (including major depressive episode), dysthymia, persistent depressive disorder (dysthymia), treatment resistant depression, premenstrual dysphoric disorder, substance/medication-induced depressive disorder, depressive disorder due to another medical condition, other specified depressive disorder, and unspecified depressive disorder; anxiety disorders, including separation anxiety disorder, selective mutism, specific phobia, social anxiety disorder (social phobia), panic disorder, panic attack specifier, agoraphobia, generalized anxiety disorder, substance/medication-induced anxiety disorder, anxiety disorder due to another medical condition, other specified anxiety disorder, and unspecified anxiety disorder; stressor-related disorders, including reactive attachment disorder, disinhibited social engagement disorder, posttraumatic stress disorder (PTSD), acute stress disorder, and adjustment disorders; and other disorders including substance abuse or dependency (e.g., nicotine, alcohol, cocaine), addiction, eating disorders, behavior disorder, seizure, vertigo, epilepsy, agitation, aggression, neurodegenerative disease, Alzheimer's disease, Parkinson's disease, dyskinesias, Huntington's disease, dementia, premenstrual dysphoria; and attention deficit disorder (ADD) and neurodevelopmental disorders, including attention deficit hyperactivity disorder (ADHD)), autism, autism spectrum disorder, obsessive-compulsive disorder, pain (e.g., neuropathic pain, sensitization accompanying neuropathic pain, and inflammatory pain), fibromyalgia, migraine, cognitive impairment, movement disorder, restless leg syndrome (RLS), multiple sclerosis, Parkinson's disease, Huntington's disease, dyskinesias multiple sclerosis, sleep disorder, sleep apnea, narcolepsy, excessive daytime sleepiness, jet lag, drowsy side effect of medications, insomnia, sexual dysfunction, hypertension, emesis, Lesche-Nyhane disease, Wilson's disease, and Huntington's chorea. In some embodiments, the neurological and/or psychiatric disorders include agitation and aggression. In some embodiments, the agitation and aggression are associated with Alzheimer's Disease, Parkinson's Disease, and/or autism. In some embodiments, the neurological and/or psychiatric disorders are obsessive-compulsive disorder and related disorders (e.g., body dysmorphic disorder, hoarding disorder, trichotillomania, excoriation disorder). In some embodiments, the neurological and/or psychiatric disorders are disruptive, impulse-control, and conduct disorders including oppositional defiant disorder, intermittent explosive disorder, conduct disorder, antisocial personality disorder, pyromania, kleptomania, other specified disruptive, impulse-control, and conduct disorder, unspecified disruptive, impulse-control, and conduct disorder.

In some embodiments, the present invention provides a method of treating one or more symptoms including depression (e.g., major depressive disorder or dysthymia); bipolar disorder, seasonal affective disorder; cognitive deficit; sleep related disorder (e.g., sleep apnea, insomnia, narcolepsy, cataplexy) including those sleep disorders which are produced by psychiatric conditions; chronic fatigue syndrome; anxieties (e.g., general anxiety disorder, social anxiety disorder, panic disorder); obsessive compulsive disorder; postmenopausal vasomotor symptoms (e.g., hot flashes, night sweats); neurodegenerative disease (e.g., Parkinson's disease, Alzheimer's disease and amyotrophic lateral sclerosis); manic disorder; dysthymic disorder; and obesity.

In some embodiments, a depressive disorder is associated with acute suicidality or suicide ideation. The United States Food and Drug Administration has adopted a "black box" label warning indicating that antidepressants may increase the risk of suicidal thinking and behavior in some children, adolescents and young adults (up to age 24) with a depressive disorder such as MDD. In some embodiments, a provided compound does not increase the risk of suicidal thinking and/or behavior in children, adolescents and/or young adults with a depressive disorder, e.g., with MDD. In some embodiments, the present invention provides a method of treating one or more symptoms of a depressive disorder (e.g., MDD) in children, adolescents and/or young adults without increasing the risk of suicidal thinking and/or behavior.

In some embodiments, the present invention provides a method of treating one or more symptoms including senile dementia, Alzheimer's type dementia, cognition, memory loss, amnesia/amnestic syndrome, disturbances of consciousness, coma, lowering of attention, speech disorder, Lennox syndrome, and hyperkinetic syndrome.

In some embodiments, the present invention provides a method of treating one or more symptoms of neuropathic pain, including post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

In some embodiments, the present invention provides a method of treating one or more symptoms including obesity; migraine or migraine headache; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

In some embodiments, the present invention provides a method of suppressing rapid eye movement (REM) during both sleep and daytime equivalent.

In some embodiments, the present invention provides a method of suppressing or eliminating pathological or excessive REM during the night or daytime equivalent.

In some embodiments, the present invention provides a method of treating one or more symptoms including cataplexy (sudden involuntary transient bouts of muscle weakness or paralysis while awake); nighttime sleep disturbance/sleep fragmentation associated with narcolepsy or other conditions; sleep paralysis associated with narcolepsy or other conditions; hypnagogic and hypnapompic hallucinations associated with narcolepsy or other conditions; and excessive daytime sleepiness associated with narcolepsy, sleep apnea or shift work disorder and other medical conditions such as cancer, chronic fatigue syndrome and fibromyalgia.

In some embodiments, the present invention provides a method of treating a neurological and/or psychiatric disorder described herein, comprising administering a compound of the invention in conjunction with one or more pharmaceutical agents. Suitable pharmaceutical agents that may be used in combination with the compounds of the present invention include anti-Parkinson's drugs, anti-Alzheimer's drugs, anti-depressants, anti-psychotics, anti-ischemics, CNS depressants, anti-cholinergics, and nootropics. In some embodiments, suitable pharmaceutical agents are anxiolytics.

Suitable anti-Parkinson's drugs include dopamine replacement therapy (e.g. L-DOPA, carbidopa, COMT inhibitors such as entacapone), dopamine agonists (e.g. D1 agonists, D2 agonists, mixed D1/D2 agonists; bromocriptine, pergolide, cabergoline, ropinirole, pramipexole, or apomorphine in combination with domperidone), histamine H2 antagonists, and monoamine oxidase inhibitors such as selegiline and tranylcypromine.

In some embodiments, compounds of the invention can be used in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone, MAO A/B inhibitors, antioxidants, Ata adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexole are commonly used in a non-salt form.

Suitable anti-Alzheimer's drugs include beta-secretase inhibitors, gamma-secretase inhibitors, HMG-CoA reductase inhibitors, NSAID's including ibuprofen, vitamin E, and anti-amyloid antibodies. In some embodiments, an anti-Alzheimer's drug is memantine.

Suitable anti-depressants and anti-anxiety agents include norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists.

Specific suitable anti-depressant and anti-anxiety agents include amitriptyline, clomipramine, doxepin, imipramine and trimipramine; amoxapine, desipramine, citalopram, escitalopram, maprotiline, nortriptyline and protriptyline; fluoxetine, fluvoxamine, paroxetine and sertraline; isocarboxazid, phenelzine, tranylcypromine and selegiline; moclobemide: venlafaxine; desvenlafaxine, duloxetine; aprepitant; bupropion, vilazodone, mirtazapine, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof. In some embodiments, suitable anti-depressant and anti-anxiety agents are tianeptine, or pharmaceutically acceptable salts thereof.

Suitable anti-psychotic and mood stabilizer agents include D2 antagonists, 5HT2A antagonists, atypical antipsychotics, lithium, and anticonvulsants.

Specific suitable anti-psychotic and mood stabilizer agents include chlorpromazine, fluphenazine, haloperidol, amisulpride, chlorpromazine, perphenazine, thioridazine, trifluoperazine, aripiprazole, asenapine, clozapine, olanzapine, paliperidone, quetiapine, risperidone, ziprasidone, lurasidone, flupentixol, levomepromazine, pericyazine, perphenazine, pimozide, prochlorperazine, zuclopenthixol, olanzapine and fluoxetine, lithium, carbamazepine, lamotrigine, valproic acid and pharmaceutically acceptable salts thereof.

In some embodiments, compounds of the invention may be used in combination with other therapies. Suitable therapies include psychotherapy, cognitive behavioral therapy, electroconvulsive therapy, transcranial magnetic stimulation, vagus nerve stimulation, and deep-brain stimulation.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In some embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In some embodiments, a combination of 2 or more therapeutic agents may be administered together with the compounds of the invention. In some embodiments, a combination of 3 or more therapeutic agents may be administered with the compounds of the invention.

Other examples of agents the compounds of this invention may also be combined with include: vitamins and nutritional supplements, antiemetics (e.g. 5-HT3 receptor antagonists, dopamine antagonists, NK1 receptor antagonists, histamine receptor antagonists, cannabinoids, benzodiazepines, or anticholinergics), agents for treating Multiple Sclerosis (MS) such as beta interferon (e.g., Avonex® and Rebif®), Copaxone®, and mitoxantrone; treatments for asthma such as albuterol and Singulair®; anti-inflammatory agents such as corticosteroids, TNF blockers, IL-1 RA, azathioprine, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In some embodiments, a compound of the present invention, or a pharmaceutically acceptable salt thereof, is administered in combination with an antisense agent, a monoclonal or polyclonal antibody, or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, or a pharmaceutically acceptable salt thereof, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the present invention provides a medicament comprising at least one compound of formula I, or a pharmaceutically acceptable salt thereof, and a pharmaceutically acceptable carrier, adjuvant, or vehicle.

In some embodiments, the present invention provides the use of a compound of formula I, or a pharmaceutically acceptable salt thereof, in the manufacture of a medicament for the treatment of a neurological and/or psychiatric disorder.

EXAMPLES

Example 1. Compounds

As depicted in the Examples below, in some embodiments, compounds are prepared according to the following procedures. It will be appreciated that, although the general methods depict the synthesis of certain compounds of the present invention, the following methods, and other methods known to persons skilled in the art, can be applied to all compounds and subclasses and species of each of these, as described herein.

Example 1.A. Preparation of 2-(2H-indazol-2-yl)ethanol (I-2)

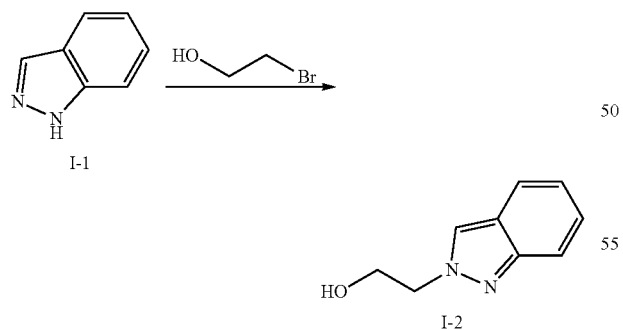

A mixture of 1H-indazole (100 g 847 mmol) in 2-bromoethanol (420 g 3.39 mol) was stirred at 140° C. for 3 hour. The mixture was cooled and concentrated. The residue was purified by flash column chromatography on silica gel (ethyl acetate in petroleum ether, 1/4 $^v/_v$) to give the desired product intermediate I-2 (120 g, 87%); MS (ESI): m/z 163 [M+H]$^+$.

Example 1.B. Preparation of tert-butyl 2-hydroxy-2-(2-(2-hydroxyethyl)-2H-indazol-3-yl)ethyl (methyl)carbamate (I-3)

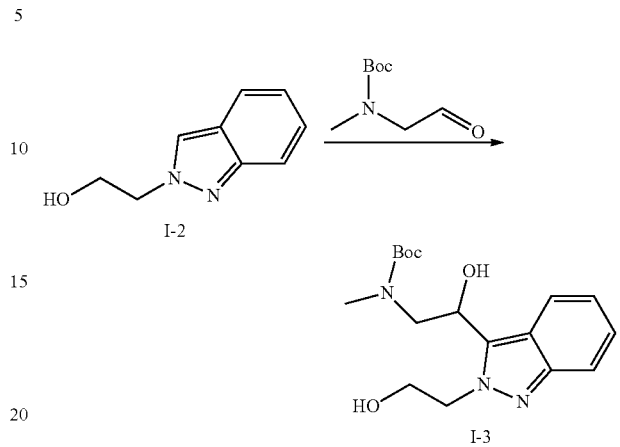

To a solution of intermediate I-2 (60 g, 0.37 mol) in THF (300 mL) at −78° C., LDA (296 mL, 2.5M, 0.74 mol) was added dropwise over 40 minutes keeping the temperature below −78° C. the solution was allowed to come to −15° C. when after tert-butyl methyl(2-oxoethyl)carbamate (128 g, 0.74 mol) in THF (100 mL) was added dropwise over 20 minutes keeping the temperature below −78° C. The mixture was allowed to come to rt overnight and poured into ice water, extracted with ethyl acetate (3×250 mL). The combined organic layers were washed with brine (2×200 mL), dried over sodium sulfate and concentrated. The crude intermediate I-3 was used in next step without purification (120 g, 65%); MS (ESI): m/z 336 [M+H]$^+$.

Example 1.C. Preparation of (3,4-dihydro-1H-[1,4]oxazino[4,3-b]indazol-1-yl)-N-methylmethanamine (I-4)

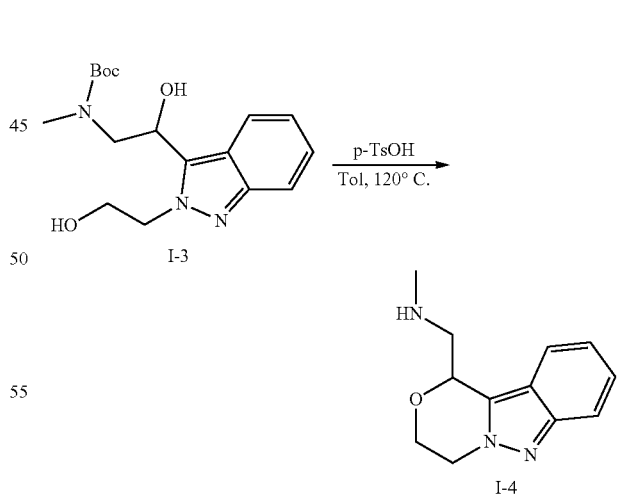

To a solution of intermediate I-3 (120 g, 358 mmol) in toluene (400 mL) was added 4-methylbenzenesulfonic acid (123 g, 716 mmol), The reaction was stirred at 0° C. for 3 h, then stirred at 120° C. for 16 hrs. Upon the completion, the mixture was washed with water (3×200 mL), then concentrated and purified by column chromatography (Dichloromethane:methanol=1:20) to give intermediate I-4 (26 g, 33%) as a yellow oil. MS (ESI): m/z 218 [M+H]$^+$; 1H NMR (400 MHz, CDCl3) δ 7.68-7.65 (m, 1H), 7.56-7.54 (m, 1H), 7.29-7.26 (m, 1H), 7.06-7.02 (m, 1H), 5.29-5.27 (m, 1H), 4.53-4.50 (m, 1H), 4.43-4.36 (m, 2H), 4.07-4.02 (m, 1H), 3.35-3.31 (m, 1H), 3.14-3.09 (m, 1H), 2.51 (s, 3H).

Example 1.D. Preparation of (tert-butyl (3,4-dihydro-1H-[1,4]oxazino[4,3-b]indazol-1-yl)methyl (methyl)carbamate (I-5)

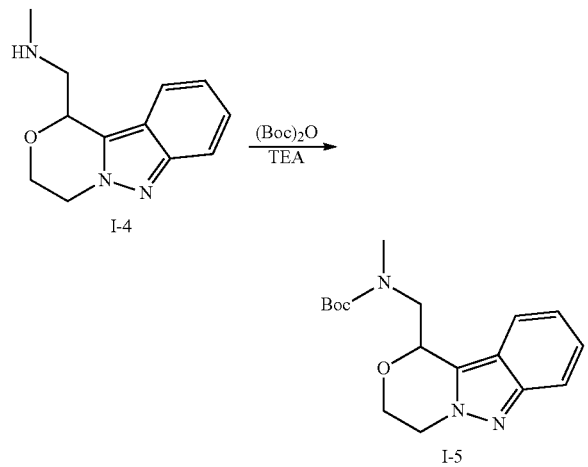

To a solution of intermediate I-4 (26 g, 120 mmol) in dichloromethane (250 mL) was added triethylamine (24.2 g, 240 mmol) and di-cert-butyl dicarbonate (52.3 g, 240 mmol) at 0° C., the reaction was stirred at 0° C. for 3 h, then stirred at room temperature for 16 hrs. The mixture was washed with water (3×200 mL), then concentrated and purified by column chromatography (ethyl acetate/petroleum ether=1:20) to give intermediate I-5 (32 g, 80%) as a white solid. MS (ESI): m/z 280 [M-56+H]$^+$.

Example 1.E. Preparation of tert-butyl (R)-((3,4-dihydro-1H-[1,4]oxazino[4,3-b]indazol-1-yl)methyl) (methyl)carbamate (I-6) and tert-butyl (S)-((3,4-dihydro-1H-[1,4]oxazino[4,3-b]indazol-1-yl)methyl) (methyl)carbamate (I-7)

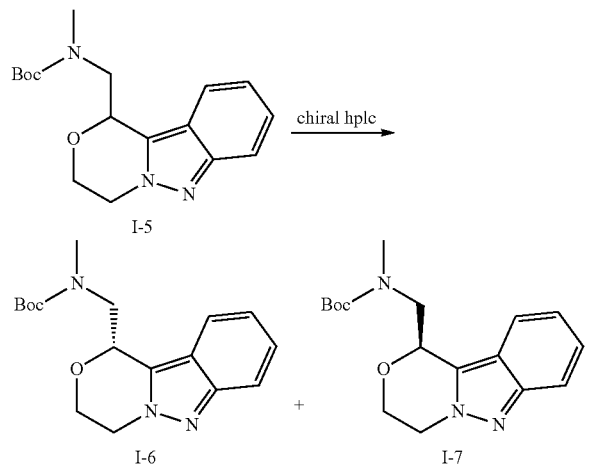

Intermediate I-5 (17 g, 50.7 mmol) was separated into its enantiomers I-6 and I-7 by chiral HPLC using column CHIRALPAK IC 30*250 mm 5 μm (Daicel) and mobile phase CO$_2$/methanol=70/30. The flow rate was 160 g/min, back pressure was 100 Bar and cycle time of stack injections was 4.2 min. Intermediate I-6 (7.0 g, 41%, retention time 3.96 min) was obtained as yellow oil and intermediate I-7 (6.5 g, 38%, retention time 4.56 min) was obtained as yellow oil.

Example 1.F. Preparation of 5-8 (S)-(3,4-dihydro-1H-[1,4]oxazino[4,3-b]indazol-1-yl)-N,N-dimethyl-methanamine (I-8)

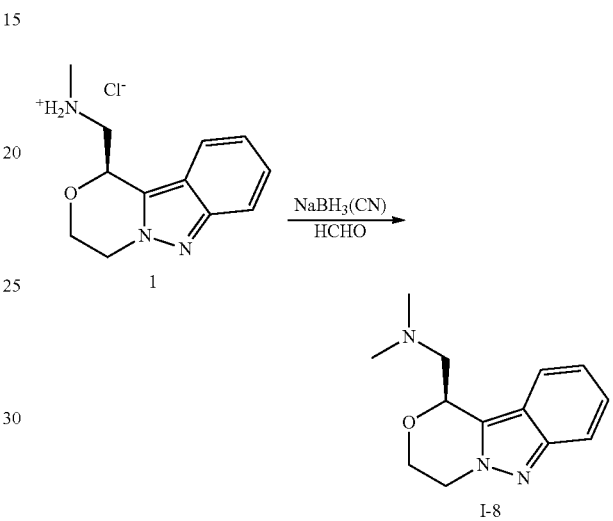

To a solution of compound 1 (1.2 g, 4.74 mmol) in methanol (100 mL) was added paraformaldehyde (284.4 mg, 9.48 mmol) and NaBH$_3$CN (597.2 mg, 9.48 mmol) and the mixture was stirred at 40° C. for 2 hours, water (100 mL) was added, extracted with dichloromethane (3×100 mL), combined, dried and then purified by preparative HPLC in 0.01% ammonia to give intermediate I-8 (1.01 g, 92%); MS (ESI): m/z 232 [M+H]$^+$; 1H NMR (400 MHz, CDCl3) δ 7.67 (d, J=8.8 Hz, 1H), 7.61 (d, J=8.8 Hz, 1H), 7.31-7.27 (m, 1H), 7.07-7.04 (m, 1H), 5.32-5.29 (m, 1H), 4.57-4.51 (m, 1H), 4.45-4.39 (m, 2H), 4.08-4.02 (m, 1H), 3.04-3.00 (m, 1H), 2.91-2.85 (m, 1H), 2.44 (s, 6H).

Example 1.G. Preparation of 5-chloro-2H-indazole (I-10)

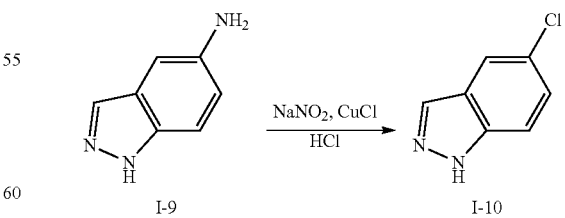

5-amino-1H-indazole I-9 (15.41 g, 116 mmol) was suspended in a mixture of water (250 mL), ice (250 g), and concentrated HCl (100 mL). The mixture was cooled in an ice-salt bath to an internal temperature of −5° C. To this mixture was added a solution of sodium nitrite (8.78 g, 127 mmol) in water (75 mL), which had been cooled to 0° C. The resulting diazonium solution was stirred for 15 minutes at −5° C. A solution of copper (I) chloride (14.9 g, 151 mmol) in concentrated HCl (150 mL) was cooled to 0° C. and then added to the diazonium solution dropwise, causing an orange precipitate to form. The cooling bath was removed to allow the reaction to warm to room temperature. Gas evolution began at 10° C. internal temperature. After stirring at room temperature for 1.5 hours, the gas evolution subsided. The flask was then heated to 60° C. for 30 minutes, cooled to ~15° C. while a brown precipitate formed. The precipitate was collected by suction filtration and dried in a vacuum desiccator over sodium hydroxide for 16 hours to give crude intermediate I-10 (25.6 g) as a tan powder that was purified via silicagel chromatography, eluting with dichloromethane: methanol 20:1 to give intermediate I-10 (8.0 g, 45%); MS (ESI): m/z 153 [M+H]+.

Example 1.H. Preparation of 2-(5-chloro-2H-indazol-2-yl)ethanol (I-11)

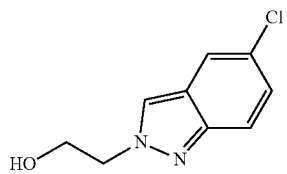

I-11

Intermediate I-11 was prepared using a procedure analogous to that described for intermediate I-2, but using intermediate I-10 in place of intermediate I-1 in the procedure of Example 1.A. (5.4 g, white solid, 55%); MS (ESI): m/z 197 [M+H]+.

Example 1.I. Preparation of tert-butyl (2-(5-chloro-2-(2-hydroxyethyl)-2H-indazol-3-yl)-2-hydroxyethyl)(methyl)carbamate (I-12)

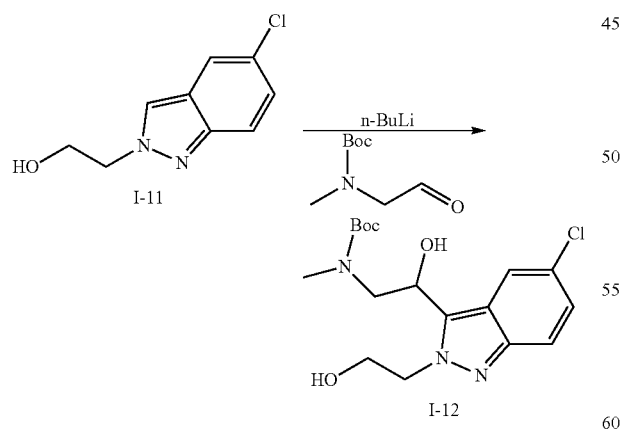

A solution of 2.5 M butyllithium in hexane (5.4 mL, 13.53 mmol) was added to a solution of intermediate I-11 (1.21 g, 6.15 mmol) in tetrahydrofuran (15 mL) at −78° C. The solution was stirred at −78° C. for 30 min and then tert-butyl methyl(2-oxoethyl)carbamate (2.13 g, 12.13 mmol) was added, the reaction mixture was warmed slowly to room temperature. After stirring for 2 h, H₂O (15 mL) was added, the water phase was extracted by ethyl acetate (30 mL) twice, the organic phase was washed by brine and dried over Na₂SO₄, the solvent was removed in vacuo and the residue was purified by reverse-phase column chromatography to give intermediate I-12 (880 mg black oil, purity: 62%, 214 nm, 24%) that was used in the following step without further purification. MS (ESI): m/z 370 [M+H]+.

Example 1.J. Preparation of 1-(9-chloro-3,4-dihydro-1H-[1,4]oxazino[4,3-b]indazol-1-yl)-N-methylmethanamine (I-13)

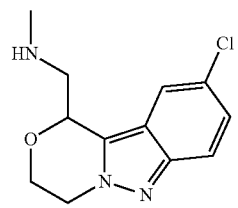

I-13

Intermediate I-13 was prepared using a procedure analogous to that described for intermediate I-4, but using intermediate I-12 in place of intermediate I-3 in the procedure of Example 1.C. as the starting material. (435 mg, colorless oil), MS (ESI): m/z 252 [M+H]+. ¹H-NMR (400 MHz, CDCl₃): δ 7.60 (d, J=9.4 Hz, 1H), 7.55 (d, J=1.5 Hz, 1H), 7.24-7.18 (m, 1H), 5.23 (dd, J=7.9, 2.9 Hz, 1H), 4.58-4.47 (m, 1H), 4.45-4.36 (m, 2H), 4.06 (ddd, J=12.0, 9.8, 3.6 Hz, 1H), 3.28 (dd, J=13.0, 3.1 Hz, 1H), 3.10 (dd, J=12.8, 8.0 Hz, 1H), 2.53 (s, 3H).

Example 1.K. Preparation of 1-(9-chloro-3,4-dihydro-1H-[1,4]oxazino[4,3-b]indazol-1-yl)-N,N-dimethylmethanamine (I-14)

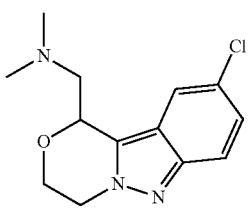

I-14

Intermediate I-14 was prepared using a procedure analogous to that described for intermediate I-8, but using compound 5 in place of compound 1 in the procedure of Example 1.F. as the starting material. (120 mg, white solid); MS (ESI): m/z 265 [M+H]+; ¹H-NMR (400 MHz, CDCl₃): δ 7.60 (d, J=9.4 Hz, 2H), 7.21 (dd, J=9.1, 2.0 Hz, 1H), 5.24 (dd, J=8.3, 3.4 Hz, 1H), 4.58-4.48 (m, 1H), 4.42 (td, J=5.3, 2.7 Hz, 2H), 4.10-4.01 (m, 1H), 2.95 (dd, J=13.4, 3.6 Hz, 1H), 2.86 (dd, J=13.4, 8.4 Hz, 1H), 2.44 (s, 6H).

Example 1.L. Preparation of 5-fluoro-2-(2-hydroxyethyl)-2H-indazole-3-carbaldehyde (I-16)

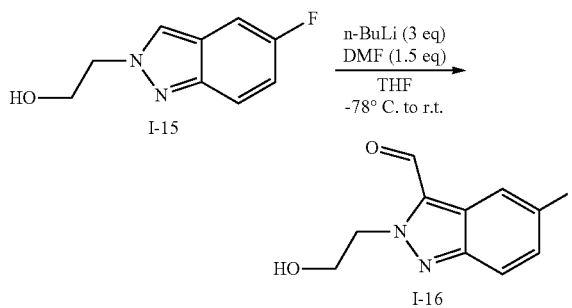

To a solution of intermediate I-15 (1.9 g, 10.6 mmol, prepared using a procedure analogous to that described for intermediate I-2, but using 5-fluoro-1H-indazole in place of intermediate I-1 in the procedure of Example 1.A. in tetrahydrofuran (100 mL) at −78° C., n-butyllithium (13.2 mL, 31.7 mmol) was added dropwise. The resulting mixture was stirred at −78° C. for 30 min then warmed to −20° C. for 0.5 h and a solution of N,N-dimethylformamide (1.15 g, 15.9 mmol) in tetrahydrofuran (5 mL) was added dropwise. The resulting mixture was stirred at −78° C. for 1 h. Upon the completion, the reaction mixture was neutralized with saturated ammonium chloride solution and extracted with ethyl acetate (3×100 mL). The combined organic layers were washed with brine (200 mL), the solvent was removed to give intermediate I-16 (2.2 g) as a yellow oil that was used in the following step without further purification. MS (ESI): m/z 209 [M+H]+.

Example 1.M. Preparation of 9-fluoro-1-methoxy-3,4-dihydro-1H-[1,4]oxazino[4,3-b]indazole (I-17)

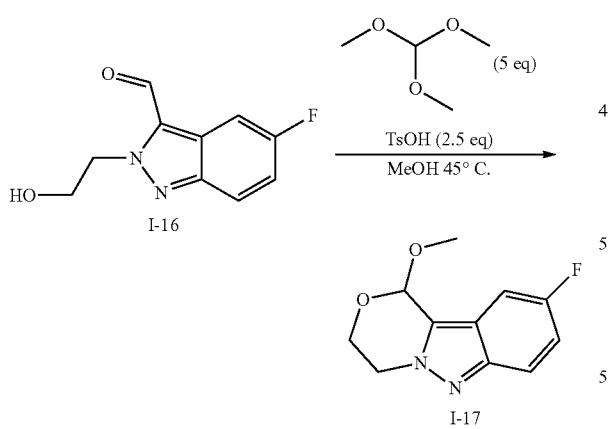

To a solution of intermediate I-16 (2.2 g, 10.6 mmol) and trimethoxymethane (5.6 g, 53.0 mmol) in methanol (50 mL), p-toluenesulfonic acid (5.0 g, 26.5 mmol) was added in portions. The resulting mixture was stirred at 45° C. for 1.5 h. Upon the completion, the reaction mixture was neutralized with saturated sodium bicarbonate solution and extracted with dichloromethane (3×80 mL). The combined organic layers were washed with brine (150 mL), dried over sodium sulfate and concentrated and purified by flash column chromatography on silica gel (dichloromethane/petroleum ether, 1/1 v/v) to give the desired product intermediate I-17 (1.4 g, 60%) as a yellow oil. MS (ESI): m/z 223 [M+H]+.

Example 1.N. Preparation of 9-fluoro-3,4-dihydro-1H-[1,4]oxazino[4,3-b]indazole-1-carbonitrile (I-18)

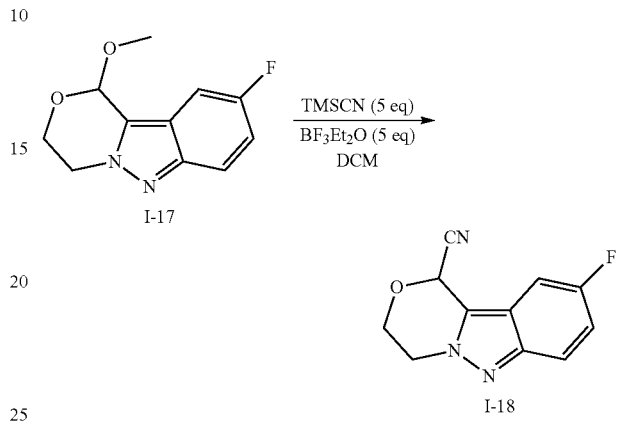

To a solution of intermediate I-17 (1.4 g, 6.3 mmol) and trimethylsilycyanide (3.9 ml, 31.5 mmol) in dichloromethane (50 mL) at −78° C. boron trifluoride etherate (3.9 ml, 31.5 mmol) was added dropwise over the course of 10 min. The resulting mixture was stirred at 30° C. for 1.5 h. Upon the completion, the reaction mixture was neutralized with saturated sodium bicarbonate solution, extracted with dichloromethane (3×60 mL). The combined organic layers were washed with brine (100 mL), dried over sodium sulfate, concentrated and purified by flash column chromatography on silica gel (dichloromethane/methanol, 100/5 v/v) to give intermediate I-18 (0.40 g, 29%) as a yellow solid. MS (ESI): m/z 218 [M+H]+.

Example 1.O. Preparation of (9-fluoro-3,4-dihydro-1H-[1,4]oxazino[4,3-b]indazol-1-yl)methanamine (I-19)

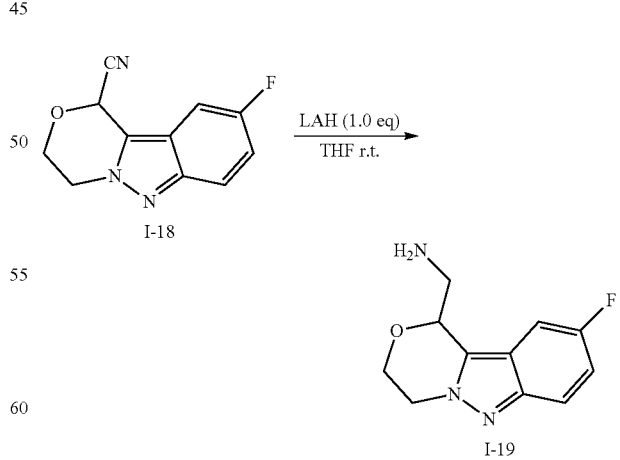

To a solution of intermediate I-18 (0.40 g, 1.84 mmol) in tetrahydrofuran (20 mL) was added lithium tetrahydridoaluminate (0.11 g, 2.76 mmol). The mixture was stirred at 0° C. for 10 minutes and warmed to room temperature, the mixture was stirred at room temperature for 0.5 hour. After completion, the reaction was quenched with water (30 mL), diluted with dichloromethane (3×30 mL) and washed with brine (3×30 mL), dried over sodium sulfate, filtered and concentrated in vacuo to give crude intermediate I-19 (0.3 g, yellow oil) that was used in the following step without further purification. MS (ESI): m/z 222 [M+H]$^+$.

Example 1.P. Preparation of tert-butyl (9-fluoro-3, 4-dihydro-1H-[1,4]oxazino[4,3-b]indazol-1-yl)methylcarbamate (I-20)

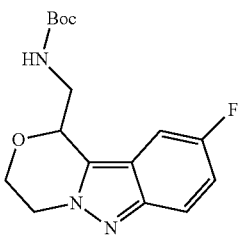

Intermediate I-20 was prepared using a procedure analogous to that described for intermediate I-5, but using intermediate I-19 in place of intermediate I-4 in the procedure of Example 1.D. (0.20 g, yellow oil); MS (ESI): m/z 322 [M+H]$^+$.

Example 1.Q. Preparation of tert-butyl ((3,4-dihydro-1H-[1,4]oxazino[4,3-b]indazol-1-yl) methyl) (ethyl)carbamate (I-22)

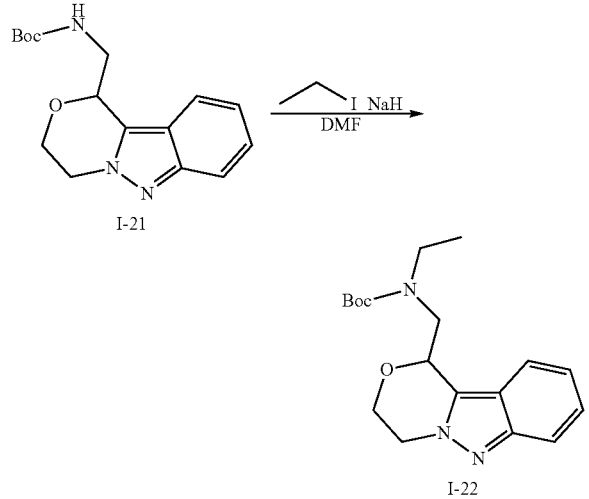

To a solution of intermediate I-21 (319 mg, 1.05 mmol, prepared using a procedure analogous to that described for intermediate I-20 but using intermediate I-2 in place of intermediate I-15 in the procedure of Example 1.L) in N,N-dimethyllformamide (10 mL) was added sodium hydride (60% in oil, 63 mg, 1.58 mmol) at 0° C. The reaction was stirred at 0° C. for 1 hour. Iodoethane (164 mg, 1.05 mmol) was added. The reaction was stirred at ambient temperature for 3 hours. Saturated aqueous sodium bicarbonate (50 mL) and ethyl acetate (60 mL) were added and the organic phase was washed with water (2×30 mL) and brine (3×60 mL). The combined organics were dried over anhydrous sodium sulfate, filtered and concentrated in vacuo to give intermediate I-22 (256 mg, amber oil, 74%) that was used in the following step without further purification. MS (ESI): m/z 332 [M+H]$^+$.

Example 1.R. Preparation of 1-(2-(2-hydroxyethyl)-2H-indazol-3-yl)ethanone (I-23)

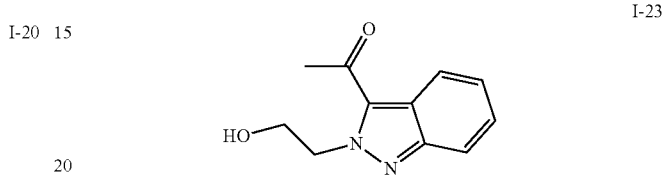

Intermediate I-23 was prepared using a procedure analogous to that described for intermediate I-12, but using intermediate I-2 in place of intermediate I-11 and ethyl acetatein place of tert-butyl methyl(2-oxoethyl)carbamate in the procedure of Example 1.I. (6.1 g, brown oil); MS (ESI): m/z 205 [M+H]$^+$.

Example 1.S. Preparation of 2-(3-acetyl-2H-indazol-2-yl)ethyl acetate (I-24)

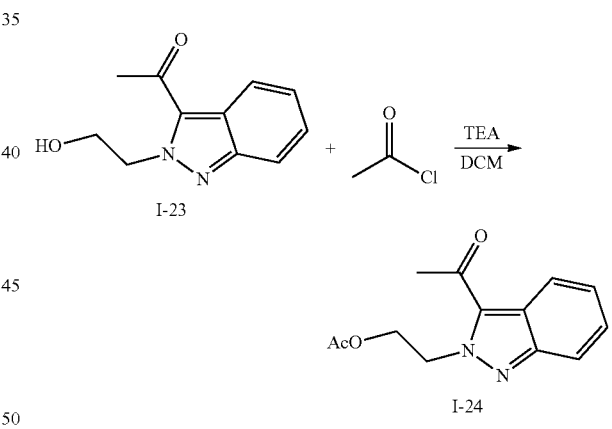

To a solution of intermediate I-23 (6.1 g, 29.87 mmol) in dichloromethane (200.0 mL) was added acetyl chloride (1.88 g, 23.9 mmol) in one portion at room temperature. To reaction mixture was added triethylamine (3.02 g, 29.87 mmol) dropwise under nitrogen at 0° C. over 15 min. The reaction mixture was stirred for 1.0 h at room temperature. The reaction mixture was quenched with sodium hydrogen carbonate aqueous solution (50 mL). The aqueous phase was extracted with dichloromethane (50 mL×3). The combined organic phase was washed with brine (70 mL×3) and dried over sodium sulphate and concentrated under reduced pressure to afford the crude product which was purified through silica gel. (Petroleum ether:ethyl acetate=5:1) to give intermediate I-24 (0.9 g 31%) as a brown oil. MS (ESI): m/z 247 [M+H]$^+$.

Example 1.T. Preparation of 2-(3-(2-bromoacetyl)-2H-indazol-2-yl)ethyl acetate (I-25)

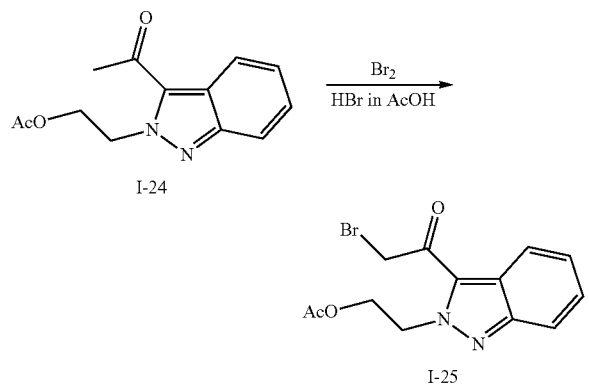

To a solution of intermediate I-24 (0.72 g, 2.92 mmol) in a mixture of glacial acetic acid (2.5 mL) and HBr/glacial acetic acid (2.5 mL) was added bromine (0.51 g, 3.21 mmol) dropwise under nitrogen at 0° C. over 10 min and the reaction mixture was stirred at 40° C. for 1.0 h. The reaction mixture was poured into 150 g of ice and neutralized with solid sodium carbonate to pH=7. The aqueous phase was extracted with dichloromethane (50 mL×3). The combined organic phase was washed with brine (50 mL×3), dried over sodium sulphate and concentrated under reduced pressure to afford intermediate I-25 (0.95 g, 100%) as a brown solid. MS (ESI): m/z 325, 327 [M+H]$^+$.

Example 1.U. Preparation of 1-((3,4-dihydro-1H-[1,4]oxazino[4,3-b]indazol-1-yl)methyl)pyrrolidin-1-ium chloride (I-26)

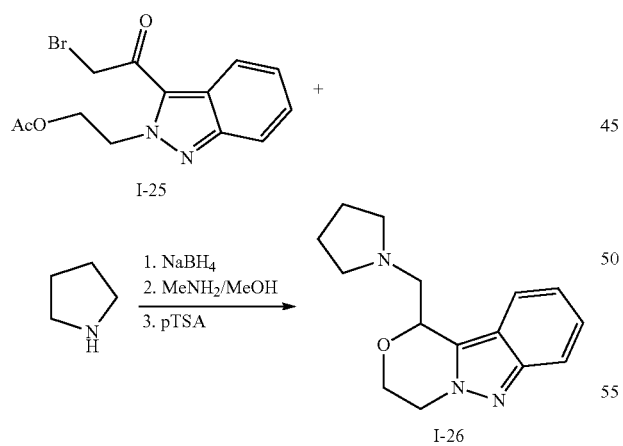

To a solution of intermediate I-25 (0.652 g, 2.00 mmol) in acetonitrile (50 mL) was added pyrrolidine (4.9 ml, 60.0 mmol) dropwise at −50° C. and the reaction mixture was stirred at room temperature for 2.0 h and then diluted with 25 mL of methanol. To the reaction mixture was added sodium borohydride (0.304 g, 8.0 mmol) portion wise at room temperature. After 1.0 h, the reaction mixture was quenched with 50.0 mL of sat. NH$_4$Cl solution and the crude reaction mixture was concentrated under reduced pressure. The residue was dissolved in ethyl acetate (150 mL), washed with brine (50 mL×3), the organic phase was dried over sodium sulphate, the solids were removed by filtration and the filtrate was concentrated under reduced pressure. The residue was dissolved in a solution of methylamine in methanol (40.0 mL, 30%) at room temperature and the solution was stirred at 70° C. for 3.0 h. The reaction mixture was concentrated under reduced pressure. 4-methyl benzenesulfonic acid (1.548 g, 9.0 mmol) was added to the solution of the residue in toluene (35.0 mL) in one portion at room temperature and the reaction mixture was stirred at reflux for 16 hrs. The reaction mixture was poured into saturated sodium carbonate aqueous solution (80.0 mL). The resulted mixture was extracted with ethyl acetate (80.0 mL×3). The organic phase was washed with brine (70.0 mL×3) and concentrated under reduced pressure to afford the crude product which was purified through silica gel. (Dichloromethane:methanol=30:1) to give intermediate I-26 (87 mg, 17%) as a brown solid. MS (ESI): m/z 258 [M+H]$^+$.

Example 1.V. Preparation of 3,4-dihydrospiro[[1,4]oxazino[4,3-b]indazole-1,3'-pyrrolidin]-1'-ium chloride (I-27)

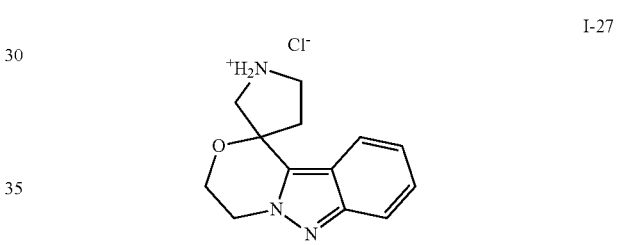

Intermediate I-27 was prepared using a procedure analogous to that described for compound 5 but using intermediate I-2 in place of intermediate I-11 and tert-butyl 3-oxopyrrolidine-1-carboxylate in place of tert-butyl methyl(2-oxoethyl)carbamate in the procedure of Example 1.1 (740 mg, 91%) as a white solid. MS (ESI): m/z 230 [M+H]$^+$.

Example 1.W. Preparation of (R)-1-((R)-4-methylmorpholin-2-yl)-3,4-dihydro-1H-[1,4]oxazino[4,3-b]indazole (I-29) and (S)-1-((R)-4-methylmorpholin-2-yl)-3,4-dihydro-1H-[1,4]oxazino[4,3-b]indazole (I-30)

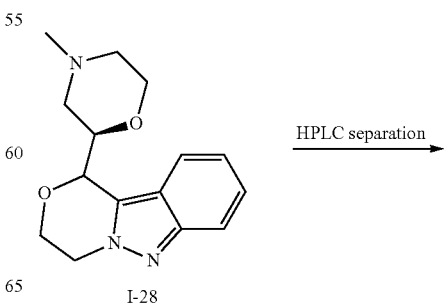

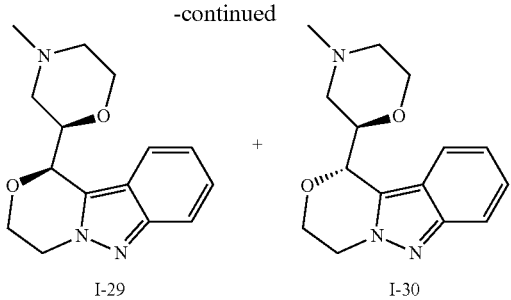

Intermediate I-28 was prepared using a procedure analogous to that described for compound 24 but using (R)-tert-butyl 2-formylmorpholine-4-carboxylate in place of tert-butyl methyl(2-oxoethyl)carbamate in the procedure of Example 1.1. The two diastereomers I-29 and I-30 were separated by preparative HPLC to provide intermediate I-29 (340 mg) and intermediate I-30 (420 mg).

Example 1.X. Preparation of tert-butyl (+/−)—((R)-1-((R)-3,4-dihydro-1H-[1,4]oxazino[4,3-b]indazol-1-yl)ethyl)carbamate (I-32) and (+/−)-tert-butyl((S)-1-((R)-3,4-dihydro-1H-[1,4]oxazino[4,3-b]indazol-1-yl)ethyl)carbamate (I-33)

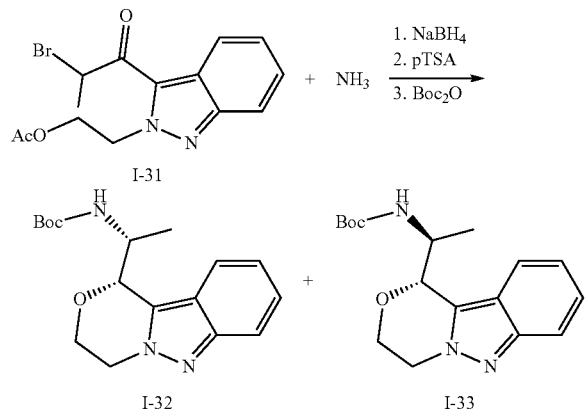

To a solution of intermediate I-31 (3.91 g, 11.53 mmol, prepared using a procedure analogous to that described for intermediate I-25 but using intermediate I-2 in place of intermediate I-11 and methyl propionate in place of tert-butyl methyl(2-oxoethyl)carbamate in the procedure of Example 1.1) in a mixture of acetonitrile (50.0 mL) and methanol (10.0 mL) was added a solution of $NH_3$ in methanol (20.0 M) (80.0 mL) dropwise at −78° C. and the reaction mixture was stirred at room temperature for 5.0 h. Sodium tetrahydroborate (1.1 g, 29.0 mmol) was added portion-wise to the reaction mixture at room temperature over 5.0 min. After 1 h, the reaction was quenched with water (50.0 mL) and concentrated under reduced pressure. The residue was dissolved in toluene (250.0 mL) and to this solution was added 4-methylbenzenesulfonic acid (19.4 g, 112.5 mmol) in one portion at room temperature. The reaction mixture was stirred at reflux for 16 hrs, concentrated under reduced pressure, the residue was dissolved in methanol (300 mL) and neutralized with solid sodium carbonate (11.93 g, 112.5 mmol). To this mixture was added triethylamine (0.96 g, 9.5 mmol) and di-tert-butyl dicarbonate (3.69 g, 16.95 mmol) in one portion at room temperature, the reaction mixture was stirred at room temperature for 1.5 h and concentrated under reduced pressure. The residue was dissolved in dichloromethane (500.0 mL), washed with brine (150.0 mL×3), the organic phase was concentrated under reduced pressure to afford the crude product which was purified through silica gel. (dichloromethane:methanol=50:1) and then by preparative TLC (dichloromethane:methanol=30:1) to provide the low polarity intermediate I-32 (677 mg, yellow solid, 18%), MS (ESI): m/z 318 [M+H]$^+$ and the high polarity intermediate I-33 (360 mg, yellow solid, 10%), MS (ESI): m/z 318 [M+H]$^+$.

Example 1.Y. Preparation of (+/−)-tert-butyl ((R)-1-((R)-3,4-dihydro-1H-[1,4]oxazino[4,3-b]indazol-1-yl)ethyl)(methyl)carbamate (I-34)

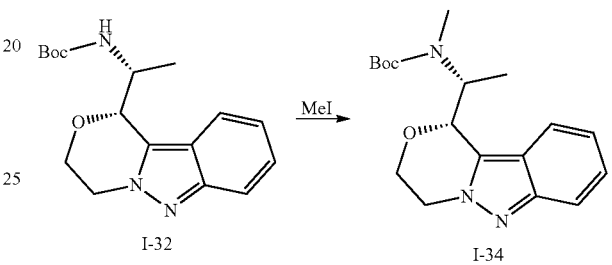

To a solution of intermediate I-32 (550.0 mg, 1.73 mmol) in a mixture of N,N-dimethylformamide (5.0 mL) and tetrahydrofuran (5.0 mL) was added sodium hydride (60% in oil, 0.139 g, 3.47 mmol) and iodomethane (0.22 mL, 3.47 mmol) in one portion at room temperature and the reaction mixture was stirred at room temperature for 1.0 h. The reaction mixture was quenched with an aqueous solution of $NH_4Cl$ (10 mL), diluted with dichloromethane (50 mL) and washed with brine (30 mL×3). The organic phase was dried over sodium sulphate and concentrated under reduced pressure to afford intermediate I-34 (0.574 g, 100%) as a brown solid. MS (ESI): m/z 332 [M+H]$^+$.

Example 1.Z. Preparation of tert-butyl 3-hydroxy-3-(2-(2-(methylsulfonyloxy)ethyl)-2H-indazol-3-yl)azetidine-1-carboxylate (I-36)

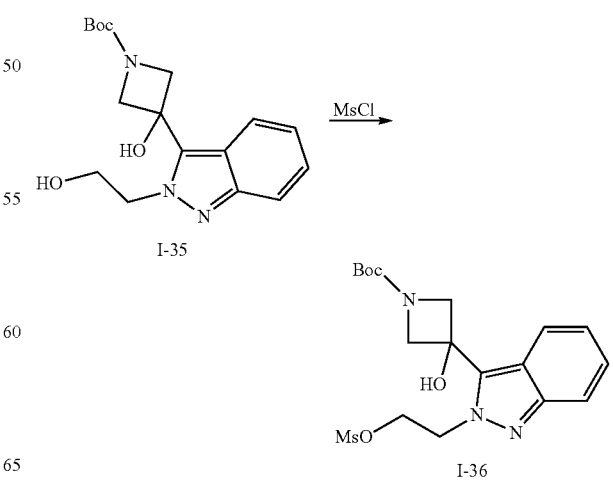

To a solution of intermediate I-35 (prepared using a procedure analogous to that described for intermediate I-3 but using tert-butyl 3-oxoazetidine-1-carboxylate in place of tert-butyl methyl(2-oxoethyl)carbamate in the procedure of Example 1.B. (420 mg, 1.26 mmol) in ethyl acetate (20 ml) was added triethylamine (0.48 g, 4.72 mmol) and the solution was cooled to 0° C. Methanesulfonyl chloride (0.14 g, 1.26 mmol) was added in several portions, the reaction mixture was stirred at 0° C. for 2 hrs and quenched with 30 ml of water. The crude reaction mixture was extracted with ethyl acetate (3×30 mL), the combined organic phase was dried over sodium sulfate and solids were removed by filtration. The filtrate was concentrated in vacuo to give intermediate I-36 (440 mg, 68%, white solid). MS (ESI): m/z 412.1 [M+H]+.

Example 1.AA. Preparation of (+/−)-1-((S)-morpholin-3-yl)-3,4-dihydro-1H-[1,4]oxazino[4,3-b]indazole (I-37)

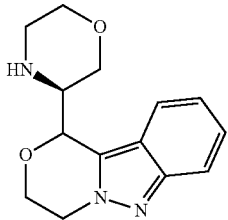

I-37

Intermediate I-37 was prepared using a procedure analogous to that described for intermediate I-4 but using (S)-tert-butyl 3-formylmorpholine-4-carboxylate in place of tert-butyl methyl(2-oxoethyl)carbamate in the procedure of Example 1.B. (1.09 g, brown oil); MS (ESI): m/z 260 [M+H]+.

Example 1.AB. Preparation of tert-butyl (+/−)-(3S)-3-(3,4-dihydro-1H-[1,4]oxazino[4,3-b]indazol-1-yl)morpholine-4-carboxylate (I-38)

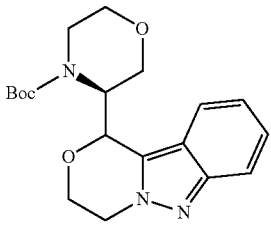

I-38

Intermediate I-38 was prepared using a procedure analogous to that described for intermediate I-5 but using intermediate I-37 in place of intermediate I-4 in the procedure of Example 1.D. (0.72 g, colorless oil); MS (ESI): m/z 360 [M+H]+.

Example 1.AC. Preparation of tert-butyl (+/−)—(S)-3-((R)-3,4-dihydro-1H-[1,4]oxazino[4,3-b]indazol-1-yl)morpholine-4-carboxylate (I-39) and tert-butyl (+/−)—(S)-3-((S)-3,4-dihydro-1H-[1,4]oxazino[4,3-b]indazol-1-yl)morpholine-4-carboxylate (I-40)

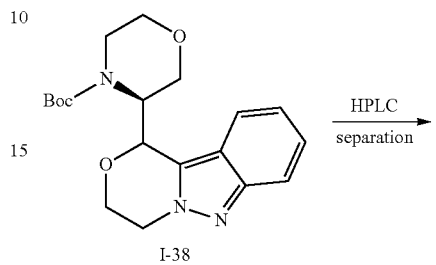

I-38

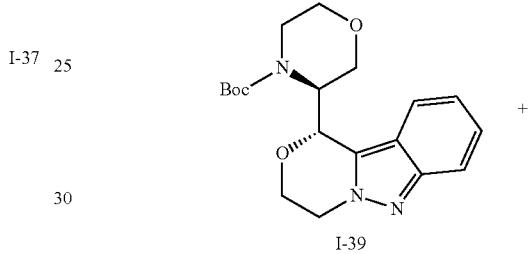

I-39

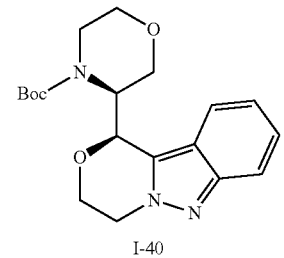

I-40

Cis/trans diastereomers of intermediate I-38 were separated by HPLC to provide intermediate I-39 (0.3 g, colorless oil) and intermediate I-40 (0.21 g, colorless oil).

Example 1.AD. Preparation of 3-(2H-indazol-2-yl)propan-1-ol (I-41)

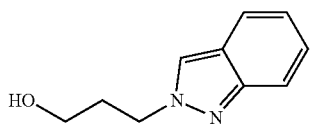

I-41

Intermediate I-41 was prepared using a procedure analogous to that described for intermediate I-2 but using 3-bromopropan-1-ol in place of 2-bromoethanol in the procedure of Example 1.A. (51.4 g, brown oil); MS (ESI): m/z 177 [M+H]+.

Example 1.AE. Preparation of 2-(3-(tert-butyldimethylsilyloxy)propyl)-2H-indazole (I-42)

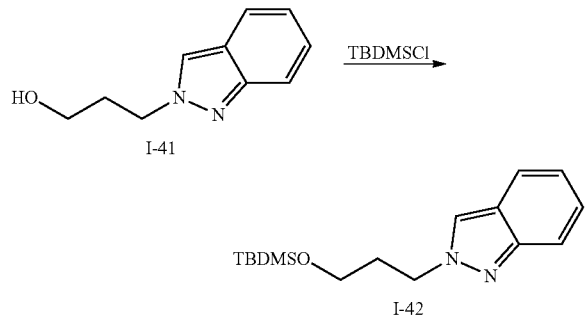

To a solution of intermediate I-41 (30 g, 170 mmol) in N,N-dimethylformamide (400 mL) was added tert-butylchlorodimethylsilane (38.4 g, 255 mmol) and 1H-imidazole (23.1 g, 340 mmol). The reaction mixture was stirred at room temperature for 16 h, concentrated in vacuo and the residue was purified by silica-gel chromatography (petroleum ether: EtOAc 9:1) to provide intermediate I-42. (39.7 g, 81%, orange oil); MS (ESI): m/z 291 [M+H]$^+$.

Example 1.AF. Preparation of tert-butyl 2-(2-(3-(tert-butyldimethylsilyloxy)propyl)-2H-indazol-3-yl)-2-hydroxyethyl(methyl)carbamate (I-43)

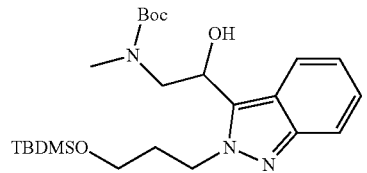

Intermediate I-43 was prepared using a procedure analogous to that described for intermediate I-12 but using intermediate I-42 in place of intermediate I-11 in the procedure of Example 1.I. (11 g, orange oil); MS (ESI): m/z 464 [M+H]$^+$.

Example 1.AG. Preparation of tert-butyl 2-hydroxy-2-(2-(3-hydroxypropyl)-2H-indazol-3-yl)ethyl(methyl)carbamate (I-44)

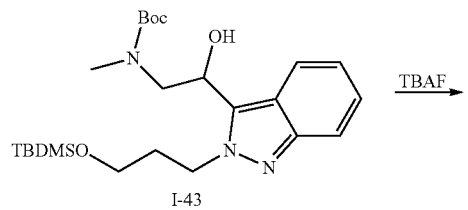

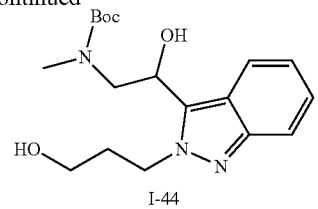

To a solution of intermediate I-43 (1.0 g, 2.16 mmol) in tetrahydrofuran (10 mL) was added tetrabutylammonium fluoride (0.52 g, 2.16 mmol) and the reaction mixture was stirred at ambient temperature overnight. The crude reaction mixture was extracted with ethyl acetate, the combined organic layers were dried with Na$_2$SO$_4$. Solids were removed by filtration and the filtrate was concentrated in vacuo. The resulting oil was purified by flash column chromatography (dichloromethane/methanol=20/1) to provide intermediate I-44. (500 mg, 66.2%, yellow oil); MS (ESI): m/z 350 [M+H]$^+$.

Example 1.AH. Preparation of N-methyl(1,3,4,5-tetrahydro-[1,4]oxazepino[4,3-b]indazol-1-yl)methanamine (I-45)

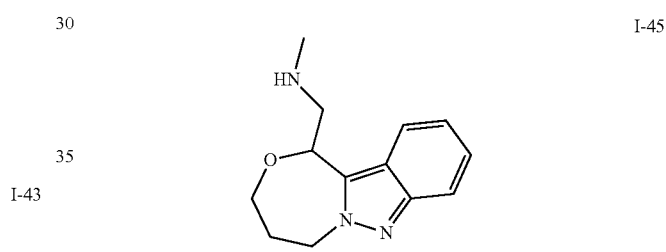

Intermediate I-45 was prepared using a procedure analogous to that described for intermediate I-4 but using intermediate I-44 in place of intermediate I-3 in the procedure of Example 1.C. MS (ESI): m/z 232 [M+H]$^+$.

Example 1.AI. Preparation of tert-butyl methyl((1,3,4,5-tetrahydro-[1,4]oxazepino[4,3-b]indazol-1-yl)methyl)carbamate (I-46)

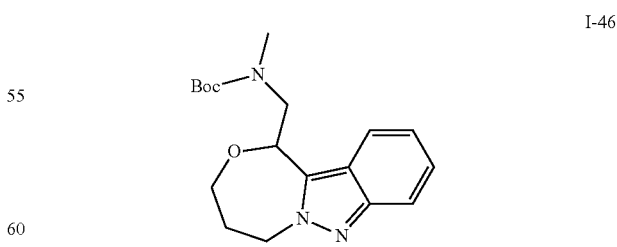

Intermediate I-46 was prepared using a procedure analogous to that described for intermediate I-5 but using intermediate I-45 in place of intermediate I-4 in the procedure of Example 1.D. (4.0 g, orange oil); MS (ESI): m/z 332 [M+H]$^+$.

Example 1.AJ. Preparation of 2-(3-hydroxypropyl)-2H-indazole-3-carbaldehyde (I-47)

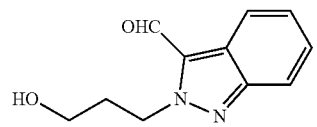

I-47

Intermediate I-47 was prepared using a procedure analogous to that described for intermediate I-16 but using intermediate I-41 in place of intermediate I-15 in the procedure of Example 1.L. (5.5 g, yellow oil); MS (ESI): m/z 286 [M+H]+.

Example 1.AK. Preparation of 2-(2-(3-hydroxypropyl)-2H-indazol-3-yl)-2-(trimethylsilyloxy)acetonitrile (I-48)

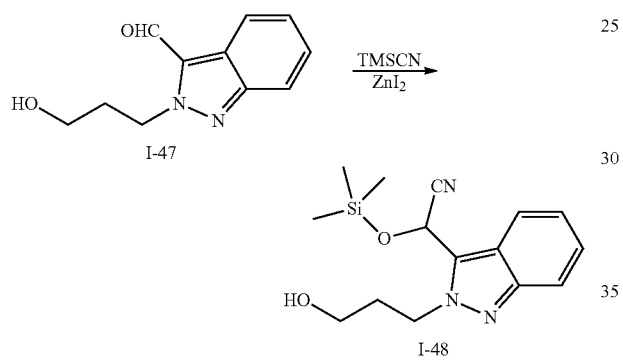

To a solution of intermediate I-47 (3.17 g, 15.5 mmol) in methanol (40 mL) was added zinc(II) iodide (4.94 g, 15.5 mmol) and trimethylsilanecarbonitrile (3.07 g, 31 mmol). The reaction mixture was stirred at room temperature for 1 h, concentrated in vacuo, the crude residue used in the following step without further purification.

Example 1.AL. Preparation of 3-(3-(2-amino-1-hydroxyethyl)-2H-indazol-2-yl)propan-1-ol (I-49)

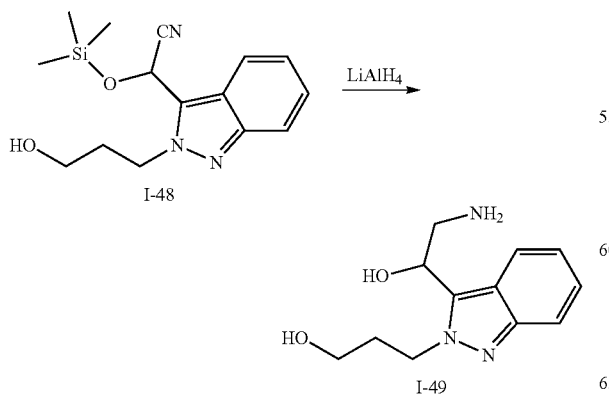

To a solution of intermediate I-48 (5.9 g, 19.6 mmol) in tetrahydrofuran (100 mL) was added Lithium aluminum hydride (1.48 g, 39.2 mmol) and the reaction mixture was stirred at room temperature for 1 h. Water (20 mL) was added, solids were removed by filtration and the filtrate was concentrated in vacuo. The crude residue was used for in the following step without further purification. MS (ESI): m/z 236 [M+H]+.

Example 1.AM. Preparation of (1,3,4,5-tetrahydro-[1,4]oxazepino[4,3-b]indazol-1-yl)methanamine (I-50)

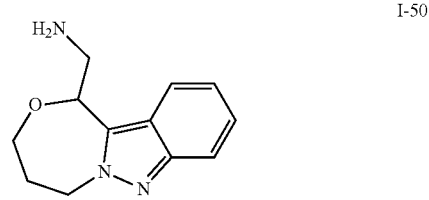 [SMILES: NCC1OCCCn2nc3ccccc3c21]

Intermediate I-50 was prepared using a procedure analogous to that described for intermediate I-4 but using intermediate I-49 in place of intermediate I-3 in the procedure of Example 1.C. MS (ESI): m/z 218 [M+H]+.

Example 1.AN. Preparation of tert-butyl (1,3,4,5-tetrahydro-[1,4]oxazepino[4,3-b]indazol-1-yl)methylcarbamate (I-51)

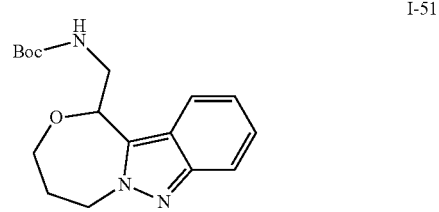 [SMILES: CC(C)(C)OC(=O)NCC1OCCCn2nc3ccccc3c21]

Intermediate I-51 was prepared using a procedure analogous to that described for intermediate I-5 but using intermediate I-50 in place of intermediate I-4 in the procedure of Example 1.D. (160 mg); MS (ESI): m/z 318 [M+H]+.

Example 1.AO. Preparation of tert-butyl ethyl((1,3,4,5-tetrahydro-[1,4]oxazepino[4,3-b]indazol-1-yl)methyl)carbamate (I-52)

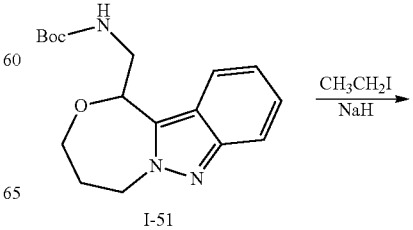

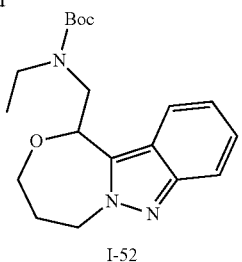

I-52

To a solution of intermediate I-51 (140 mg, 441 μmol) in N,N-Dimethyl formamide (5 mL) was added sodium hydride (27 mg, 1.12 mmol) and iodoethane (232 mg, 1.49 mmol) and the reaction was stirred at room temperature for 3 h. Water (5 mL) was added followed by ethyl acetate (20 mL) and the resulting biphasic mixture was transferred to a reparatory funnel. The layers were separated and the organic phase was washed with water (2×10 mL) and brine (2×10 mL). The combined organic layers were dried over anhydrous sodium sulfate, solids were removed by filtration and the filtrate was concentrated in vacuo. The residue was purified by preparative thin layer chromatography with petrol ether/ethyl acetate=3/1 to provide intermediate I-52. (120 mg, 79%, clear oil); MS (ESI): m/z 346 [M+H]$^+$.

Example 1.AP. Preparation of 3-bromothiophene-2-carbaldehyde (I-53)

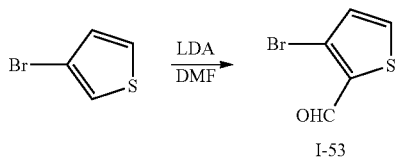

I-53

To a solution of 3-bromothiophene (25 g, 153 mmol) in tetrahydrofuran (250 mL) was added 2 M Lithium diisopropylamide in tetrahydrofuran (77 mL, 154 mmol) at 0° C. and the reaction mixture was stirred at 0° C. for 1 h. N,N-dimethylformamide (12.2 g, 168 mmol) was added and the reaction mixture was allowed to warm to room temperature and stirred for additional 2 h. Water (100 mL) was added and extracted with ethyl acetate (500 mL×3) was performed. The combined organic layer were dried over anhydrous magnesium sulfate, solids were removed by filtration and the filtrate was concentrated by evaporation in vacuo. The residue was purified by silica gel chromatography (petrol ether/ethyl acetate=10/1) to provide intermediate I-53 (20 g, 68%). MS (ESI): m/z 190 [M+H]$^+$.

Example 1.AQ. Preparation of 3-azidothiophene-2-carbaldehyde (I-54)

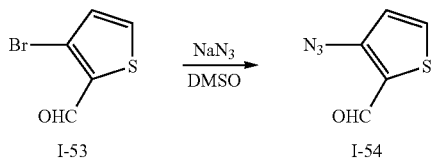

To a solution of intermediate I-53 (2.0 g, 10.47 mmol) in dimethyl sulfoxide (15 mL) was added sodium azide (2.72 g, 41.88 mmol) and the solution was stirred at 80° C. for 4 h. Water (100 mL) was added, the aqueous layer was extracted by ethyl acetate (2×100 mL), the organic phase was washed by brine and dried over anhydrous sodium sulfate. Solids were removed by filtration, and the filtrate was concentrated in vacuo. The residue was purified by silica gel chromatography (petrol ether/ethyl acetate=5/1) to provide intermediate I-54 (840 mg, 52%). MS (ESI): m/z 154 [M+H]$^+$.

Example 1.AR. Preparation of 2-(2H-thieno[3,2-c]pyrazol-2-yl)ethanol (I-55)

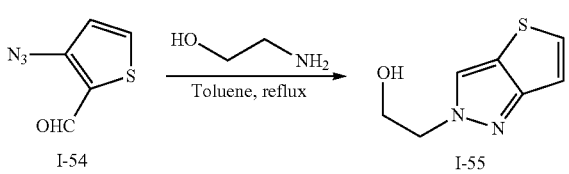

To a solution of intermediate I-54 (1.45 g, 9.47 mmol) in toluene (20 mL) was added 2-aminoethanol (1.16 g, 18.94 mmol) and the reaction mixture was stirred at 120° C. for 3 h. The crude reaction mixture was concentrated in vacuo, water (20 mL) was added, the aqueous phase was extracted by ethyl acetate (2×50 mL), the combined organic layers were washed with brine (50 mL) and the dried over anhydrous sodium sulfate. Solids were removed by filtration, the filtrate was concentrated in vacuo and the residue was purified by silica gel column chromatography (petrol ether:ethyl acetate=5:1) to provide intermediate I-55. (400 mg, 25%, yellow oil); MS (ESI): m/z 169 [M+H]$^+$.

Example 1.AS. Preparation of tert-butyl 2-hydroxy-2-(2-(2-hydroxyethyl)-2H-thieno[3,2-c]pyrazol-3-yl)ethyl(methyl)carbamate (I-56)

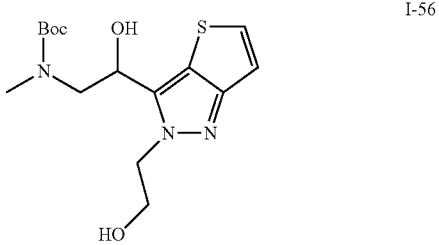 [SMILES: CN(CC(O)c1c2sccc2nn1CCO)C(=O)OC(C)(C)C]

I-56

Intermediate I-56 was prepared using a procedure analogous to that described for intermediate I-3 but using intermediate I-55 in place of intermediate I-2 in the procedure of Example 1.B. (170 mg, 12%, white solid); MS (ESI): m/z 342 [M+H]$^+$.

Example 1.AT. Preparation of 1-(7,9-dihydro-6H-thieno[3',2':3,4]pyrazolo[5,1-c][1,4]oxazin-9-yl)-N-methylmethanamine (I-57)

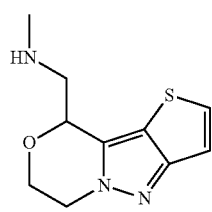

I-57

Intermediate I-57 was prepared using a procedure analogous to that described for intermediate I-4 but using intermediate I-56 in place of intermediate I-3 in the procedure of Example 1.C. MS (ESI): m/z 224 [M+H]$^+$.

Example 1.AU. Preparation of tert-butyl ((7,9-dihydro-6H-thieno[3',2':3,4]pyrazolo[5,1-c][1,4]oxazin-9-yl)methyl)(methyl)carbamate (I-58)

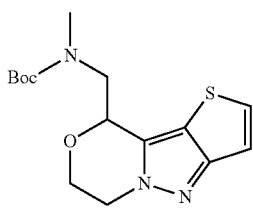

I-58

Intermediate I-58 was prepared using a procedure analogous to that described for intermediate I-5 but using intermediate I-57 in place of intermediate I-4 in the procedure of Example 1.D. (95 mg, white solid); MS (ESI): m/z 324 [M+H]$^+$.

Example 1.AV. Synthesis of 2-(2-hydroxyethyl)-2H-thieno[3,2-c]pyrazole-3-carbaldehyde (I-59)

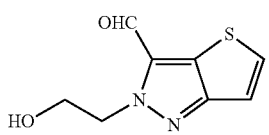

I-59

Intermediate I-59 was prepared using a procedure analogous to that described for intermediate I-16 but using intermediate I-55 in place of intermediate I-15 in the procedure of Example 1.L. (600 mg, yellow oil); MS (ESI): m/z 197 [M+H]$^+$.

Example 1.AW. Synthesis of 2-(2-(2-hydroxyethyl)-2H-thieno[3,2-c]pyrazol-3-yl)-2-(trimethylsilyloxy)acetonitrile (I-60)

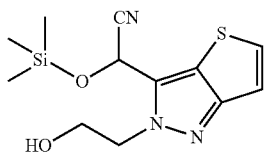

I-60

Intermediate I-60 was prepared using a procedure analogous to that described for intermediate I-48 but using intermediate I-59 in place of intermediate I-47 in the procedure of Example 1.AK.

Example 1.AX. Synthesis of 2-amino-1-(2-(2-hydroxyethyl)-2H-thieno[3,2-c]pyrazol-3-yl)ethanol (I-61)

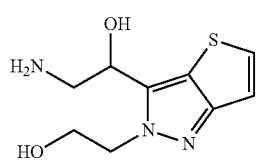

I-61

Intermediate I-61 was prepared using a procedure analogous to that described for intermediate I-49 but using intermediate I-60 in place of intermediate I-48 in the procedure of Example 1.AL. MS (ESI): m/z 228 [M+H]$^+$.

Example 1.AY. Synthesis of (7,9-dihydro-6H-thieno[3',2':3,4]pyrazolo[5,1-c][1,4]oxazin-9-yl)methanamine (I-62)

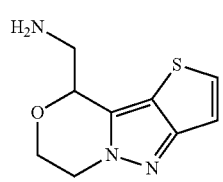

I-62

Intermediate I-62 was prepared using a procedure analogous to that described for intermediate I-4 but using intermediate I-61 in place of intermediate I-3 in the procedure of Example 1.C. MS (ESI): m/z 210 [M+H]$^+$.

Example 1.AZ. Synthesis of tert-butyl ((7,9-dihydro-6H-thieno[3',2':3,4]pyrazolo[5,1-c][1,4]oxazin-9-yl)methyl)carbamate (I-63)

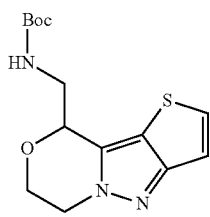

I-63

Intermediate I-63 was prepared using a procedure analogous to that described for intermediate I-5 but using intermediate I-62 in place of intermediate I-4 in the procedure of Example 1.D. (165 mg, 12%, yellow oil); MS (ESI): m/z 310 [M+H]+.

Example 1.BA. Synthesis of N-(4-methylpyridin-3-yl)acetamide (I-64)

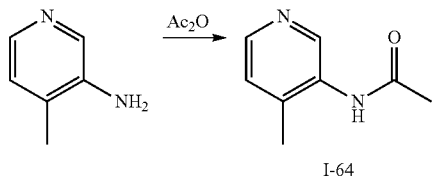

Into a 250 mL round bottom flask was placed a solution of 4-methylpyridin-3-amine (10 g, 92.47 mmol, 1.00 equiv) in acetic anhydride (50 mL). The resulting solution was stirred for 1 hour at room temperature. Water (200 ml) was added, the pH of the solution was adjusted to 7 by addition of sodium carbonate (1M solution in water). The crude reaction mixture was extracted with ethyl acetate (3×300 ml), the combined organic layers were dried over anhydrous sodium sulfate, solids were removed by filtration and the filtrate was concentrated in vacuo. The residue was purified by silicagel-gel chromatography (dichloromethane/methanol: 20/1) to provide intermediate I-64. (12 g, 94%); MS (ESI): m/z 151 [M+H]+.

Example 1.BB. Synthesis of Preparation of tert-butyl 3-(3-acetamidopyridin-4-yl)-2-hydroxypropyl(methyl)carbamate (I-65)

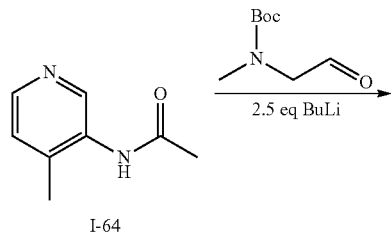

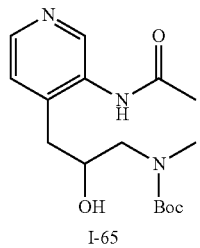

I-65

To a solution of intermediate I-64 (2.5 g) in dry THF (70 mL) at −78° C. under argon was added n-BuLi (17 mL, 2.5 M in hexanes) and the reaction mixture was stirred at −78° C. for 15 min and then at −25° C. for additional 90 min. The reaction mixture was cooled to −78° C. and a solution of tert-butyl methyl(2-oxoethyl)carbamate (3.46 g) in dry tetrahydrofuran (20 mL) was added drop-wise. The reaction mixture was stirred at −78° C. for 10 min and then at −20° C. for additional 3 h. A saturated aqueous solution of ammonium chloride was added to quench excess n-BuLi. The crude reaction mixture was concentrated in vacuo, water was added to the residue and extraction with dichloromethane (4×50 mL) was performed. The combined organic layers were dried over anhydrous Na2SO4, solids were removed by filtration and the filtrate was concentrated in vacuo. The orange oily residue was purified by silicagel chromatography (dichloromethane/methanol 50/1) to provide intermediate I-65. (2.69 g, 50%, light-yellow oil); MS (ESI): m/z 324 [M+H]+.

Example 1.BC. Synthesis of 1-(1-acetyl-1H-pyrazolo[3,4-c]pyridin-3-yl)-2-(tert-butoxycarbonyl(methyl)amino)ethyl acetate (I-66)

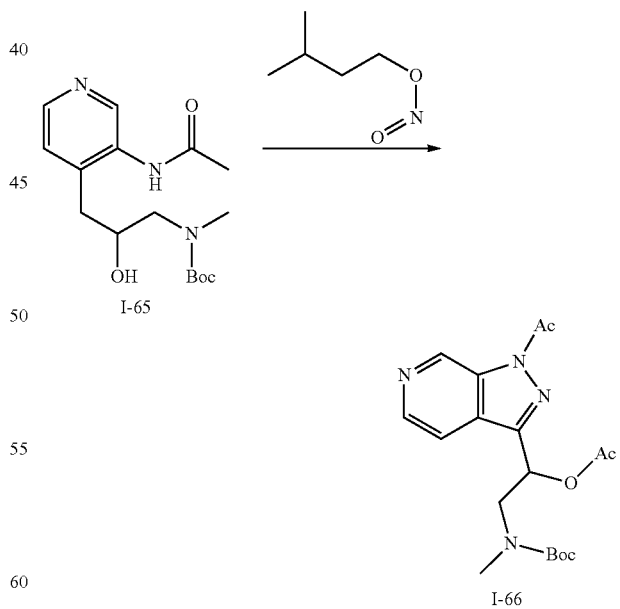

To a suspension of intermediate I-65 (1.0 g, 3.09 mmol) in dry toluene (30 mL) under argon were added potassium acetate (314 mg, 2.0 mmol) and acetic anhydride (0.8 mL, 8.1 mmol). The reaction mixture was stirred at 80° C. while isoamyl nitrite (1.1 mL, 7.72 mmol) was added drop-wise and the reaction mixture was heated at 100° C. for 16 h. Solids were removed by filtration, the residue was washed with hot toluene and the combined filtrates were concentrated in vacuo to afford intermediate I-66 that was used in the following step without further purification. (1.0 g, dark oil); MS (ESI): m/z 377 [M+H]⁺.

Example 1.BD. Synthesis of tert-butyl 2-(2-hydroxyethoxy)-2-(2H-pyrazolo[3,4-c]pyridin-3-yl)ethyl(methyl)carbamate (I-67)

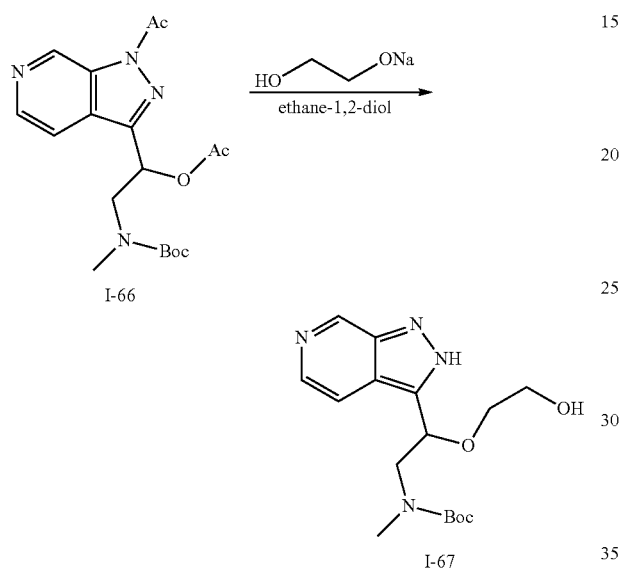

To a solution of intermediate I-66 (1.8 g, 4.78 mmol) in ethane-1,2-diol (10 mL) was added sodium hydroxide (0.57 g, 14.34 mmol) and the reaction mixture was stirred at ambient temperature for 24 h. Ethyl acetate (100 mL) was added and extraction was performed. The combined organic layers were washed with brine (3×20 mL), dried over anhydrous sodium sulfate, solids were removed by filtration and the filtrate was concentrated in vacuo. The residue was purified by silica gel chromatography (dichloromethane/methanol) to provide intermediate I-67 (0.03 g, 2%, oil); MS (ESI): m/z 337 [M+H]⁺.

Example 1.BE. Synthesis of tert-butyl ((3,4-dihydro-1H-pyrido[3',4':3,4]pyrazolo[5,1-c][1,4]oxazin-1-yl)methyl)(methyl)carbamate (I-68)

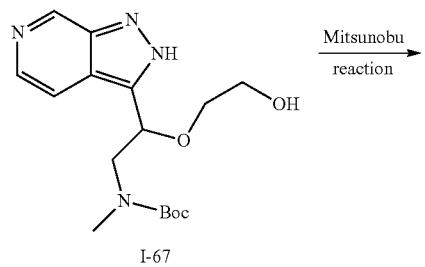

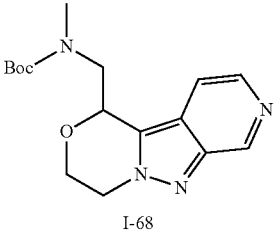

To a solution of intermediate I-67 (500 mg) and triphenylphosphine (776 mg) in dry tetrahydrofuran (50 mL) at 0° C. under argon was added DIAD (600 mg) and the reaction mixture was stirred at room temperature for 12 h. Water (30 mL) and ethyl acetate (2×100 mL) were added and extraction was performed. The combined organic layers were washed with brine (2×30 mL), dried over anhydrous sodium sulfate, solids were removed by filtration and the filtrate was concentrated in vacuo. The residue was purified by silica gel chromatography (petroleum ether/ethyl acetate) to provide intermediate I-68. (300 mg, 64%, white solid); MS (ESI): m/z 319 [M+H]⁺.

Example 1.BF. Preparation of tert-butyl (S)-2-(2-(2-hydroxyethyl)-2H-indazole-3-carbonyl)-azetidine-1-carboxylate (I-69)

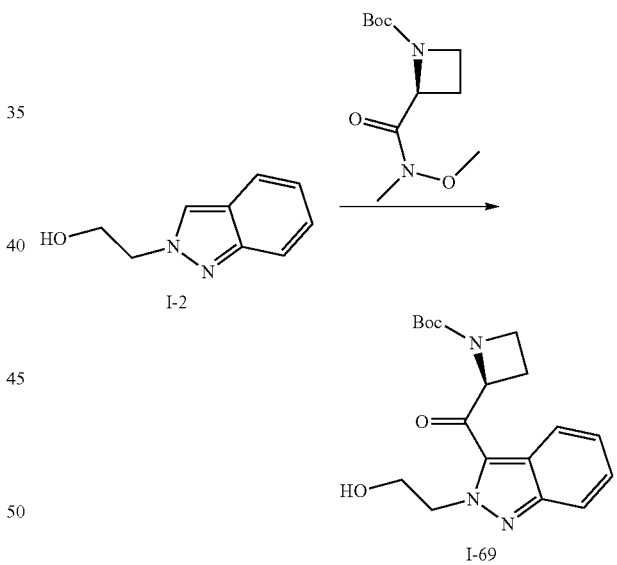

A solution of intermediate I-2 (3.24 g, 19.9 mmol) in THF (60 mL) was cooled to −78° C., a solution of n-BuLi (4.45 g, 69.6 mmol 2.5M in hexanes) was added dropwise and the reaction mixture was stirred at −78° C. for 1 hr. A solution of (S)-tert-butyl 2-(methoxy(methyl)carbamoyl)azetidine-1-carboxylate (4.86 g, 19.9 mmol) in THF (30 mL) was added to the mixture and allowed to warm to room temperature over the course of 1 hr. The reaction mixture was quenched with brine (50 mL), extracted with ethyl acetate (50 mL×3), the combined organic phase was dried over Na₂SO₄, solids were removed by filtration, the filtrate was concentrated in vacuo and the residue was purified by silicagel chromatography to give intermediate I-69 (552 mg, 8%) as a yellow oil. MS (ESI): m/z 346 [M+H]⁺.

Example 1.BG. Preparation of tert-butyl (2S)-2-(hydroxy(2-(2-hydroxyethyl)-2H-indazol-3-yl)methyl)azetidine-1-carboxylate (I-70)

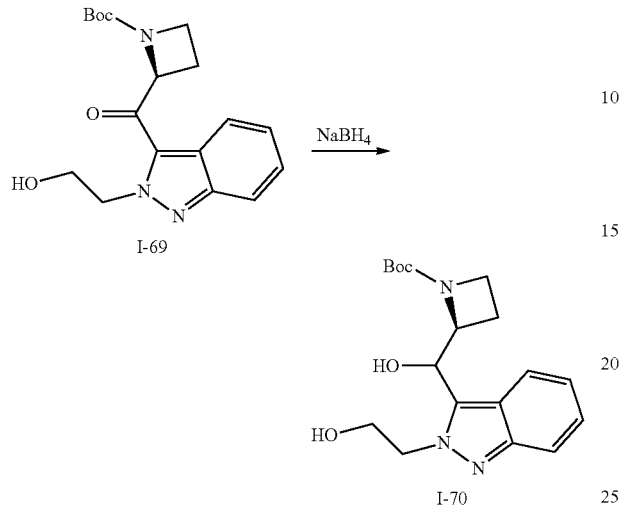

To a solution of intermediate I-69 (700 mg, 2.02 mmol) in MeOH (10 mL) was added solid NaBH$_4$ (76.4 mg, 2.02 mmol) and the reaction mixture was stirred at ambient temperature for 16 hrs. The crude reaction mixture was concentrated in vacuo and the residue was purified by silicagel chromatography to give intermediate I-70 (402 mg, 57%) as yellow oil. MS (ESI): m/z 348 [M+H]$^+$.

Example 1.BH. Preparation of tert-butyl (2S)-2-(hydroxy(2-(2-((methylsulfonyl)oxy)ethyl)-2H-indazol-3-yl)methyl)azetidine-1-carboxylate (I-71)

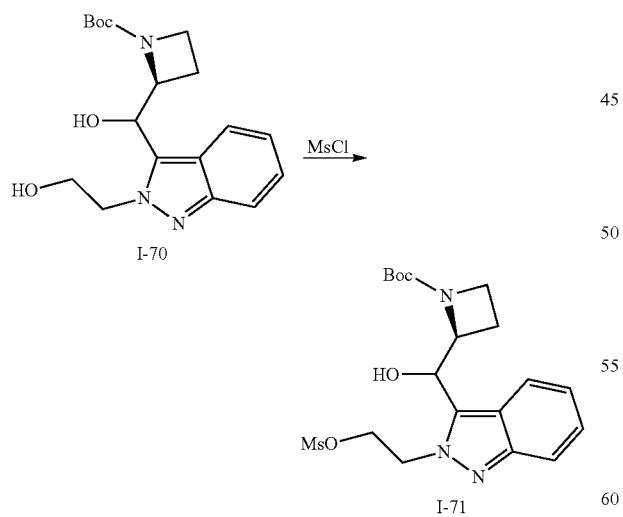

Intermediate I-71 was prepared using a procedure analogous to that described for intermediate I-36 but using intermediate I-70 in place of intermediate I-35 in the procedure of Example 1.Z. (497 mg, 45%) as yellow oil. MS (ESI): m/z 426 [M+H]$^+$.

Example 1.1. Preparation of (S)-(3,4-dihydro-1H-[1,4]oxazino[4,3-b]indazol-1-yl)-N-methylmethanaminium chloride (1)

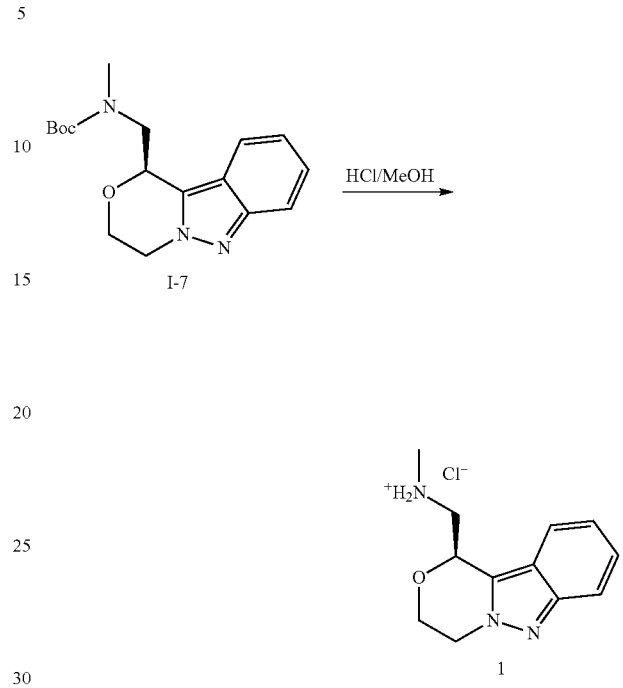

To a solution of intermediate I-7 (2.0 g, 6.0 mmol) in dichloromethane (20 mL) was added 4 M HCl/methanol (8 mL) dropwise, the resulting solution was stirred for 10 min and concentrated to give compound 1 (1.30 g, 86%) as a white solid. MS (ESI): m/z 218 [M+H]$^+$; $^1$H-NMR (400 MHz, MeOD): δ 7.68-7.71 (d, J=8.4 Hz, 1H), 7.48-7.57 (m, 2H), 7.23-7.27 (m, 1H), 5.61-5.63 (m, 1H), 4.36-4.53 (m, 3H), 4.08-4.14 (m, 1H), 3.77-3.81 (m, 1H), 3.50-3.56 (m, 1H), 2.67 (s, 3H).

Example 1.2. Preparation of (R)-(3,4-dihydro-1H-[1,4]oxazino[4,3-b]indazol-1-yl)-N-methylmethanaminium chloride (2)

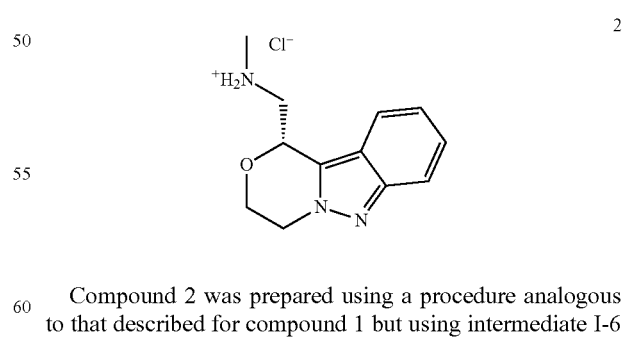

Compound 2 was prepared using a procedure analogous to that described for compound 1 but using intermediate I-6 in place of intermediate I-7 in the procedure of Example 1.1. (1.25 g, white solid); MS (ESI): m/z 218 [M+H]$^+$; $^1$H-NMR (400 MHz, MeOD): δ 7.64-7.66 (d, J=8.8 Hz, 1H), 7.46-7.55 (m, 2H), 7.19-7.24 (m, 1H), 5.56-5.59 (m, 1H), 4.38-4.71 (m, 3H), 4.09-4.15 (m, 1H), 3.76-3.81 (m, 1H), 3.50-3.56 (m, 1H), 2.71 (s, 3H).

Example 1.3. Preparation of 5-9 (S)-(3,4-dihydro-1H-[1,4]oxazino[4,3-b]indazol-1-yl)-N,N-dimethylmethanaminium chloride (3)

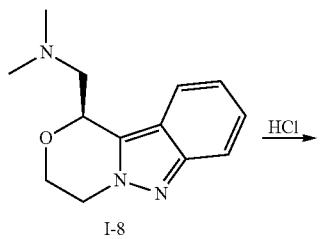

I-8

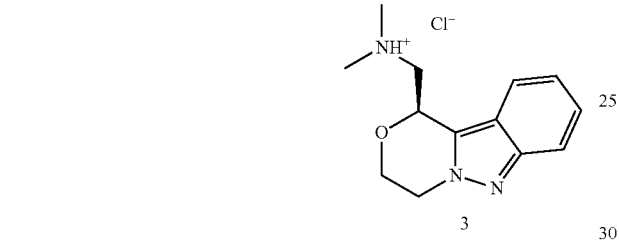

3

To a solution of intermediate I-8 (1.0 g, 4.33 mmol) in dichloromethane (20 mL) was added 4 M HCl/methanol (8 mL) dropwise, the resulting solution was stirred for 2 min and concentrated to give compound 3 (1.1 g, 86%) as a white solid. MS (ESI): m/z 232 [M+H]$^+$, $^1$H-NMR (400 MHz, MeOD): δ 7.58-7.64 (m, 2H), 7.42-7.44 (d, J=6.8 Hz, 1H), 7.18 (s, 1H), 5.64-5.69 (m, 1H), 4.39-4.53 (m, 3H), 4.11-4.17 (m, 1H), 3.88-3.91 (d, J=13.2 Hz, 1H), 3.59-3.65 (m, 1H), 3.02 (s, 3H), 2.87 (s, 3H).

Example 1.4. Preparation of (R)-(3,4-dihydro-1H-[1,4]oxazino[4,3-b]indazol-1-yl)-N,N-dimethylmethanaminium chloride (4)

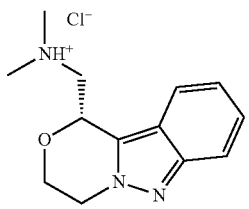

4

Compound 4 was prepared using a procedure analogous to that described for compound 3 but using compound 2 in place of compound 1 in the procedure of Example 1.F. (1.1 g, white solid); MS (ESI): m/z 232 [M+H]$^+$; $^1$H-NMR (400 MHz, MeOD): δ 7.51-7.53 (m, 2H), 7.33-7.37 (m, 1H), 7.10-7.13 (m, 1H), 5.44-5.47 (m, 1H), 4.28-4.44 (m, 3H), 4.03-4.09 (m, 1H), 3.78-3.82 (m, 1H), 3.46-3.52 (m, 1H), 2.99 (s, 3H), 2.86 (s, 3H).

Example 1.5. Preparation of 1-(9-chloro-3,4-dihydro-1H-[1,4]oxazino[4,3-b]indazol-1-yl)-N-methylmethanaminium chloride (5)

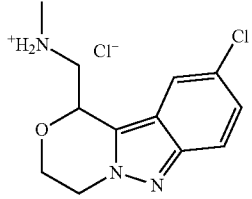

5

Compound 5 was prepared using a procedure analogous to that described for compound 3 but using intermediate I-13 in place of intermediate I-8 in the procedure of Example 1.3. (145 mg, white solid); MS (ESI): m/z 252 [M+H]$^+$.

Example 1.6. Preparation of 1-(9-chloro-3,4-dihydro-1H-[1,4]oxazino[4,3-b]indazol-1-yl)-N,N-dimethylmethanaminium chloride (6)

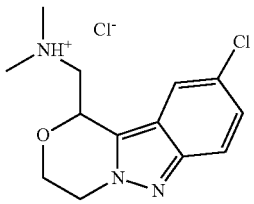

6

Compound 6 was prepared using a procedure analogous to that described for compound 3 but using intermediate I-14 in place of intermediate I-8 in the procedure of Example 1.3. (115 mg, white solid); MS (ESI): m/z 265 [M+H]$^+$.

Example 1.7. Preparation of 1-(9-fluoro-3,4-dihydro-1H-[1,4]oxazino[4,3-b]indazol-1-yl)-N-methylmethanaminium chloride (7)

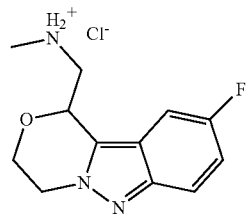

7

Compound 7 was prepared using a procedure analogous to that described for compound 5 but using 5-fluoro-1H-indazole in place of 1H-indazole in the procedure of Example 1.A. (450 mg, white solid); MS (ESI): m/z 236 [M+H]$^+$; $^1$H-NMR (400 MHz, MeOD): δ 7.70-7.74 (d, J=9.6, 1H), 7.58-7.60 (d, J=9.6, 1H), 7.25-7.39 (m, 1H), 5.64-5.67 (dd, J$_1$=8.8 Hz, J$_2$=2.4 Hz, 1H), 4.60-4.64 (m, 1H), 4.53-4.58 (m, 2H), 4.24-4.29 (m, 1H), 3.91-3.95 (d, J=9.6, 1H), 3.59-3.65 (m, 1H), 2.85 (s, 3H).

Example 1.8. Preparation of 1-(9-fluoro-3,4-dihydro-1H-[1,4]oxazino[4,3-b]indazol-1-yl)-N,N-dimethylmethanaminium chloride (8)

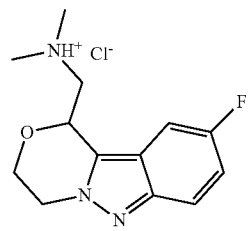

8

Compound 8 was prepared using a procedure analogous to that described for compound 3 but using compound 7 in place of compound 1 in the procedure of Example 1.F. (240 mg, white solid); MS (ESI): m/z 250 [M+H]$^+$; $^1$H-NMR (400 MHz, MeOD): δ 7.70-7.74 (d, J=9.6, 1H), 7.63-7.66 (d, J=9.6, 1H), 7.30-7.36 (m, 1H), 5.82-5.85 (dd, J=10.4, 2.8 Hz, 1H), 4.62-4.68 (m, 1H), 4.55-4.60 (m, 2H), 4.27-4.33 (m, 1H), 4.06-4.10 (d, J=13.6, 1H), 3.70-3.76 (m, 1H), 3.15 (s, 3H), 3.04 (s, 3H).

Example 1.9. Preparation of (9-fluoro-3,4-dihydro-1H-[1,4]oxazino[4,3-b]indazol-1-yl)methanaminium chloride (9)

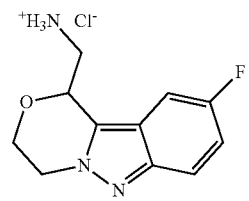

9

Compound 9 was prepared a procedure analogous to that described for compound 1 but using intermediate I-20 in place of intermediate I-7 in the procedure of Example 1.1. (60 mg, white solid); MS (ESI): m/z 222 [M+H]$^+$; $^1$H-NMR (400 MHz, MeOD): δ 7.70-7.73 (d, J=9.2, 1H), 7.49-7.52 (d, J=9.6, 1H), 7.27-7.32 (m, 1H), 5.55-5.58 (dd, J=7.8, 2.8 Hz, 1H), 4.59-4.62 (m, 1H), 4.52-4.56 (m, 2H), 4.22-4.28 (m, 1H), 3.79-3.83 (d, J=13.6 Hz, 1H), 3.51-3.57 (m, 1H).

Example 1.10. Preparation of 1-(8-fluoro-3,4-dihydro-1H-[1,4]oxazino[4,3-b]indazol-1-yl)-N-methylmethanaminium (10)

10

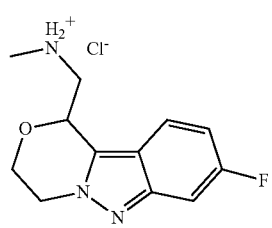

Compound 10 was prepared using a procedure analogous to that described for compound 5 but using 6-fluoro-1H-indazole in place of 1H-indazole in the procedure of Example 1.A. (450 mg, white solid); MS (ESI): m/z 236 [M+H]$^+$; $^1$H-NMR (400 MHz, MeOD): δ 8.07-8.03 (m, 1H), 7.41-7.38 (dd, J=9.6, 2.4 Hz, 1H), 7.20-7.15 (m, 1H), 5.76 (d, J=1.6 Hz, 1H), 4.65 (m, 1H), 4.57 (d, J=9.2 Hz, 2H), 4.29 (t, J=8.8 Hz, 1H), 4.01 (m, 1H), 3.67 (m, 1H), 3.33 (m, 1H), 2.86 (s, 3H).

Example 1.11. Preparation of 1-(8-fluoro-3,4-dihydro-1H-[1,4]oxazino[4,3-b]indazol-1-yl)-N,N-dimethylmethanaminium (11)

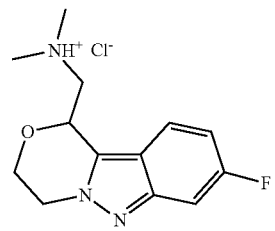

11

Compound 11 was prepared using a procedure analogous to that described for compound 3 but using compound 10 in place of compound 1 in the procedure of Example 1.F. (240 mg, white solid); MS (ESI): m/z 250 [M+H]$^+$; $^1$H-NMR (400 MHz, MeOD): δ 8.07-8.10 (m, 1H), 7.39-7.36 (dd, J=9.6, 2.4 Hz, 1H), 7.20-7.15 (m, 1H), 5.92 (d, J=2.4 Hz, 1H), 4.68 (m, 1H), 4.57-4.62 (m, 2H), 4.32 (m, 1H), 4.18-4.14 (d, J=3.2, 1H), 3.83-3.77 (m, 1H), 3.18 (s, 3H), 3.07 (s, 1H).

Example 1.12. Preparation of (8-fluoro-3,4-dihydro-1H-[1,4]oxazino[4,3-b]indazol-1-yl)methanaminium (12)

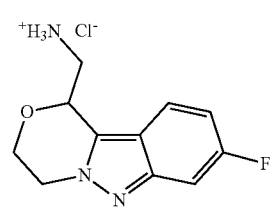

12

Compound 12 was prepared using a procedure analogous to that described for compound 9 but using 6-fluoro-1H-indazole in place of 1H-indazole in the procedure of Example 1.A. (60 mg, white solid); MS (ESI): m/z 222 [M+H]$^+$; $^1$H-NMR (400 MHz, MeOD): δ 8.04-8.01 (m, 1H), 7.41-7.38 (dd, J=9.6, 2.4 Hz, 1H), 7.19-7.15 (m, 1H), 5.71 (d, J=6.0 Hz 1H), 4.68-4.57 (m, 3H), 4.29 (m, 1H), 3.89 (d, J=7.2 Hz, 1H), 3.63 (m, 1H).

Example 1.13. Preparation of 1-((S)-pyrrolidin-2-yl)-3,4-dihydro-1H-[1,4]oxazino[4,3-b]indazole hydrochloride (13)

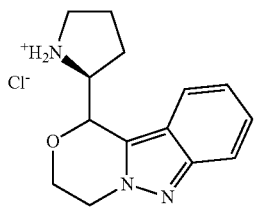

13

Compound 13 was prepared using a procedure analogous to that described for compound 5 but using (S)-tert-butyl 2-formylpyrrolidine-1-carboxylate in place of tert-butyl methyl(2-oxoethyl)carbamate in the procedure of Example 1.B. (80 mg, yellow oil); MS (ESI): m/z 244 [M+H]$^+$; $^1$H-NMR (400 MHz, MeOD): δ 7.89-7.91 (d, J=8.4, 1H), 7.69-7.71 (d, J=8.8, 1H), 7.47-7.51 (m, 1H), 7.26-7.29 (m, 1H), 5.62 (s, 1H), 4.71-4.74 (m, 2H), 4.54-4.62 (m, 2H), 4.24-4.28 (m, 1H), 3.28-3.32 (m, 2H), 2.41-2.45 (m, 2H), 2.08-2.26 (m, 2H).

Example 1.14. Preparation of 1-((S)-1-methylpyrrolidin-2-yl)-3,4-dihydro-1H-[1,4]oxazino[4,3-b]indazole hydrochloride (14)

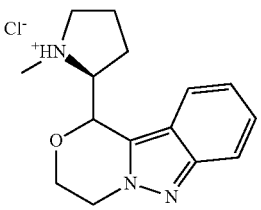

14

Compound 14 was prepared using a procedure analogous to that described for compound 3 but using compound 13 in place of compound 1 in the procedure of Example 1.F. (60 mg, yellow oil); MS (ESI): m/z 258 [M+H]$^+$; $^1$H NMR (400 MHz, MeOD): δ 7.70-7.72 (d, J=8.4 Hz, 1H), 7.58-7.60 (d, J=8.8 Hz, 1H), 7.31-7.35 (m, 1H), 7.08-7.12 (m, 1H), 5.44 (s, 1H), 4.42-4.61 (m, 3H), 4.08-4.15 (m, 1H), 3.33-3.35 (m, 1H), 3.14-3.16 (m, 1H), 2.59 (s, 3H), 2.40-2.44 (m, 1H), 1.68-1.76 (m, 3H), 1.49-1.54 (m, 1H).

Example 1.15. Preparation of (3,4-dihydro-1H-[1,4]oxazino[4,3-b]indazol-1-yl)methanamine (15)

15

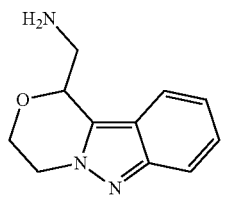

Compound 15 was prepared using a procedure analogous to that described for intermediate I-19 but using 1H-indazole in the procedure of Example 1.A (as shown, in place of the 5-fluoro-1H-indazole used in Example 1.L. (4.2 g, white solid); MS (ESI): m/z 204 [M+H]$^+$; $^1$H NMR (400 MHz, MeOD): δ 7.65 (d, J=8.4 Hz, 1H), 7.59 (d, J=8.8 Hz, 1H), 7.32 (t, J=7.2 Hz, 1H), 7.08 (t, J=7.2 Hz, 1H), 5.18 (d, J=6.8 Hz, 1H), 4.52-4.49 (m, 1H), 4.45-4.38 (m, 2H), 4.13-4.10 (m, 1H), 3.40 (dd, J=14.0, 2.0 Hz, 1H), 3.21-3.15 (m, 1H).

Example 1.16. Preparation of N-((3,4-dihydro-1H-[1,4]oxazino[4,3-b]indazol-1-yl)methyl) cyclobutanamine (16)

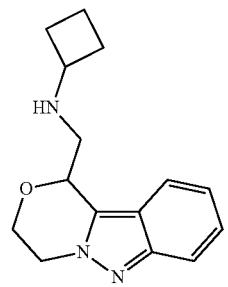

16

Compound 16 was prepared using a procedure analogous to that described for intermediate I-8 but using compound 15 in place of compound 1 and cyclobutanone in place of paraformaldehyde in the procedure of Example 1.F. (67 mg, white solid); MS (ESI): m/z 258 [M+H]$^+$; $^1$H-NMR (400 MHz, MeOD): δ 7.66 (d, J=8.8 Hz, 1H), 7.59 (d, J=8.4 Hz, 1H), 7.33 (t, J=7.2 Hz, 1H), 7.10 (t, J=7.6 Hz, 1H), 5.31 (d, J=7.2 Hz, 1H), 4.54 (m, 1H), 4.44 (m, 2H), 4.13 (m, 1H), 3.38-3.30 (m, 2H), 3.12-3.10 (m, 1H), 2.25-2.21 (m, 2H), 1.87-1.70 (m, 4H).

Example 1.17. Preparation of N-((3,4-dihydro-1H-[1,4]oxazino[4,3-b]indazol-1-yl)methyl)propan-2-amine (17)

17

Compound 17 was prepared using a procedure analogous to that described for intermediate I-8 but using compound 15 in place of compound 1 and propan-2-one in place of paraformaldehyde in the procedure of Example 1.F. (97 mg, white solid); MS (ESI): m/z 246 [M+H]$^+$; $^1$H NMR (400 MHz, MeOD): δ 7.67 (d, J=8.4 Hz, 1H), 7.60 (d, J=8.8 Hz, 1H), 7.33 (t, J=6.8 Hz, 1H), 7.10 (t, J=7.6 Hz, 1H), 5.35 (dd, J=8.4, 2.8 Hz, 1H), 4.54-4.51 (m, 1H), 4.48-4.41 (m, 2H), 4.17-4.11 (m, 1H), 3.43 (dd, J=12.8, 3.2 Hz, 1H), 3.15 (dd, J=12.8, 8.4 Hz, 1H), 2.98-2.95 (m, 1H), 1.14 (t, J=5.6 Hz, 6H).

Example 1.18. Preparation of N-((3,4-dihydro-1H-[1,4]oxazino[4,3-b]indazol-1-yl)methyl) ethanamine hydrogen chloride salt (18)

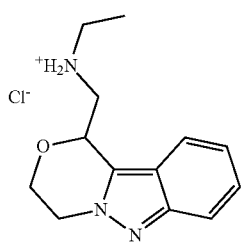

Compound 18 was prepared using a procedure analogous to that described for compound 1 but using intermediate I-22 in place of intermediate I-7 in the procedure of Example 1.1. (92 mg, white solid); MS (ESI): m/z 232 [M+H]$^+$; $^1$H-NMR (400 MHz, MeOD): δ 7.68 (d, J=8.4 Hz, 1H), 7.59 (d, J=8.8 Hz, 1H), 7.33 (t, J=7.6 Hz, 1H), 7.10 (t, J=7.6 Hz, 1H), 5.36 (dd, J=8.8, 2.8 Hz, 1H), 4.54-4.50 (m, 1H), 4.48-4.41 (m, 2H), 4.16-4.11 (m, 1H), 3.42 (dd, J=12.8, 3.2 Hz, 1H), 3.16 (dd, J=12.8, 8.4 Hz, 1H), 2.79-2.75 (m, 2H), 1.17 (t, J=7.2 Hz, 3H).

Example 1.19. Preparation of 1-(pyrrolidin-1-ylmethyl)-3,4-dihydro-1H-[1,4]oxazino[4,3-b]indazole hydrogen chloride salt (19)

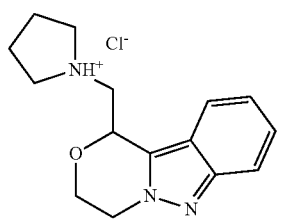

Compound 19 was prepared using a procedure analogous to that described for compound 1 but using intermediate I-26 in place of intermediate I-7 in the procedure of Example 1.1. (white solid); MS (ESI): m/z 258 [M+H]$^+$; 1H NMR (400 MHz, d$^4$-methanol): δ 8.01 (d, J=8.7 Hz, 1H), 7.72 (d, J=8.7 Hz, 1H), 7.60 (t, J=7.7 Hz, 1H), 7.35 (t, J=7.6 Hz, 1H), 5.82-5.94 (m, 1H), 4.66-4.78 (m, 1H), 4.55-4.66 (m, 2H), 4.27-4.40 (m, 1H), 4.14-4.25 (m, 1H), 3.84-3.99 (m, 2H), 3.67-3.81 (m, 1H), 3.39-3.54 (m, 1H), 3.22-3.31 (m, 1H), 1.96-2.38 (m, 4H).

Example 1.20. Preparation of 1-(morpholinomethyl)-3,4-dihydro-1H-[1,4]oxazino[4,3-b]indazole hydrogen chloride salt (20)

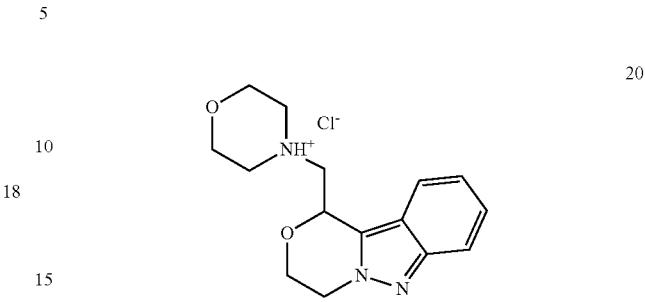

Compound 20 was prepared using a procedure analogous to that described for compound 19 but using morpholine in place of pyrrolidine in the procedure of Example 1.U. (White solid); MS (ESI): m/z 274 [M+H]$^+$; 1H NMR (400 MHz, d$^4$-methanol): δ 8.01 (d, J=8.5 Hz, 1H), 7.72 (d, J=8.7 Hz, 1H), 7.60 (t, J=7.7 Hz, 1H), 7.34 (t, J=7.6 Hz, 1H), 5.99-6.07 (m, 1H), 4.57-4.66 (m, 1H), 4.66-4.76 (m, 2H), 4.26-4.38 (m, 1H), 4.05-4.21 (m, 3H), 3.90-4.03 (m, 2H), 3.76-3.88 (m, 2H), 3.60-3.70 (m, 1H), 3.38-3.56 (m, 2H).

Example 1.21. Preparation of N-((3,4-dihydro-1H-[1,4]oxazino[4,3-b]indazol-1-yl)methyl)cyclopropan amine hydrogen chloride salt (21)

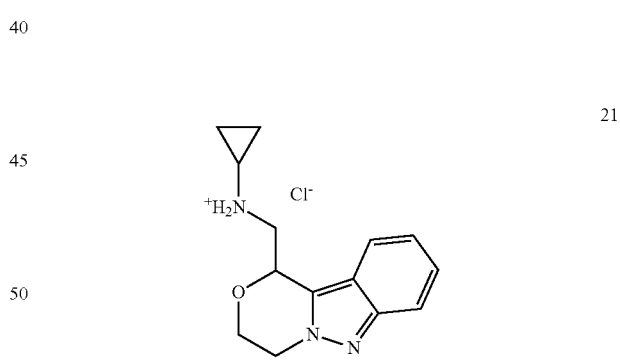

Compound 21 was prepared using a procedure analogous to that described for compound 19 but using cyclopropylamine in place of pyrrolidine in the procedure of Example 1.U. (White solid); MS (ESI): m/z 244 [M+H]$^+$; 1H NMR (400 MHz, d$^4$-methanol): δ 7.85-8.10 (m, 1H), 7.46-7.79 (m, 2H), 7.24-7.44 (m, 1H), 5.69-5.89 (m, 1H), 4.50-4.77 (m, 3H), 4.22-4.37 (m, 1H), 4.03-4.15 (m, 1H), 3.74-3.89 (m, 1H), 2.86-2.99 (m, 1H), 0.84-1.14 (m, 4H).

Example 1.22. Preparation of N-((3,4-dihydro-1H-[1,4]oxazino[4,3-b]indazol-1-yl)methyl)-N-methyl-cyclopropanamine hydrogen chloride salt (22)

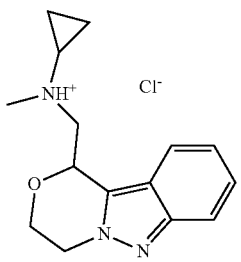

Compound 22 was prepared using a procedure analogous to that described for compound 3 but using compound 21 in place of compound 1 in the procedure of Example 1.F. (50.0 mg); MS (ESI): m/z 258 [M+H]$^+$; 1H-NMR (400 MHz, d$^4$-methanol): δ 8.10-8.20 (m, 1H), 7.69-7.79 (m, 2H), 7.42-7.47 (m, 1H), 5.95-6.25 (m, 1H), 4.57-4.80 (m, 3H), 4.30-4.40 (m, 2H), 3.89-4.14 (m, 1H), 3.10-3.30 (m, 4H), 1.16-1.46 (m, 2H), 0.94-1.14 (m, 2H).

Example 1.23. Preparation of 1'-methyl-3,4-dihydrospiro[[1,4]oxazino[4,3-b]indazole-1,3'-pyrrolidin]-1'-ium chloride (23)

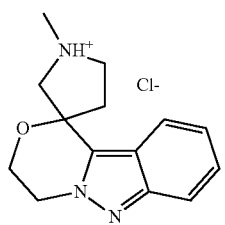

Compound 23 was prepared using a procedure analogous to that described for compound 3 but using intermediate I-27 in place of compound 1 in the procedure of Example 1.F. (160 mg, white solid, 95%); MS (ESI): m/z 244 [M+H]$^+$; 1H-NMR (400 MHz, CDCl$_3$): δ 7.69 (dd, J=19.6, 8.6 Hz, 2H), 7.29 (dd, J=13.5, 5.6 Hz, 1H), 7.11-7.01 (m, 1H), 4.47 (t, J=5.0 Hz, 2H), 4.23-4.15 (m, 2H), 3.12-2.98 (m, 3H), 2.83 (dd, J=14.8, 8.6 Hz, 1H), 2.59-2.50 (m, 1H), 2.49 (s, 3H), 2.45-2.35 (m, 1H).

Example 1.24. Preparation of 1'-methyl-3,4-dihydrospiro[[1,4]oxazino[4,3-b]indazole-1,4'-piperidin]-1'-ium chloride (24)

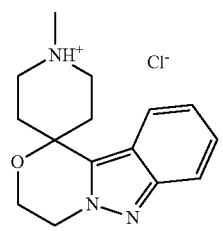

Compound 24 was prepared using a procedure analogous to that described for compound 23 but using tert-butyl 4-oxopiperidine-1-carboxylate in place of tert-butyl methyl (2-oxoethyl)carbamate in the procedure of Example 1.1. (160 mg, white solid); MS (ESI): m/z 258 [M+H]$^+$; 1H-NMR (400 MHz, CDCl$_3$): δ 7.75 (d, J=8.5 Hz, 1H), 7.66 (d, J=8.7 Hz, 1H), 7.31-7.24 (m, 1H), 7.04 (ddd, J=8.4, 6.7, 0.7 Hz, 1H), 4.51-4.41 (m, 2H), 4.23-4.11 (m, 2H), 2.79 (dd, J=6.8, 5.4 Hz, 2H), 2.51-2.40 (m, 4H), 2.38 (s, 3H), 2.07-1.94 (m, 2H).

Example 1.25. Preparation of (2R)-2-((R)-3,4-dihydro-1H-[1,4]oxazino[4,3-b]indazol-1-yl)-4-methylmorpholin-4-ium chloride (2S)

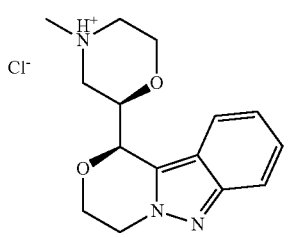

Compound 25 was prepared using a procedure analogous to that described for compound 1 but using intermediate I-29 in place of intermediate I-7 in the procedure of Example 1.1. (160 mg, white solid); MS (ESI): m/z 274 [M+H]$^+$; 1H-NMR (400 MHz, CDCl$_3$): δ 7.69 (dd, J=12.1, 8.6 Hz, 2H), 7.32-7.24 (m, 1H), 7.04 (dd, J=7.9, 7.2 Hz, 1H), 5.17 (s, 1H), 4.55 (ddd, J=13.4, 9.3, 4.1 Hz, 1H), 4.50-4.35 (m, 2H), 4.24 (dt, J=10.4, 2.2 Hz, 1H), 4.06-3.94 (m, 1H), 3.88 (dd, J=11.5, 2.3 Hz, 1H), 3.64 (td, J=11.5, 2.4 Hz, 1H), 2.82 (d, J=11.2 Hz, 1H), 2.63 (d, J=11.6 Hz, 1H), 2.29 (s, 3H), 2.21 (t, J=10.9 Hz, 1H), 2.17-2.06 (m, 1H).

Example 1.26. Preparation of (2R)-2-((S)-3,4-di-hydro-1H-[1,4]oxazino[4,3-b]indazol-1-yl)-4-methylmorpholin-4-ium chloride (26)

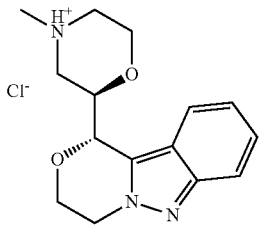

26

Compound 26 was prepared using a procedure analogous to that described for compound 1 but using intermediate I-30 in place of intermediate I-7 in the procedure of Example 1.1. (160 mg, white solid); MS (ESI): m/z 274 [M+H]⁺; 1H-NMR (400 MHz, CDCl₃): δ 7.74-7.63 (m, 2H), 7.35-7.26 (m, 1H), 7.09-7.02 (m, 1H), 5.30 (d, J=4.5 Hz, 1H), 4.61-4.49 (m, 1H), 4.49-4.39 (m, 2H), 4.26 (ddd, J=10.3, 4.5, 2.3 Hz, 1H), 4.10-3.97 (m, 2H), 3.81 (td, J=11.5, 2.5 Hz, 1H), 2.67 (d, J=11.7 Hz, 1H), 2.58-2.48 (m, 1H), 2.22 (s, 3H), 2.21-2.14 (m, 2H).

Example 1.27. Preparation of N-((3,4-dihydro-1H-[1,4]oxazino[4,3-b]indazol-1-yl)methyl)-N-methyl-propan-2-aminium chloride (27)

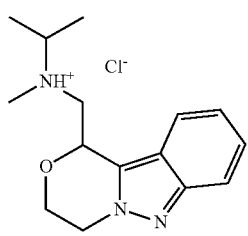

27

Example 1.28. Preparation of N-((3,4-dihydro-1H-[1,4]oxazino[4,3-b]indazol-1-yl)methyl)-N-methyl-ethanaminium chloride (28)

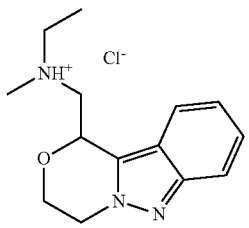

28

Compound 28 was prepared using a procedure analogous to that described for compound 3 but using compound 18 in place of compound 1 in the procedure of Example 1.F. (130 mg, white solid); MS (ESI): m/z 246 [M+H]⁺; ¹H NMR (400 MHz, MeOD): δ 8.17-8.01 (m, 1H), 7.82-7.63 (m, 2H), 7.49-7.36 (m, 1H), 6.03 (s, 1H), 4.84-4.72 (m, 1H), 4.72-4.57 (m, 2H), 4.42-4.30 (m, 1H), 4.14 (m, 1H), 3.87 (m, 1H), 3.53 (m, 2H), 3.11 (dd, J=55.7, 1.5 Hz, 3H), 1.46 (dt, J=33.4, 7.3 Hz, 3H).

Example 1.29. Preparation of N-((3,4-dihydro-1H-[1,4]oxazino[4,3-b]indazol-1-yl)methyl)-N-methyl-cyclobutanaminium chloride (29)

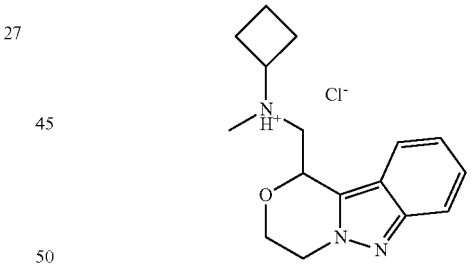

29

Compound 27 was prepared using a procedure analogous to that described for compound 3 but using compound 17 in place of compound 1 in the procedure of Example 1.F. (95 mg, white solid); MS (ESI): m/z 260 [M+H]⁺; 1H-NMR (400 MHz, MeOD): δ 8.16 (dd, J=28.7, 8.5 Hz, 1H), 7.83-7.70 (m, 2H), 7.51-7.43 (m, 1H), 6.20-6.01 (m, 1H), 4.89-4.74 (m, 1H), 4.76-4.59 (m, 2H), 4.39 (ddd, J=12.5, 8.6, 3.7 Hz, 1H), 4.15-3.75 (m, 3H), 3.17 (s, 2H), 2.95 (s, 1H), 1.47 (ddd, J=23.4, 12.7, 6.7 Hz, 6H).

Compound 29 was prepared using a procedure analogous to that described for compound 3 but using compound 16 in place of compound 1 in the procedure of Example 1.F. (130 mg, white solid); MS (ESI): m/z 272 [M+H]⁺; ¹H-NMR (400 MHz, CDCl₃): δ 7.68 (d, J=8.7 Hz, 1H), 7.61 (d, J=8.5 Hz, 1H), 7.32-7.27 (m, 1H), 7.11-7.03 (m, 1H), 5.34 (d, J=8.1 Hz, 1H), 4.62-4.50 (m, 1H), 4.50-4.38 (m, 2H), 4.12-4.00 (m, 1H), 2.96 (m, 2H), 2.81 (dd, J=13.7, 9.2 Hz, 1H), 2.37 (s, 3H), 2.09-1.91 (m, 3H), 1.77-1.58 (m, 3H).

Example 1.30. Preparation of (+/−)-rel-(R)-1-((R)-3,4-dihydro-1H-[1,4]oxazino[4,3-b]indazol-1-yl)ethanaminium chloride (30)

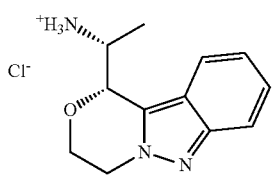

30

Compound 30 was prepared using a procedure analogous to that described for compound 3 but using intermediate I-32 in place of intermediate I-8 in the procedure of Example 1.3. (55.0 mg, white solid); MS (ESI): m/z 218 [M+H]$^+$; 1H NMR (400 MHz, d$^4$-methanol): δ 7.80 (d, J=8.4 Hz, 1H), 7.70 (d, J=9.1 Hz, 1H), 7.52 (t, J=7.6 Hz, 1H), 7.28 (t, J=7.5 Hz, 1H), 5.58-5.63 (m, 1H), 4.51-4.75 (m, 3H), 4.36-4.46 (m, 1H), 4.18-4.29 (m, 1H), 1.12 (d, J=6.9 Hz, 3H).

Example 1.31. Preparation of (+/−)-rel-(R)-1-((R)-3,4-dihydro-1H-[1,4]oxazino[4,3-b]indazol-1-yl)-N-methylethanaminium chloride (31)

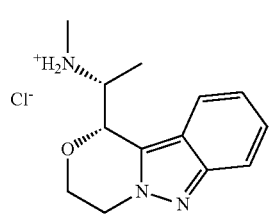

31

Compound 31 was prepared using a procedure analogous to that described for compound 3 but using intermediate I-34 in place of intermediate I-8 in the procedure of Example 1.3. (300 mg, white solid); MS (ESI): m/z 232 [M+H]$^+$; 1H-NMR (400 MHz, d$^4$-methanol): δ 7.79 (d, J=8.6 Hz, 1H), 7.68 (d, J=8.7 Hz, 1H), 7.45 (t, J=7.7 Hz, 1H), 7.23 (t, J=7.5 Hz, 1H), 5.67-5.76 (m, 1H), 4.48-4.72 (m, 3H), 4.17-4.34 (m, 2H), 2.93 (s, 3H), 1.12 (d, J=6.8 Hz, 3H).

Example 1.32. Preparation of (+/−)-rel-(R)-1-((R)-3,4-dihydro-1H-[1,4]oxazino[4,3-b]indazol-1-yl)-N,N-dimethylethanaminium chloride (32)

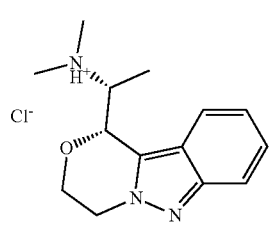

32

Compound 32 was prepared using a procedure analogous to that described for compound 3 but using compound 31 in place of compound 1 in the procedure of Example 1.F. (150 mg, white solid); MS (ESI): m/z 246 [M+H]$^+$; 1H-NMR (400 MHz, d$^4$-methanol): δ 7.98 (d, J=8.6 Hz, 1H), 7.74 (d, J=8.7 Hz, 1H), 7.61 (t, J=7.6 Hz, 1H), 7.36 (t, J=7.8 Hz, 1H), 6.00-6.10 (m, 1H), 4.68-4.80 (m, 1H), 4.55-4.67 (m, 2H), 4.35-4.45 (m, 1H), 4.28 (td, J=11.7, 3.5 Hz, 1H), 3.20 (s, 3H), 3.13 (s, 3H), 1.23 (d, J=6.8 Hz, 3H).

Example 1.33. Preparation of (+/−)-rel-(R)-1-((S)-3,4-dihydro-1H-[1,4]oxazino[4,3-b]indazol-1-yl)ethanaminium chloride (33)

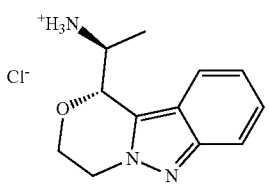

33

Compound 33 was prepared using a procedure analogous to that described for compound 1 but using intermediate I-33 in place of intermediate I-7 in the procedure of Example 1.1. (100 mg, white solid); MS (ESI): m/z 218 [M+H]$^+$; 1H-NMR (400 MHz, d$^4$-methanol): δ 7.93 (d, J=8.6 Hz, 1H), 7.74 (d, J=8.7 Hz, 1H), 7.57 (t, J=8.0 Hz, 1H), 7.33 (t, J=7.9 Hz, 1H), 5.52-5.56 (m, 1H), 4.53-4.73 (m, 3H), 4.32-4.41 (m, 1H), 4.18-4.28 (m, 1H), 1.67 (d, J=6.7 Hz, 3H).

Example 1.34. Preparation of (+/−)-rel-(R)-1-((S)-3,4-dihydro-1H-[1,4]oxazino[4,3-b]indazol-1-yl)-N-methylethanaminium chloride (34)

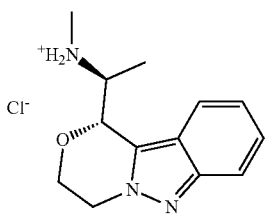

34

Compound 34 was prepared using a procedure analogous to that described for compound 31 but using intermediate I-33 in place of intermediate I-32 in the procedure of Example 1.Y. (110 mg, white solid); MS (ESI): m/z 232 [M+H]$^+$; 1H-NMR (400 MHz, d$^4$-Methanol): δ 7.95-8.12 (m, 1H), 7.59-7.86 (m, 2H), 7.35-7.54 (m, 1H), 5.57-5.73 (m, 1H), 4.56-4.86 (m, 3H), 4.21-4.42 (m, 2H), 2.62 (s, 3H), 1.72 (dd, J=6.9, 2.6 Hz, 3H).

Example 1.35. Preparation of 4-(3,4-dihydro-1H-[1,4]oxazino[4,3-b]indazol-1-yl)piperidin-1-ium chloride (35)

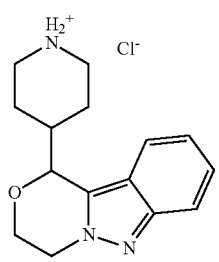

Compound 35 was prepared using a procedure analogous to that described for intermediate I-4 but using tert-butyl 4-formylpiperidine-1-carboxylate in place of tert-butyl methyl(2-oxoethyl)carbamate in the procedure of Example 1.B, followed by hydrochlorination using a procedure analogous to that described in Example 1.3. (293 mg, white solid); MS (ESI): m/z 258.1 [M+H]$^+$; $^1$H NMR (400 MHz, MeOH-d$_4$): δ 8.16 (d, 1H), 7.83-7.78 (m, 2H), 5.44 (s, 1H), 4.77-4.74 (m, 1H), 4.64-4.55 (m, 2H), 4.23-4.17 (m, 1H), 3.56 (d, 1H), 3.31-3.39 (m, 1H), 3.19-3.29 (m, 1H), 3.01-2.94 (m, 2H), 2.22-2.17 (m, 2H), 1.86-1.81 (m, 1H), 1.37 (d, 1H).

Example 1.36. Preparation of 3',4'-dihydrospiro[piperidine-4,1'-[1,4]oxazino[4,3-b]indazol]-1-ium chloride (36)

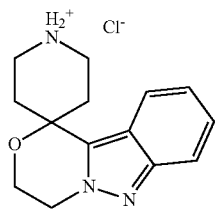

Compound 36 was prepared using a procedure analogous to that described for intermediate I-4 but using tert-butyl 4-oxopiperidine-1-carboxylate in place of tert-butyl methyl (2-oxoethyl)carbamate in the procedure of Example 1.B, followed by hydrochlorination using a procedure analogous to that described in Example 1.3. (175 mg, white solid); MS (ESI): m/z 244.2 [M+H]$^+$; $^1$H NMR (400 MHz, MeOH-d$_4$): δ 8.20 (d, 1H), 7.77-7.72 (m, 2H), 7.46 (t, 1H), 4.66 (br, 2H), 4.42 (br, 2H), 3.51 (br, 4H), 2.79 (br, 2H), 2.43 (d, 2H).

Example 1.37. Preparation of 3',4'-dihydro-4-azaspiro[bicyclo[2.2.1]heptane-2,1'-[1,4]oxazino[4,3-b]indazol]-4-ium chloride (37)

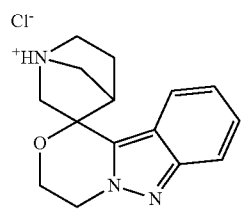

Compound 37 was prepared using a procedure analogous to that described for intermediate I-4 but using 1-azabicyclo[2.2.1]heptan-3-one in place of tert-butyl methyl(2-oxoethyl)carbamate in the procedure of Example 1.B, followed by hydrochlorination using a procedure analogous to that described in Example 1.3. (240 mg, white solid); MS (ESI): m/z 256.2 [M+H]$^+$; $^1$H NMR (400 MHz, MeOH-d$_4$); δ 7.81-7.79 (m, 1H), 7.74-7.72 (m, 1H), 7.56-7.52 (m, 1H), 7.38-7.33 (m, 1H), 4.65-4.57 (m, 3H), 4.46-4.39 (m, 1H), 4.13 (dd, 1H), 3.96-3.89 (m, 2H), 3.80-3.70 (m, 3H), 3.50 (dd, 1H), 2.36-2.27 (m, 1H), 2.13-2.06 (m, 1H).

Example 1.38. Preparation of (3S)-3-(3,4-dihydro-1H-[1,4]oxazino[4,3-b]indazol-1-yl)piperidin-1-ium (38)

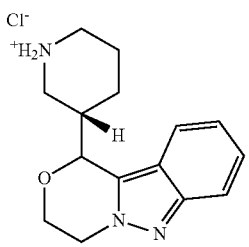

Compound 38 was prepared using a procedure analogous to that described for intermediate I-4 but using (S)-tert-butyl 3-formylpiperidine-1-carboxylate in place of tert-butyl methyl(2-oxoethyl)carbamate in the procedure of Example 1.B, followed by hydrochlorination using a procedure analogous to that described in Example 1.3. (120 mg, pale-brown solid); MS (ESI): m/z 258.0 [M+H]$^+$; $^1$H NMR (400 MHz, MeOH-d$_4$) δ 8.03-7.96 (m, 1H), 7.77-7.66 (m, 2H), 7.44-7.39 (m, 1H), 5.48-5.44 (m, 1H), 4.74-4.66 (m, 1H), 4.58-4.53 (m, 2H), 4.21-4.13 (m, 1H), 3.69-3.68 (m, 0.4H), 3.41-3.30 (m, 1.6H), 3.06-2.88 (m, 3H), 2.17-1.89 (m, 2.6H), 1.76-1.61 (m, 0.8H), 1.38-1.29 (m, 0.6H).

Example 1.39. Preparation of (1-methyl-3,4-di-hydro-1H-[1,4]oxazino[4,3-b]indazol-1-yl)methan-aminium chloride (39)

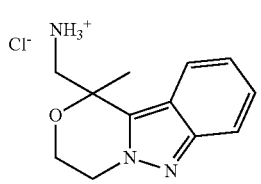

39

Compound 39 was prepared using a procedure analogous to that described for intermediate I-4 but using Cert-butyl (2-oxopropyl)carbamate in place of tert-butyl methyl(2-oxoethyl)carbamate in the procedure of Example 1.B, followed by hydrochlorination using a procedure analogous to that described in Example 1.3. (80 mg, pale-brown solid); MS (ESI): m/z 218.1 [M+H]$^+$; $^1$H NMR (400 MHz, MeOH-d$_4$) δ 8.06 (d, 1H), 7.80-7.71 (m, 2H), 7.48-7.43 (m, 1H), 4.76-4.69 (m, 1H), 4.66-4.60 (m, 1H), 4.51-4.40 (m, 2H), 3.86 (d, 1H), 3.67-3.65 (m, 1H), 1.92 (s, 3H).

Example 1.40. Preparation of 3',4'-dihydrospiro[azetidine-3,1'-[1,4]oxazino[4,3-b]indazol]-1-ium chloride (40)

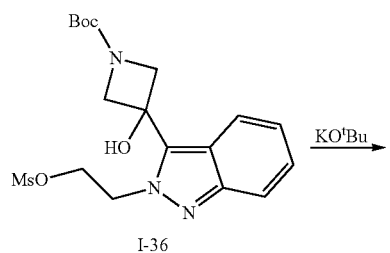

I-36

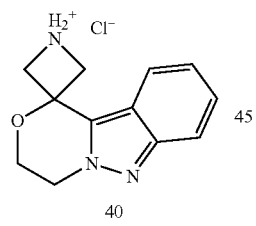

40

To a solution of intermediate I-36 (440 mg, 1.07 mmol) in tetrahydrofuran (20 mL) was added potassium tert-butoxide (0.36 g, 3.21 mmol) at 0° C. The mixture was stirred at 0° C. for 2 hrs and quenched with 10 ml of water. The crude reaction mixture was extracted with ethyl acetate (3×30 mL), the combined organic phase was dried over sodium sulfate and solids were removed by filtration. The filtrate was concentrated in vacuo and purified by preparative TLC (ethyl acetate:petrol ether=2:1) to give a white foamy solid. To the solid was added 5 ml of HCl-Methanol (3 N) and the reaction mixture was stirred at room temperature for 4 hrs and concentrated in vacuo to give compound 40. (92 mg, 35%, pale-brown solid); MS (ESI): m/z 216.1 [M+H]$^+$; $^1$H NMR (400 MHz, MeOH-d$_4$) δ 7.86-7.85 (m, 1H), 7.59-7.58 (m, 1H), 7.40-7.35 (m, 1H), 7.22-7.17 (m, 1H), 4.79-4.78 (m, 2H), 4.40-4.38 (m, 2H), 4.33-4.32 (m, 2H), 4.25-4.23 (m, 2H).

Example 1.41. Preparation of (1R)-2-cyclobutyl-1-(3,4-dihydro-1H-[1,4]oxazino[4,3-b]indazol-1-yl)ethan-1-aminium (41)

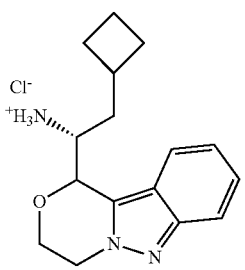

41

Compound 41 was prepared using a procedure analogous to that described for intermediate I-4 but using (R)-tert-butyl (1-cyclobutyl-3-oxopropan-2-yl)carbamate in place of tert-butyl methyl(2-oxoethyl)carbamate in the procedure of Example 1.B, followed by hydrochlorination using a procedure analogous to that described in Example 1.3. (97 mg, pale-brown solid); MS (ESI): m/z 272.1 [M+H]$^+$; $^1$H NMR (400 MHz, MeOH-d$_4$) δ 7.90-7.83 (m, 1H), 7.77-7.75 (m, 1H), 7.65-7.63 (m, 1H), 7.39-7.34 (m, 1H), 5.69 & 5.60 (s & s, 1H), 4.78-4.57 (m, 3H), 4.26-4.06 (m, 2H), 2.71-2.65 (m, 0.5H), 2.33-2.19 (m, 2H), 2.09-1.76 (m, 4.5H), 1.68-1.48 (m, 1H), 1.38-1.25 (m, 1H).

Example 1.42. Preparation of (2R)-2-(3,4-dihydro-1H-[1,4]oxazino[4,3-b]indazol-1-yl)morpholin-4-ium chloride (42)

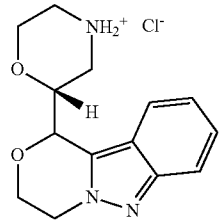

42

Compound 42 was prepared using a procedure analogous to that described for intermediate I-4 but using (R)-tert-butyl 2-formylmorpholine-4-carboxylate in place of tert-butyl methyl(2-oxoethyl)carbamate in the procedure of Example 1.B, followed by hydrochlorination using a procedure analogous to that described in Example 1.3. (41 mg, pale-white solid); MS (ESI): m/z 260.0 [M+H]$^+$; $^1$H NMR (400 MHz, MeOH-d$_4$) δ 8.05-8.03 (m, 1H), 7.74-7.61 (m, 2H), 7.44-7.32 (m, 1H), 5.65-5.47 (m, 1H), 4.77-4.46 (m, 4H), 4.30-4.21 (m, 1.4H), 4.04-3.90 (m, 1H), 3.85-3.78 (m, 0.6H), 3.66-3.64 (m, 0.6H), 3.49-3.13 (m, 3.4H).

Example 1.43. Preparation (3S)-3-(3,4-dihydro-1H-[1,4]oxazino[4,3-b]indazol-1-yl)morpholin-4-ium chloride (43)

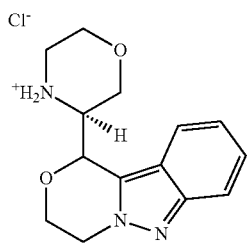

43

Compound 43 was prepared using a procedure analogous to that described for intermediate I-4 but using (S)-tert-butyl 3-formylmorpholine-4-carboxylate in place of tert-butyl methyl(2-oxoethyl)carbamate in the procedure of Example 1.B, followed by hydrochlorination using a procedure analogous to that described in Example 1.3. (75 mg, pale-white solid); MS (ESI): m/z 260.1 [M+H]$^+$; $^1$H NMR (400 MHz, MeOH-d$_4$) δ 7.95-7.94 (m, 1H), 7.73-7.72 (m, 1H), 7.56-7.55 (m, 1H), 7.34-7.33 (m, 1H), 4.71-4.50 (m, 4H), 4.27-4.20 (m, 1H), 4.06-4.04 (m, 1H), 3.81-3.72 (m, 2H), 3.61-3.43 (m, 3H).

Example 1.44. Preparation of 3',4'-dihydrospiro[pyrrolidine-3,1'-[1,4]oxazino[4,3-b]indazol]-1-ium chloride (44)

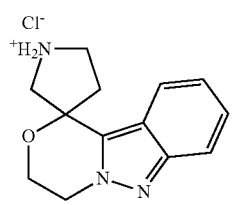

44

Compound 44 was prepared using a procedure analogous to that described for intermediate I-4 but using tert-butyl 3-oxopyrrolidine-1-carboxylate in place of tert-butyl methyl (2-oxoethyl)carbamate in the procedure of Example 1.B, followed by hydrochlorination using a procedure analogous to that described in Example 1.3. (90 mg, pale-yellow solid); MS (ESI): m/z 229.9 [M+H]$^+$; $^1$H NMR (400 MHz, MeOH-d$_4$) δ 8.08-8.07 (m, 1H), 7.75-7.74 (m, 1H), 7.65-7.63 (m, 1H), 7.40-7.38 (m, 1H), 4.66-4.65 (m, 2H), 4.46-4.45 (m, 2H), 3.89-3.65 (m, 4H), 2.80-2.79 (m, 2H).

Example 1.45. Preparation of (+/−)—(S)-3-((R)-3,4-dihydro-1H-[1,4]oxazino[4,3-b]indazol-1-yl)morpholin-4-ium chloride (45)

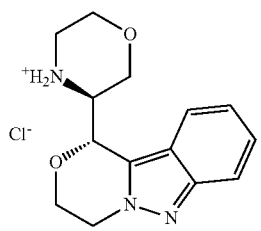

45

Compound 45 was prepared using a procedure analogous to that described for compound 1 but using intermediate I-39 in place of intermediate I-7 in the procedure of Example 1.1. (0.19 g); MS (ESI): m/z 260 [M+H]$^+$; $^1$H-NMR (400 MHz, MeOD-d4) δ 7.66-7.60 (m, 2H), 7.29-7.25 (m, 1H), 7.07-7.03 (m, 1H), 5.15-5.14 (d, J=3.6 Hz, 1H), 4.48-4.35 (m, 3H), 3.95-3.94 (m, 1H), 3.77-3.73 (m, 1H), 3.66-3.64 (m, 1H), 3.50-3.49 (m, 1H), 3.44-3.38 (m, 2H), 3.06-2.99 (m, 2H).

Example 1.46. Preparation of (+/−)—(S)-3-((S)-3,4-dihydro-1H-[1,4]oxazino[4,3-b]indazol-1-yl)morpholin-4-ium chloride (46)

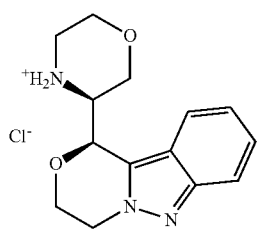

46

Compound 46 was prepared using a procedure analogous to that described for compound 1 but using intermediate I-40 in place of intermediate I-7 in the procedure of Example 1.1. (0.12 g); MS (ESI): m/z 260 [M+H]$^+$; $^1$H-NMR (400 MHz, MeOD-d4) δ 7.70-7.60 (m, 2H), 7.31-7.29 (m, 1H), 7.11-7.09 (m, 1H), 5.13-5.12 (d, J=3.6 Hz, 1H), 4.65-4.55 (m, 1H), 4.48-4.38 (m, 2H), 4.01-3.98 (m, 2H), 3.86-3.78 (m, 2H), 3.68-3.64 (m, 1H), 3.58-3.52 (m, 1H), 2.96-2.84 (m, 2H).

Example 1.47. Preparation of (+/−)-(3S,4R)-3-((R)-3,4-dihydro-1H-[1,4]oxazino[4,3-b]indazol-1-yl)-4-methylmorpholin-4-ium chloride (47)

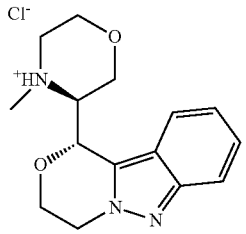

47

Compound 47 was prepared using a procedure analogous to that described for compound 3 but using intermediate I-39 in place of compound 1 in the procedure of Example 1.F. (0.08 g); MS (ESI): m/z 274 [M+H]$^+$; $^1$H NMR (400 MHz, MeOD-d4) δ 7.71-7.68 (d, J=8.8 Hz, 1H), 7.64-7.62 (d, J=8.8 Hz, 1H), 7.34-7.30 (m, 1H), 7.12-7.10 (d, J=8.8 Hz, 1H), 5.62 (d, J=2.4 Hz, 1H), 4.52-4.45 (m, 3H), 4.02-3.94 (m, 1H), 3.79-3.78 (m, 1H), 3.70-3.69 (m, 1H), 3.60-3.54 (m, 1H), 3.35-3.34 (m, 1H), 3.02-3.00 (m, 1H), 2.89-2.86 (m, 1H), 2.60 (s, 3H), 2.55-2.54 (m, 1H).

Example 1.48. Preparation of (+/−)-(3S,4R)-3-((S)-3,4-dihydro-1H-[1,4]oxazino[4,3-b]indazol-1-yl)-4-methylmorpholin-4-ium chloride (48)

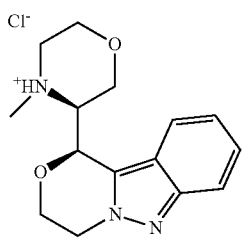

48

Compound 48 was prepared using a procedure analogous to that described for compound 3 but using intermediate I-40 in place of compound 1 in the procedure of Example 1.F. (0.11 g); MS (ESI): m/z 274 [M+H]$^+$; $^1$H-NMR (400 MHz, MeOD-d4) δ 7.98-7.95 (d, J=8.4 Hz, 1H), 7.66-7.63 (d, J=8.4 Hz, 1H), 7.29-7.27 (m, 1H), 7.07-7.05 (m, 1H), 5.21 (s, 1H), 4.56-4.39 (m, 3H), 3.96-3.95 (m, 1H), 3.90-3.87 (m, 1H), 3.78-3.76 (m, 1H), 3.61-3.60 (m, 1H), 3.52-3.47 (m, 1H), 2.99-2.97 (m, 1H), 2.76-2.74 (m, 1H), 2.45-2.44 (m, 1H), 2.13 (s, 3H).

Example 1.49. Preparation of N—(((S)-3,4-dihydro-1H-[1,4]oxazino[4,3-b]indazol-1-yl)methyl)-N-methylethanaminium chloride (49)

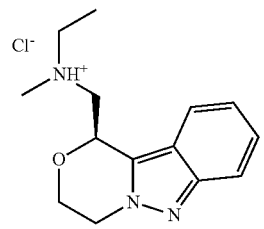

49

Compound 49 was prepared using a procedure analogous to that described for compound 3 but using acetaldehyde in place of paraformaldehyde in the procedure of Example 1.F. (1.5 g, Yield 88%); MS (ESI): m/z 246 [M+H]$^+$; $^1$H-NMR (400 MHz, MeOD-d4) δ 8.13-8.08 (m, 1H), 7.78-7.76 (m, 1H), 7.74-7.68 (m, 1H), 7.45-7.42 (m, 1H), 6.05-6.03 (m, 1H), 4.80-4.74 (m, 1H), 4.69-4.61 (m, 2H), 4.40-4.33 (m, 1H), 4.21-4.17 (m, 1H), 4.11-4.08 (m, 1H), 3.93-3.86 (m, 1H), 3.69-3.64 (m, 0.41H), 3.55-3.36 (m, 1.57H), 3.18 (s, 1.77H), 3.04 (s, 1.21H), 1.50 (t, J=7.3 Hz, 1.24H), 1.42 (t, J=7.3 Hz, 1.76H).

Example 1.50. Preparation of N—(((R)-3,4-dihydro-1H-[1,4]oxazino[4,3-b]indazol-1-yl)methyl)-N-methylethanaminium chloride (50)

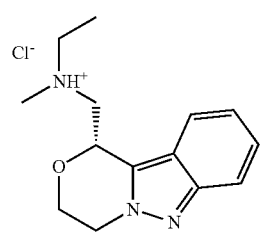

50

Compound 50 was prepared using a procedure analogous to that described for compound 4 but using acetaldehyde in place of paraformaldehyde in the procedure of Example 1.F. (1.4 g); MS (ESI): m/z 246 [M+H]$^+$; $^1$H NMR (400 MHz, MeOD-d4) δ 8.12-8.07 (m, 1H), 7.78-7.77 (m, 1H), 7.76-7.69 (m, 1H), 7.46-7.42 (m, 1H), 6.04-6.00 (m, 1H), 4.80-4.73 (m, 1H), 4.69-4.61 (m, 2H), 4.40-4.33 (m, 1H), 4.21-4.09 (m, 1H), 4.11-4.07 (m, 1H), 3.93-3.80 (m, 1H), 3.67-3.64 (m, 0.41H), 3.49-3.36 (m, 1.63H), 3.18 (s, 1.78H), 3.04 (s, 1.19H), 1.50 (t, J=7.3 Hz, 1.23H), 1.42 (t, J=7.3 Hz, 1.77H).

Example 1.51. Preparation of 1-(4,5-dihydro-1H,3H-[1,4]oxazepino[4,3-b]indazol-1-yl)-N-methyl-methanaminium chloride (51)

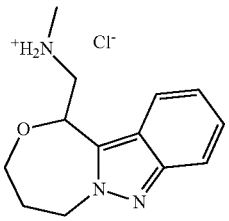

Compound 51 was prepared using a procedure analogous to that described for compound 1 but using intermediate I-46 in place of intermediate I-7 in the procedure of Example 1.1. (60 mg, white solid); MS (ESI): m/z 232 [M+H]$^+$; $^1$H-NMR (400 MHz, MeOD-d4) δ 7.98 (d, J=8.4 Hz, 1H), 7.71 (d, J=8.4 Hz, 1H), 7.63 (t, J=8.4 Hz, 1H), 7.38 (t, J=8.4 Hz, 1H), 5.70 (d, J=10.0 Hz, 1H), 5.00-4.98 (m, 2H), 4.48-4.43 (m, 1H), 4.22-4.00 (m, 3H), 2.96 (s, 3H), 2.27 (br-s, 2H).

Example 1.52. Preparation of 1-(4,5-dihydro-1H,3H-[1,4]oxazepino[4,3-b]indazol-1-yl)-N,N-dimethylmethanaminium chloride (52)

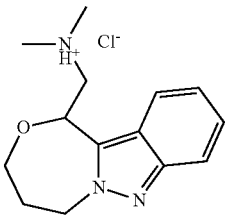

Compound 52 was prepared using a procedure analogous to that described for compound 3 but using compound 51 in place of compound 1 in the procedure of Example 1.F. (128 mg, white solid); MS (ESI): m/z 246 [M+H]$^+$; $^1$H-NMR (400 MHz, MeOD-d4) δ 8.05 (d, J=8.7 Hz, 1H), 7.79-7.67 (m, 2H), 7.51-7.40 (m, 1H), 6.01-5.83 (m, 1H), 5.05 (s, 2H), 4.47 (dt, J=12.4, 4.6 Hz, 1H), 4.33-4.19 (m, 3H), 3.18 (d, J=5.7 Hz, 6H), 2.36-2.22 (m, 2H).

Example 1.53. Preparation N-((4,5-dihydro-1H,3H-[1,4]oxazepino[4,3-b]indazol-1-yl)methyl)-N-methylethanaminium chloride (53)

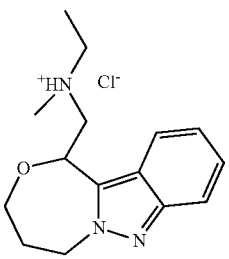

Compound 53 was prepared using a procedure analogous to that described for compound 52 but using acetaldehyde in place of paraformaldehyde in the procedure of Example 1.F. (118 mg, white solid); MS (ESI): m/z 260 [M+H]$^+$; $^1$H-NMR (400 MHz, MeOD-d4) δ 7.65 (d, J=8.8 Hz, 1H), 7.58 (d, J=8.8 Hz, 1H), 7.24 (t, J=8.8 Hz, 1H), 7.06-7.02 (m, 1H), 5.20-5.17 (m, 1H), 4.92-4.89 (m, 1H), 4.73-4.65 (m, 1H), 4.35-4.30 (m, 1H), 3.82-3.78 (m, 1H), 3.27-3.21 (m, 1H), 3.07-3.03 (m, 1H), 2.68-2.59 (m, 2H), 2.42 (s, 3H), 2.17-1.85 (m, 2H), 1.11 (t, I=7.2 Hz, 3H).

Example 1.54. Preparation of N-((4,5-dihydro-1H,3H-[1,4]oxazepino[4,3-b]indazol-1-yl)methyl)-N-methylpropan-2-aminium chloride (54)

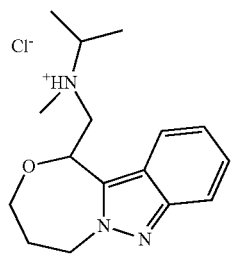

Compound 54 was prepared using a procedure analogous to that described for compound 52 but using acetone in place of paraformaldehyde in the procedure of Example 1.F. (142 mg, white solid); MS (ESI): m/z 274 [M+H]$^+$; $^1$H-NMR (400 MHz, CDCl$_3$) δ 7.59-7.50 (m, 1H), 7.51-7.43 (m, 1H), 7.18-7.07 (m, 1H), 7.01-6.87 (m, 1H), 5.05 (dd, J=5.5, 3.4 Hz, 1H), 4.87-4.71 (m, 1H), 4.61-4.46 (m, 1H), 4.24-4.13 (m, 1H), 3.66 (dd, J=13.5, 9.1 Hz, 1H), 3.13-2.99 (m, 1H), 2.94 (d, J=13.5 Hz, 1H), 2.89-2.76 (m, 1H), 2.29 (d, J=2.9 Hz, 3H), 1.94 (dd, J=41.8, 2.9 Hz, 2H), 0.92 (ddd, J=9.5, 6.6, 2.8 Hz, 6H).

Example 1.55. Preparation of N-((4,5-dihydro-1H,3H-[1,4]oxazepino[4,3-b]indazol-1-yl)methyl)-N-methylcyclobutanaminium chloride (55)

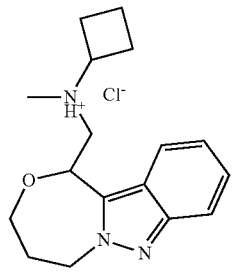

Compound 55 was prepared using a procedure analogous to that described for compound 52 but using cyclobutanone in place of paraformaldehyde in the procedure of Example 1.F. (99 mg, white solid); MS (ESI): m/z 286 [M+H]$^+$; $^1$H-NMR (400 MHz, D$_2$O) δ 7.56 (dd, J=18.2, 8.7 Hz, 2H), 7.33 (dd, J=8.2, 7.4 Hz, 1H), 7.16-7.09 (m, 1H), 5.49 (dd, J=11.1, 2.9 Hz, 1H), 4.76-4.72 (m, 2H), 4.33 (dt, J=12.5, 3.8

Hz, 1H), 4.14-3.83 (m, 4H), 2.88 (d, J=10.5 Hz, 3H), 2.48-2.12 (m, 4H), 2.00 (dd, J=18.7, 4.1 Hz, 2H), 1.77 (dd, J=18.2, 10.2 Hz, 2H).

Example 1.56. Preparation of (4,5-dihydro-1H,3H-[1,4]oxazepino[4,3-b]indazol-1-yl)methanaminium chloride (56)

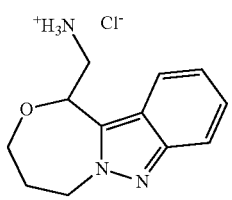

Compound 56 was prepared using a procedure analogous to that described for compound 1 but using intermediate I-51 in place of intermediate I-7 in the procedure of Example 1.1. (89 mg, white solid); MS (ESI): m/z 218 [M+H]+. 1H-NMR (400 MHz, MeOD-d4) δ 7.76 (d, J=8.7 Hz, 1H), 7.67 (d, J=8.8 Hz, 1H), 7.51-7.41 (m, 1H), 7.29-7.20 (m, 1H), 5.38 (dd, J=10.8, 3.0 Hz, 1H), 4.91-4.79 (m, 2H), 4.43 (s, 1H), 4.14-3.98 (m, 2H), 3.84 (s, 1H), 2.26-2.10 (m, 2H).

Example 1.57. Preparation of N-((4,5-dihydro-1H, 3H-[1,4]oxazepino[4,3-b]indazol-1-yl)methyl)ethanaminium chloride (57)

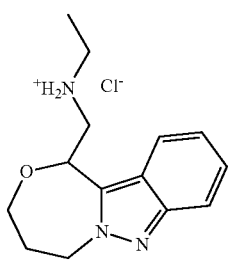

Compound 57 was prepared using a procedure analogous to that described for compound 1 but using intermediate I-52 in place of intermediate I-7 in the procedure of Example 1.1. (72 mg, white solid) as white solid; MS (ESI): m/z 246 [M+H]+; 1H-NMR (400 MHz, MeOD-d4) δ 7.90 (d, J=8.7 Hz, 1H), 7.70 (d, J=8.8 Hz, 1H), 7.59-7.51 (m, 1H), 7.34 (dd, J=8.1, 7.0 Hz, 1H), 5.58 (dd, J=10.8, 2.8 Hz, 1H), 4.92 (s, 2H), 4.55-4.37 (m, 1H), 4.22-4.04 (m, 2H), 4.01 (d, J=11.2 Hz, 1H), 3.33-3.27 (m, 2H), 2.24 (dd, J=10.5, 5.8 Hz, 2H), 1.46 (t, J=7.3 Hz, 3H).

Example 1.58. Preparation of 1-(6,7-dihydro-9H-thieno[3',2':3,4]pyrazolo[5,1-c][1,4]oxazin-9-yl)-N-methylmethanaminium chloride (58)

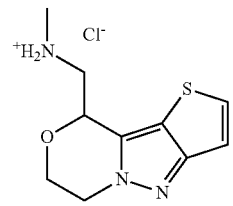

Compound 58 was prepared using a procedure analogous to that described for compound 1 but using intermediate I-58 in place of intermediate I-7 in the procedure of Example 1.1. (53 mg, white solid); MS (ESI): m/z 224 [M+H]+; 1H-NMR (400 MHz, CDCl3): δ 7.60 (d, J=5.2 Hz, 1H), 7.12 (d, J=5.2 Hz, 1H), 5.44-5.42 (m, 1H), 4.54-4.38 (m, 3H), 4.27-4.21 (m, 1H), 3.74-3.70 (m, 1H), 3.54-3.49 (m, 1H), 2.82 (s, 3H).

Example 1.59. Preparation of 1-(6,7-dihydro-9H-thieno[3',2':3,4]pyrazolo[5,1-c][1,4]oxazin-9-yl)-N, N-dimethylmethanaminium chloride (59)

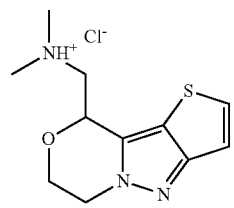

Compound 59 was prepared using a procedure analogous to that described for compound 3 but using compound 58 in place of compound 1 in the procedure of Example 1.F. (56 mg, white solid); MS (ESI): m/z 238 [M+H]+; 1H-NMR (400 MHz, CDCl3): δ 7.31 (d, J=5.5 Hz, 1H), 7.05 (d, J=5.5 Hz, 1H), 4.98 (t, J=6.8 Hz, 1H), 4.48-4.34 (m, 2H), 4.33-4.26 (m, 1H), 4.07 (td, J=11.4, 3.5 Hz, 1H), 2.79 (qd, J=12.5, 6.8 Hz, 2H), 2.40 (s, 6H).

Example 1.60. Synthesis of (6,7-dihydro-9H-thieno[3',2':3,4]pyrazolo[5,1-c][1,4]oxazin-9-yl)methanaminium chloride (60)

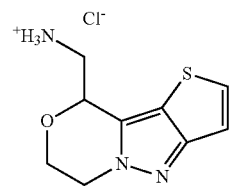

Compound 60 was prepared using a procedure analogous to that described for compound 1 but using intermediate I-63 in place of intermediate I-7 in the procedure of Example 1.1.

(56 mg, white solid); MS (ESI): m/z 210 [M+H]⁺; ¹H-NMR (400 MHz, MeOD-d4): δ 7.63 (d, J=5.3 Hz, 1H), 7.13 (d, J=5.4 Hz, 1H), 5.38 (dd, J=7.7, 2.8 Hz, 1H), 4.57-4.45 (m, 2H), 4.44-4.36 (m, 1H), 4.29-4.19 (m, 1H), 3.65 (dd, J=13.4, 2.7 Hz, 1H), 3.42 (dd, J=13.5, 7.8 Hz, 1H).

Example 1.61. Synthesis of 1-((methylammonio)methyl)-3,4-dihydro-1H-pyrido[3',4':3,4]pyrazolo[5,1-c][1,4]oxazin-8-ium chloride (61)

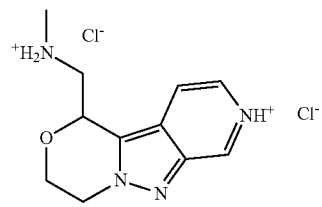

61

Compound 61 was prepared using a procedure analogous to that described for compound 1 but using intermediate I-68 in place of intermediate I-7 in the procedure of Example 1.1. (55.4 mg, yellow solid); MS (ESI): m/z 219 [M+H]⁺; ¹H-NMR (400 MHz, MeOD-d4): δ 9.79 (s, 1H), 8.54 (d, J=6.8 Hz, 1H), 8.28 (d, J=6.8 Hz, 1H), 5.82-5.79 (m, 1H), 4.86-4.84 (m, 2H), 4.67-4.63 (m, 1H), 4.39-4.35 (m, 1H), 4.07-4.03 (m, 1H), 3.71-3.68 (m, 1H), 2.89 (s, 3H).

Example 1.62. Synthesis of 1-((dimethylammonio)methyl)-3,4-dihydro-1H-pyrido[3',4':3,4]pyrazolo[5,1-c][1,4]oxazin-8-ium chloride (62)

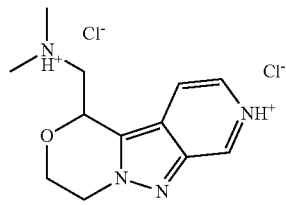

62

Compound 62 was prepared using a procedure analogous to that as described for compound 3 but using compound 61 in place of compound 1 in the procedure of Example 1.F. (60 mg, yellow solid); MS (ESI): m/z 233 [M+H]⁺, ¹H-NMR (400 MHz, MeOD-d4): δ 9.79 (s, 1H), 8.58 (d, J=6.8 Hz, 1H), 8.28 (d, J=6.8 Hz, 1H), 5.98-5.94 (m, 1H), 5.45-5.42 (m, 1H), 4.68-4.65 (m, 1H), 4.58-4.55 (m, 1H), 4.44-4.38 (m, 2H), 4.30-4.22 (m, 2H), 4.19-4.13 (m, 1H), 3.07 (s, 3H), 3.02 (s, 3H).

Example 1.63. Preparation of 1-(aziridin-1-ylmethyl)-3,4-dihydro-1H-[1,4]oxazino[4,3-b]indazole (63)

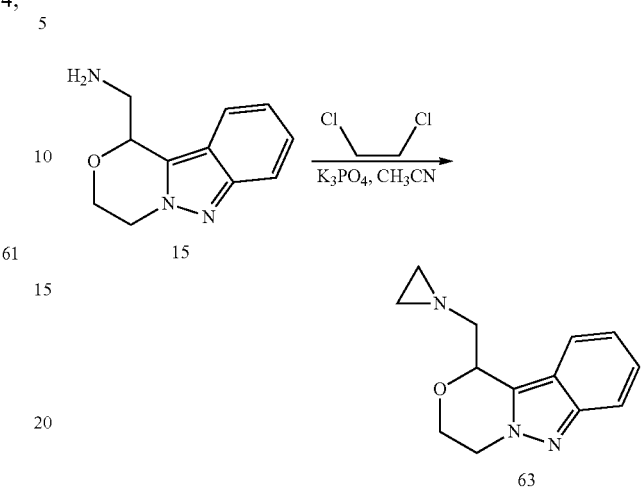

To a solution of compound 15 (0.34 g, 1.67 mmol) in a mixture of dichloroethane/acetonitrile (4 mL/2 mL) was added solid K₃PO₄ (354 mg, 1.67 μmol) in a sealed tube. The reaction mixture was stirred at 130° C. for 3 hrs. The crude reaction mixture was filtered, the filtrate was concentrated in vacuo and the residue was purified by silica gel chromatography. Compound 63 was obtained as yellow oil (90 mg, 20%, MS (ESI): m/z 230 [M+H]⁺. ¹H-NMR (500 MHz CDCl₃): δ 7.68 (d, J=8.8 Hz, 1H), 7.55 (d, J=8.5 Hz, 1H), 7.36-7.26 (m, 1H), 7.13-7.00 (m, 1H), 5.55-5.32 (m, 1H), 4.61-4.56 (m, 1H), 4.51-4.47 (m, 2H), 4.18-4.05 (m, 1H), 3.11-3.08 (m, 1H), 2.76-2.72 (m, 1H), 1.89-1.87 (m, 2H), 1.36-1.30 (m, 2H).

Example 1.64. Preparation of (2S)-2-(3,4-dihydro-1H-[1,4]oxazino[4,3-b]indazol-1-yl)azetidin-1-ium chloride (64)

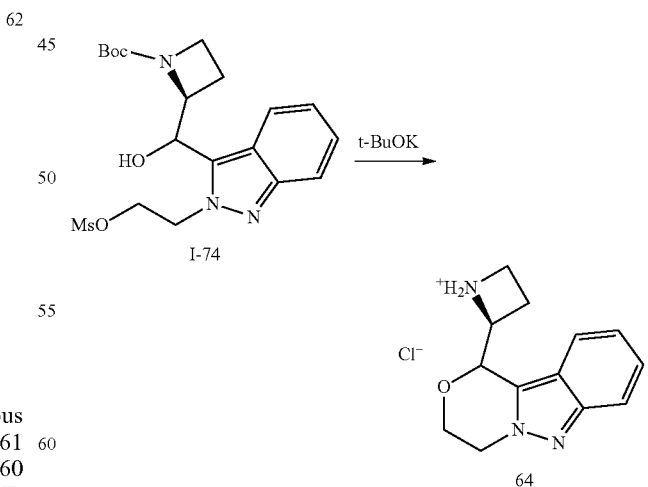

Compound 64 was prepared using a procedure analogous to that described for compound 40 but using intermediate I-71 in place of intermediate I-36 in the procedure of Example 1.40. (129 mg as white solid). MS (ESI): m/z 230

[M+H]⁺. 1H-NMR (500 MHz, DMSO-d6): δ 7.78 (d, J=8.5 Hz, 1H), 7.62 (d, J=8.5 Hz, 1H), 7.28 (t, J=8.5 Hz, 1H), 7.08 (t, J=8.5 Hz, 1H), 5.52 (s, 1H), 5.33 (br-s, 1H), 4.74-4.69 (m, 1H), 4.54-4.51 (m, 1H), 4.44-4.42 (m, 1H), 4.21-4.16 (m, 1H), 3.88-3.85 (m, 1H), 3.75-3.72 (m, 1H), 2.79-2.76 (m, 1H), 2.57-2.54 (m, 1H).

Example 1.65. Preparation of ((2S)-2-(3,4-dihydro-1H-[1,4]oxazino[4,3-b]indazol-1-yl)-1-methylazetidin-1-ium chloride (65)

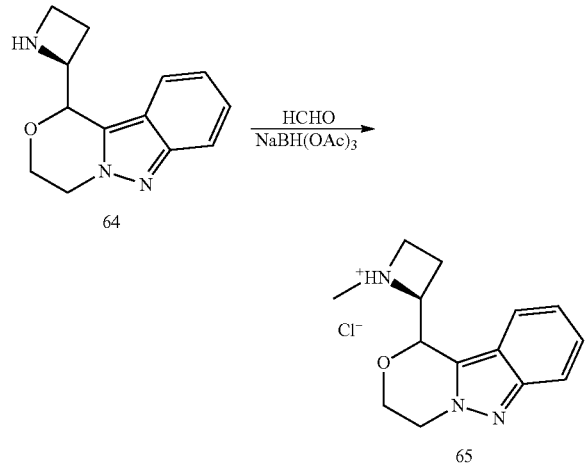

Compound 65 was prepared using a procedure analogous to that described for compound 3 but using compound 64 in place of compound 1 in the procedure of Example 1.F. (49.8 mg, as colorless oil). MS (ESI): m/z 244 [M+H]⁺. 1H-NMR (500 MHz, CD₃OD): δ 7.79 (d, J=8.4 Hz, 1H), 7.67 (d, J=8.4 Hz, 1H), 7.40 (t, J=8.5 Hz, 1H), 7.22 (t, J=8.5 Hz, 1H), 5.57 (s, 1H), 5.43-5.41 (m, 1H), 4.74-4.65 (m, 2H), 4.54-4.51 (m, 1H), 4.33-4.26 (m, 1H), 4.19-4.14 (m, 1H), 3.99-3.92 (m, 1H), 3.03-2.97 (m, 1H), 2.74-2.70 (m, 1H), 2.49 (s, 3H).

Example 1.66. Preparation of 3-(3,4-dihydro-1H-[1,4]oxazino[4,3-b]indazol-1-yl)azetidin-1-ium chloride (66)

Compound 66 was prepared using a procedure analogous to that described for compound 3, but using Cert-butyl 3-formylazetidine-1-carboxylate in place of tert-butyl methyl(2-oxoethyl)carbamate in the procedure of Example 1.B. MS (ESI): m/z 230 [M+H]⁺. ¹H NMR (500 MHz, CD₃OD): δ 7.80 (m, 1H), 7.68 (m, 1H), 7.52 (m, 1H), 7.26 (m, 1H), 5.47 (brs, 1H), 4.71-4.68 (m, 3H), 4.40-4.30 (m, 3H), 4.05-3.87 (m, 3H).

Example 1.67. Preparation of 3-(3,4-dihydro-1H-[1,4]oxazino[4,3-b]indazol-1-yl)-1-methylazetidin-1-ium chloride (67)

Compound 67 was prepared using a procedure analogous to that described for compound 3, but using compound 66 in place of compound 1 in the procedure of Example 1.F. MS (ESI): m/z 244 [M+H]+. 1H NMR (400 MHz, CD₃OD): δ 7.87-7.80 (m, 1H), 7.69 (d, J=8.8 Hz, 1H), 7.58-7.54 (m, 1H), 7.33-7.28 (m, 1H), 5.55 (s, 1H), 4.81-4.58 (m, 4H), 4.35-4.29 (m, 2H), 4.13-3.98 (m, 3H), 2.92 (s, 3H).

Example 1.68. Preparation of (S)-1-(6,7-dihydro-9H-thieno[3',2':3,4]pyrazolo[5,1-c][1,4]oxazin-9-yl)-N-methylmethanamine (68) and (R)-1-(6,7-dihydro-9H-thieno[3',2':3,4]pyrazolo[5,1-c][1,4]oxazin-9-yl)-N-methylmethanamine (69)

Compound 58 (4.0 g, 17.9 mmol) was separated into its enantiomers 68 and 69 by chiral HPLC using column IC 20*250 mm, 5 μm (Daicel) and mobile phase CO₂/MeOH (0.2% NH₄OH)=65/35. The flow rate was 80 g/min, back pressure was 100 Bar and cycle time of stack injections was 5.3 min. Compound 68 (2.0 g, 50%, retention time 2.74 min) was obtained as colorless oil. MS (ESI): m/z 224 [M+H]⁺. ¹H-NMR (500 MHz, CD₃OD): δ 7.85 (d, J=5.0 Hz, 1H), 7.21 (d, J=5.0 Hz, 1H), 5.57-5.55 (m, 1H), 4.58-4.48 (m, 3H), 4.32-4.27 (m, 1H), 3.80-3.77 (m, 1H), 3.59-3.55 (m, 1H), 2.84 (s, 3H). Compound 69 (2.0 g, 50%, retention time 4.46 min) was obtained as white solid. MS (ESI): m/z 224 [M+H]⁺. ¹H-NMR (500 MHz, CD₃OD): δ 7.63 (d, J=5.0 Hz, 1H), 7.12 (d, J=5.0 Hz, 1H), 5.47-5.45 (m, 1H), 4.54-4.39 (m, 3H), 4.27-4.22 (m, 1H), 3.75-3.72 (m, 1H), 3.54-3.50 (m, 1H), 2.83 (s, 3H).

Example 2. Biological Assays

Example 2.1. Tail Suspension Test

The tail suspension test (TST) is a rodent screening test for potential (human) antidepressant drugs. It is based on the assumption that an animal will actively try to escape an aversive (stressful) stimulus. If escape is impossible, the animal will eventually stop trying ("give up"). In the TST, a mouse is suspended by the tail so that its body dangles in the air, head downward. Mice initially struggle to face upward and climb to a solid surface. When the animal stops struggling and hangs immobile it is considered to have "given up". Shorter periods of immobility are characteristic of anti-depressant-like activity. Accordingly, longer periods of immobility are considered indicative of a depressive-like state. It has been shown that treatment with an antidepressant drug will decrease the time the animal spends immobile. See generally L. Steru et al., *Psychopharmacology (Berl)*. 1985; 85(3):367-70; B. Thierry et al., *Psychopharmacology* 1986; 90:284-85.

Procedure.

Adult male CD1 mice (Charles River Laboratories) receive either vehicle (sterile water or saline, 10 mL/kg) or compound (30 mg/kg) by ip injection 30 min before being subjected to the Tail Suspension Test. In this test animals are suspended by the tail for 10 min during which the time spent immobile is measured.

| Compound | Mean Total Time Immobile (sec) | Standard Error of the Mean | p value (compound vs vehicle) |
|---|---|---|---|
| 2  | 76.6  | 25.9 | <0.0001 |
| 4  | 74.9  | 13.0 | <0.0001 |
| 6  | 175.2 | 35.1 | 0.020   |
| 7  | 132.9 | 20.7 | 0.0012  |
| 8  | 237.5 | 30.0 | 0.12    |
| 9  | 189.4 | 18.8 | 0.0078  |
| 22 | 374.0 | 27.8 | 0.73    |
| 27 | 144.2 | 34.5 | 0.0002  |
| 28 | 98.0  | 33.9 | <0.0001 |
| 29 | 115.0 | 25.1 | <0.0001 |
| 50 | 84.5  | 18.9 | 0.0005  |
| 61 | 162.0 | 26.6 | <0.0001 |
| 68 | 86.1  | 30.6 | <0.0001 |

Example 2.2. Neuropharmacological Assay (SmartCube™)

In order to further demonstrate the utility of the provided compounds to treat neurological and psychiatric diseases and disorders, exemplary compounds were evaluated using the neuropharmacological screen described in S. L. Roberds et al., *Front. Neurosci.* 2011 Sep. 9; 5:103 (doi: 10.3389/fnins.2011.00103) ("Roberds"). As reported in Roberds, because psychiatric diseases generally result from disorders of cell-cell communication or circuitry, intact systems are useful in detecting improvement in disease-relevant endpoints. These endpoints are typically behavioral in nature, often requiring human observation and interpretation. To facilitate testing of multiple compounds for behavioral effects relevant to psychiatric disease, PsychoGenics, Inc. (Tarrytown, N.Y., "PGI") developed SmartCube™, an automated system in which behaviors of compound-treated mice are captured by digital video and analyzed with computer algorithms. (D. Brunner et al., *Drug Discov. Today* 2002, 7:S107-S112). PGI Analytical Systems uses data from SmartCube™ to compare the behavioral signature of a test compound to a database of behavioral signatures obtained using a large set of diverse reference compounds. (The composition of the database as well as validation of the method is further described in Roberds). In this way, the neuropharmacological effects of a test compound can be predicted by similarity to major classes of compounds, such as antipsychotics, anxiolytics and antidepressants.

The SmartCube™ system produces an activity signature indicating the probability that the activity of the test compound at the administered dose matches a given class of neuropharmacological agents. (See, e.g., Roberds, FIGS. 2 and 3). The test compound is simultaneously compared against multiple classes of agents; thus, a separate probability is generated for each behavioral effect measured (e.g., anxiolytic activity, analgesic activity, etc.). In Table 2 and 2B, these probabilities are reported for each behavioral effect measured as follows:

| LOQ≤ | + | <5% |
| 5%≤ | ++ | <25% |
| 25%≤ | +++ | <50% |
| 50%≤ | ++++ | | where LOQ is the limit of quantification.

Provided compounds were dissolved in a mixture of Pharmasolve™ (N-methyl-2-pyrrolidone), polyethylene glycol and propylene glycol, and were injected i.p. 15 min. before the behavioral test. For each compound, injections were administered at 3 different doses. For each behavioral effect measured, results for the most efficacious dose(s) are presented.

TABLE 2

| Compound | DP | AX | SD | PS | MS | AD | CE | AG | XG | HA | UN |
|---|---|---|---|---|---|---|---|---|---|---|---|
| 1  | +    | ++ | +  | +  | +  | +  | +  | +   | +  | +    | +   |
| 2  | ++++ | ++ | +  | +  | +  | ++ | +  | +   | +  | ++++ | +   |
| 3  | ++   | +  | +  | ++ | +  | +  | +  | +   | +  | +    | +++ |
| 4  | ++++ | +  | +  | +  | +  | ++ | ++ | ++  | +  | ++   | ++  |
| 5  | ++   | +  | +  | +  | +  | +  | +  | ++  | +  | +    | +   |
| 6  | +++  | ++ | +  | ++ | +  | +  | ++ | ++  | +  | +    | +   |
| 7  | ++++ | +  | +  | +  | +  | +  | +  | ++  | +  | +    | +   |
| 8  | +++  | ++ | +  | ++ | +  | +  | ++ | ++  | ++ | +    | +   |
| 9  | ++   | +  | +  | +  | +  | ++ | ++ | ++  | +  | +    | +++ |
| 10 | ++++ | ++ | +  | ++ | +  | +  | +  | ++  | ++ | +    | +   |
| 11 | +++  | +  | ++ | ++ | +  | +  | +  | +   | +  | +    | +   |
| 12 | +    | +  | +  | +  | +  | +  | +  | +   | +  | +    | +   |
| 13 | ++   | ++ | +  | +  | ++ | +  | ++ | +++ | +  | +    | +   |

TABLE 2-continued

| Compound | DP | AX | SD | PS | MS | AD | CE | AG | XG | HA | UN |
|---|---|---|---|---|---|---|---|---|---|---|---|
| 14 | ++ | +++ | + | ++ | + | + | ++ | + | + | + | + |
| 15 | ++ | + | + | + | + | ++++ | + | ++ | + | + | + |
| 16 | + | + | + | + | + | + | + | + | + | + | + |
| 17 | ++ | ++ | + | + | + | + | + | + | + | + | ++ |
| 18 | + | ++ | + | ++ | + | + | ++ | ++ | + | + | + |
| 19 | +++ | ++ | + | + | + | + | ++ | ++ | + | + | + |
| 20 | ++ | +++ | + | ++ | + | + | ++ | ++ | + | + | + |
| 21 | ++ | ++ | + | ++ | + | + | + | ++ | + | + | + |
| 22 | ++++ | ++ | + | + | + | ++ | + | + | + | ++ | ++ |
| 23 | ++ | ++++ | + | + | + | + | ++ | ++ | + | + | + |
| 24 | ++ | ++ | + | ++ | + | + | ++ | ++ | + | + | + |
| 25 | ++ | ++ | + | + | + | ++ | + | ++ | + | + | + |
| 26 | ++ | + | + | + | + | + | + | ++ | + | + | + |
| 27 | ++++ | + | + | + | + | + | + | ++ | + | + | + |
| 28 | ++++ | ++ | + | + | + | + | ++ | + | + | ++ | ++ |
| 29 | +++ | ++ | + | + | + | + | ++ | + | + | ++ | + |
| 30 | ++ | +++ | + | + | + | ++ | + | ++ | + | ++ | + |
| 31 | ++ | +++ | + | ++ | + | + | ++ | ++ | + | + | +++ |
| 32 | ++ | ++ | + | +++ | + | + | ++ | + | + | + | ++ |
| 33 | ++ | ++ | + | + | + | ++++ | + | ++ | + | ++ | +++ |
| 34 | + | ++ | + | + | + | + | + | + | + | + | + |
| 35 | + | + | + | + | + | + | + | + | + | + | + |
| 36 | +++ | ++ | ++ | ++ | + | + | ++ | ++ | + | + | ++ |
| 37 | ++ | ++ | ++ | ++ | + | + | ++ | ++ | + | + | +++ |
| 38 | + | ++ | + | ++ | ++ | + | + | ++ | + | + | + |
| 39 | ++ | ++ | + | + | + | + | + | + | + | + | + |
| 40 | ++ | +++ | ++ | ++ | + | + | ++ | ++ | + | + | + |
| 41 | + | + | + | + | + | + | + | + | + | + | + |
| 42 | + | + | + | + | + | + | + | + | + | + | + |
| 43 | + | + | + | + | + | + | + | + | + | + | + |
| 44 | ++ | +++ | + | ++ | + | + | ++ | ++ | + | + | + |
| 45 | + | + | + | + | + | + | + | + | + | + | + |
| 46 | + | ++ | ++ | ++ | + | + | + | ++ | + | + | ++ |
| 47 | + | ++ | + | + | + | + | + | ++ | + | + | + |
| 48 | + | + | + | + | + | + | + | + | + | + | + |
| 49 | ++ | ++ | ++ | + | + | + | ++ | +++ | + | + | + |
| 50 | ++++ | +++ | + | + | + | ++ | + | + | + | ++ | + |
| 51 | +++ | ++ | + | + | + | ++ | + | + | + | + | + |
| 52 | ++ | ++ | + | + | + | + | + | + | + | + | ++ |
| 53 | ++ | ++ | ++ | + | + | + | + | + | + | + | ++ |
| 54 | + | ++ | + | + | + | + | + | + | + | + | + |
| 55 | + | ++ | + | + | + | + | + | + | + | + | +++ |
| 56 | + | + | + | + | + | + | + | + | + | + | + |
| 57 | + | + | + | + | + | + | + | + | + | + | + |
| 58 | ++++ | ++ | ++ | + | + | ++ | + | + | + | ++ | + |
| 59 | ++ | ++ | + | ++ | + | + | ++ | ++ | + | + | +++ |
| 60 | ++ | +++ | ++ | + | + | ++ | + | + | + | + | + |
| 61 | ++++ | + | + | + | + | ++ | + | + | + | ++ | ++ |
| 62 | + | ++ | + | + | + | + | + | + | + | + | + |
| I-4 | ++++ | +++ | ++ | + | + | ++ | + | + | + | ++ | + |
| 63 | ++ | + | ++ | + | + | + | + | +++ | + | + | + |
| 64 | ++ | ++ | + | + | + | ++++ | + | ++ | + | + | +++ |
| 65 | ++ | ++ | ++ | + | + | + | ++ | +++ | ++ | + | + |
| 66 | ++ | ++ | + | + | + | + | + | ++ | + | + | + |
| 67 | ++ | ++ | + | + | + | + | + | + | + | + | + |
| 68 | ++++ | ++ | ++ | + | + | ++ | + | ++ | + | ++++ | ++ |
| 69 | ++ | ++ | + | + | + | + | + | + | + | + | ++ |

DP: anti-depressant;
AX: anxiolytic;
SD: sedative hypnotic;
PS: anti-psychotic;
MS: mood stabilizer;
AD: ADHD;
CE: cognitive enhancer;
AG: analgesic;
XG: anxiogenic;
HA: hallucinogen;
UN: uncharacterized CNS activity Some embodiments of the present invention are enumerated below. In such presentations, an embodiment reciting a "compound" with reference to another enumerated embodiment either that itself explicitly recites "or a pharmaceutically acceptable salt thereof" or that refers ultimately to an enumerated embodiment that does, is intended to encompass both free compounds and pharmaceutically acceptable salts thereof. As a convention, the phrase "or a pharmaceutically acceptable salt thereof" is explicitly recited when the structural formula of the compound is explicitly recited, but no difference in inclusion or exclusion of pharmaceutically acceptable salts is thereby intended. For example, both embodiments 1 and 2 are intended to encompass both the free compounds and pharmaceutically acceptable salts thereof.

1. A compound of Formula (I):

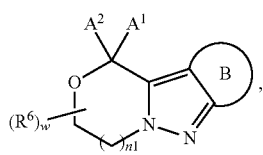

or a pharmaceutically acceptable salt thereof, wherein:
Ring B is a 6-membered aromatic ring, which ring is unsubstituted or substituted with 1 to 4 substituents independently selected from halo, —OH, —NH$_2$, —CH$_3$, —CH$_2$F, —CHF$_2$ and —CF$_3$; or is a 5- or 6-membered heteroaromatic ring having 1 to 3 ring heteroatoms independently selected from O, N and S, which ring is unsubstituted or substituted with 1 to 3 substituents independently selected from halo, —OH, —NH$_2$, —CH$_3$, —CH$_2$F, —CHF$_2$ and —CF$_3$;
A$^1$ is —H or C$_{1-3}$ alkyl; and
A$^2$ is —C(R$^2$)(R$^8$)—(CH$_2$)$_p$—N(R$^9$)R$^{10}$;
or A$^1$ and A$^2$, together with the carbon atom to which they are attached, form

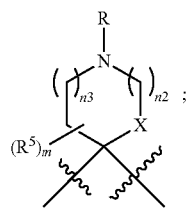

m is 0, 1 or 2;
n1 is 1 or 2;
n2 is 0 or 1;
n3 is 0 or 1;
p is 0 or 1;
R is —H or C$_1$-C$_3$ alkyl; or R is —CH$_2$—(X), —CH$_2$CH$_2$—(X), —CH$_2$—(Z) or —CH$_2$CH$_2$—(Z);
each instance of R$^5$ independently is halo, —CH$_3$ or ethyl;
each instance of R$^6$ independently is halo or —CH$_3$;
R$^7$ is —H or C$_1$-C$_3$ alkyl;
R$^8$ is —H or C$_1$-C$_3$ alkyl which is unsubstituted or substituted with C$_3$-C$_6$ cycloalkyl;
R$^9$ is —H, C$_1$-C$_4$ alkyl or C$_3$-C$_6$ cycloalkyl; and
R$^{10}$ is —H or C$_1$-C$_3$ alkyl;

or R$^9$ and R$^8$, together with the atoms to which they are attached, form

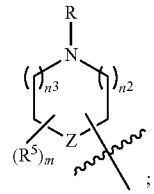

or R$^9$ and R$^{10}$, together with the nitrogen atom to which they are attached, form

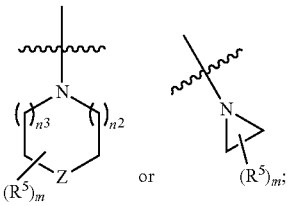

w is 0, 1 or 2;
X is CH or CH$_2$; and
Z is CH, CH$_2$ or O.

2. The compound of embodiment 1, wherein A$^1$ is —H or —CH$_3$.
3. The compound of embodiment 2, wherein A$^1$ is —H.
4. The compound of any of embodiments 1-3, wherein:
w is 1 or 2; and
each instance of R$_6$ is —CH$_3$.
5. The compound of any of embodiments 1-3, wherein w is 0.
6. The compound of any of embodiments 1-5, wherein n1 is 1.
7. The compound of any of embodiments 1-5, wherein n1 is 2.
8. The compound of any of embodiments 1-7 of Formula (I-1):

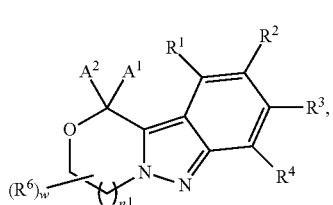

or a pharmaceutically acceptable salt thereof, wherein:
R$^1$, R$^2$, R$^3$ and R$^4$ are independently —H, halo, —OH, —NH$_2$, —CH$_3$, —CH$_2$F, —CHF$_2$ or —CF$_3$.
9. The compound of embodiment 8, wherein at least two of R$^1$, R$^2$, R$^3$ and R$^4$ are —H.
10. The compound of embodiment 8, wherein at least three of R$^1$, R$^2$, R$^3$ and R$^4$ are —H.
11. The compound of embodiment 8, wherein R$^1$, R$^2$, R$^3$ and R$^4$ are independently —H, halo or —CH$_3$.
12. The compound of embodiment 11, wherein R$^1$, R$^2$, R$^3$ and R$^4$ are independently —H, —F or —Cl.

13. The compound of any of embodiments 1-7 of Formula (I-2):

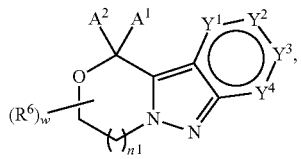

(I-2)

or a pharmaceutically acceptable salt thereof, wherein:
$Y^1$ is N or $CR^{1\prime}$;
$Y^2$ is N or $CR^{2\prime}$;
$Y^3$ is N or $CR^{3\prime}$; and
$Y^4$ is N or $CR^{4\prime}$;
wherein 1 to 3 of $Y^1$, $Y^2$, $Y^3$ and $Y^4$ are N; and
$R^{1\prime}$, $R^{2\prime}$, $R^{3\prime}$ and $R^{4\prime}$ are independently —H, halo, —OH, —NH$_2$, —CH$_3$, —CH$_2$F, —CHF$_2$ or —CF$_3$.

14. The compound of embodiment 13, wherein $R^{1\prime}$, $R^{2\prime}$, $R^{3\prime}$ and $R^{4\prime}$ are independently —H, halo or —CH$_3$.

15. The compound of embodiment 14, wherein $R^{1\prime}$, $R^{2\prime}$, $R^{3\prime}$ and $R^{4\prime}$ are independently —H, —F or —Cl.

16. The compound of any of embodiments 13-15, wherein 2 of $Y^1$, $Y^2$, $Y^3$ and $Y^4$ are N.

17. The compound of embodiment 16, wherein at least 1 of $Y^1$, $Y^2$, $Y^3$ and $Y^4$ is CH.

18. The compound of any of embodiments 13-15, wherein 1 of $Y^1$, $Y^2$, $Y^3$ and $Y^4$ is N.

19. The compound of embodiment 18, wherein at least 2 of $Y^1$, $Y^2$, $Y^3$ and $Y^4$ are CH.

20. The compound of embodiment 18 or 19, wherein $Y^3$ is N.

21. The compound of any of embodiments 1-7 of Formula (I-3):

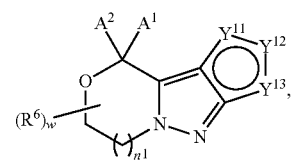

(I-3)

or a pharmaceutically acceptable salt thereof, wherein:
$Y^{11}$ is $CR^{1\prime\prime}$ or a heteroatom selected from O, S, N and $NR^{11}$;
$Y^{12}$ is $CR^{2\prime\prime}$ or a heteroatom selected from O, S, N and $NR^{12}$; and
$Y^{13}$ is $CR^{3\prime\prime}$ or a heteroatom selected from O, S, N and $NR^{13}$;
wherein at least one of $Y^{11}$, $Y^{12}$ and $Y^{13}$ is a heteroatom;
$R^{1\prime\prime}$, $R^{2\prime\prime}$ and $R^{3\prime\prime}$ are independently —H, halo, —OH, —NH$_2$, —CH$_3$, —CH$_2$F, —CHF$_2$ or —CF$_3$; and
$R^{11}$, $R^{12}$ and $R^{13}$ are independently —H or —CH$_3$.

22. The compound of embodiment 21, wherein $R^{1\prime\prime}$, $R^{2\prime\prime}$ and $R^{3\prime\prime}$ are independently —H, halo or —CH$_3$.

23. The compound of embodiment 22, wherein $R^{1\prime\prime}$, $R^{2\prime\prime}$ and $R^{3\prime\prime}$ are independently —H, —F or —Cl.

24. The compound of any of embodiments 21-23, wherein 2 of $Y^{11}$, $Y^{12}$ and $Y^{13}$ are heteroatoms.

25. The compound of embodiment 24, wherein 1 of $Y^{11}$, $Y^{12}$ and $Y^{13}$ is $C_H$.

26. The compound of any of embodiments 21-23, wherein 1 of $Y^{11}$, $Y^{12}$ and $Y^{13}$ is a heteroatom.

27. The compound of embodiment 26, wherein at least 1 of $Y^{11}$, $Y^{12}$ and $Y^{13}$ is CH.

28. The compound of embodiment 26 or 27, wherein $Y^{11}$ is S.

29. The compound of any of embodiments 8-12, of formula (II-1):

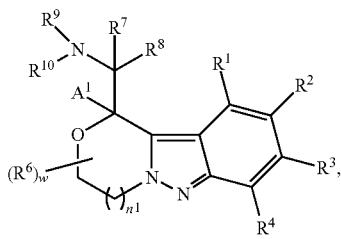

(II-1)

or a pharmaceutically acceptable salt thereof.

30. The compound of embodiment 29, of formula (II-1a):

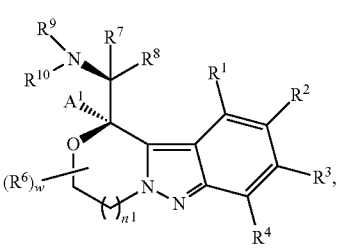

(II-1a)

or a pharmaceutically acceptable salt thereof.

31. The compound of embodiment 29, of formula (II-1b):

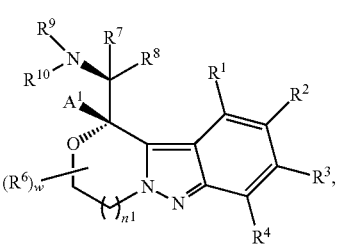

(II-1b)

or a pharmaceutically acceptable salt thereof.

32. The compound of any of embodiments 13-20, of formula (II-2):

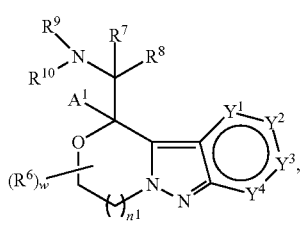

(II-2)

or a pharmaceutically acceptable salt thereof.

33. The compound of any of embodiments 21-28, of formula (II-3):

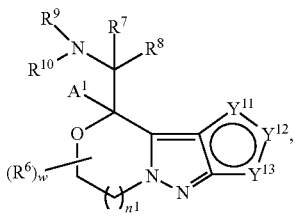

(II-3)

or a pharmaceutically acceptable salt thereof.

34. The compound of any of embodiments 29-33, wherein:
R$^7$ is —H or —CH$_3$; and
R$^8$ is H or unsubstituted C$_1$-C$_3$ alkyl.

35. The compound of embodiment 34, wherein:
R$^7$ is —H; and
R$^8$ is —H or —CH$_3$.

36. The compound of any of embodiments 29-35, wherein:
R$^9$ is —H, C$_1$-C$_3$ alkyl, cyclopropyl or cyclobutyl; and
R$^{10}$ is —H or C$_1$-C$_2$ alkyl.

37. The compound of embodiment 36, wherein:
R$^9$ is —H or C$_1$-C$_3$ alkyl; and
R$^{10}$ is —H or —CH$_3$.

38. The compound of any of embodiments 29-35, wherein R$^9$ and R$^{10}$, together with the nitrogen atom to which they are attached, form

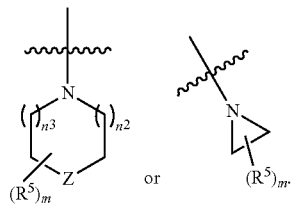

39. The compound of embodiment 38, wherein m is 0.

40. The compound of any of embodiments 8-12, of formula (III-1):

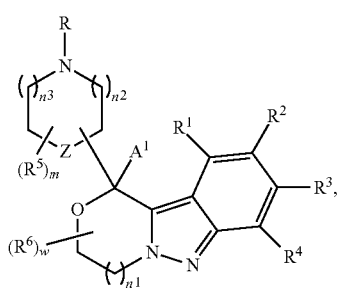

(III-1)

or a pharmaceutically acceptable salt thereof.

41. The compound of embodiment 40, of formula (III-1a):

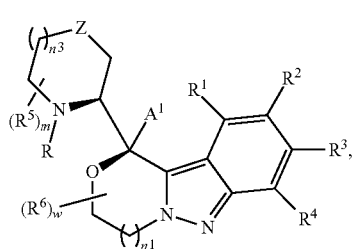

(III-1a)

or a pharmaceutically acceptable salt thereof.

42. The compound of embodiment 40, of formula (III-1b):

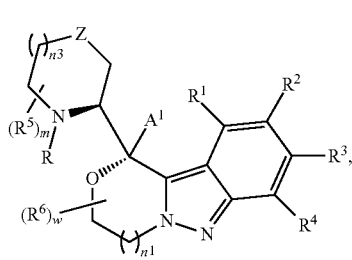

(III-1b)

or a pharmaceutically acceptable salt thereof.

43. The compound of embodiment 40, of formula (III-1c):

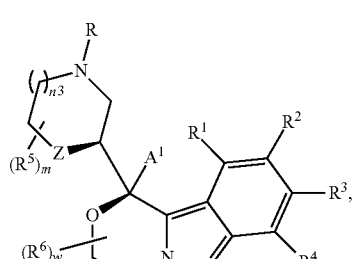

(III-1c)

or a pharmaceutically acceptable salt thereof.

44. The compound of embodiment 40, of formula (III-1d):

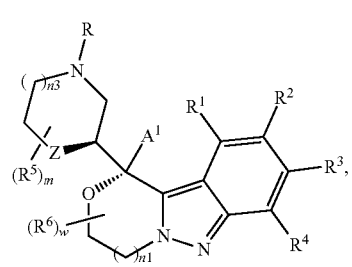

(III-1d)

or a pharmaceutically acceptable salt thereof.

45. The compound of any of embodiments 40-44, wherein R is —H or —CH$_3$.

46. The compound of any of embodiments 40-45, wherein m is 0.

47. The compound of any of embodiments 8-12, of formula (IV-1):

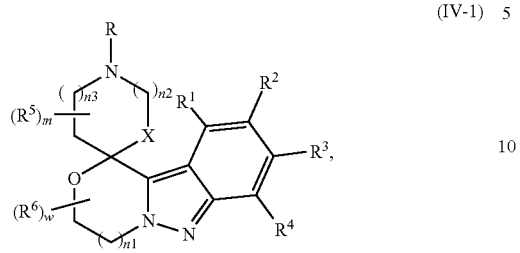

or a pharmaceutically acceptable salt thereof.
48. The compound of embodiment 47, wherein R is —H or —CH$_3$.
49. The compound of embodiment 47, wherein R is —CH$_2$—(X).
50. The compound of any of embodiments 47-49, wherein m is 0.
51. A composition comprising the compound of any of embodiments 1-50 and a pharmaceutically acceptable carrier, adjuvant, or vehicle.
52. A method for treating a neurological or psychiatric disorder in a patient, comprising administering to said patient an effective amount of the compound according to any of embodiments 1-50.
53. The method according to embodiment 52, wherein the neurological or psychiatric disorder is depression, bipolar disorder, pain, schizophrenia, obsessive compulsive disorder, addiction, social disorder, attention deficit hyperactivity disorder, an anxiety disorder, autism or cognitive impairments.
54. The method according to embodiment 53, wherein the neurological or psychiatric disorder is depression.
55. The method according to embodiment 54, wherein the depression is treatment-resistant depression (TRD), major depressive disorder (MDD), unipolar depression, bipolar depression or depression associated with another disease or disorder.

What is claimed is:
1. A compound of Formula (I):

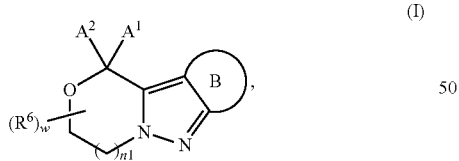

or a pharmaceutically acceptable salt thereof, wherein:
Ring B is a 6-membered aromatic ring, which ring is unsubstituted or substituted with 1 to 4 substituents independently selected from halo, —OH, —NH$_2$, —CH$_3$, —CH$_2$F, —CHF$_2$ and —CF$_3$; or is a 5- or 6-membered heteroaromatic ring having 1 to 3 ring heteroatoms independently selected from O, N and S, which ring is unsubstituted or substituted with 1 to 3 substituents independently selected from halo, —OH, —NH$_2$, —CH$_3$, —CH$_2$F, —CHF$_2$ and —CF$_3$;
A$^1$ is —H or C$_{1-3}$ alkyl; and
A$^2$ is —C(R$^7$)(R$^8$)—(CH$_2$)$_p$—N(R$^9$)R$^{10}$;
or A$^1$ and A$^2$, together with the carbon atom to which they are attached, form

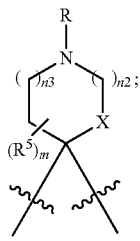

m is 0, 1 or 2;
n1 is 1 or 2;
n2 is 0 or 1;
n3 is 0 or 1;
p is 0 or 1;
R is —H or C$_1$-C$_3$ alkyl; or R is —CH$_2$—(X), —CH$_2$CH$_2$—(X), —CH$_2$—(Z) or —CH$_2$CH$_2$—(Z);
each instance of R$^5$ independently is halo, —CH$_3$ or ethyl;
each instance of R$^6$ independently is halo or —CH$_3$;
R$^7$ is —H or C$_1$-C$_3$ alkyl;
R$^8$ is —H or C$_1$-C$_3$ alkyl which is unsubstituted or substituted with C$_3$-C$_6$ cycloalkyl;
R$^9$ is —H, C$_1$-C$_4$ alkyl or C$_3$-C$_6$ cycloalkyl; and
R$^{10}$ is —H or C$_1$-C$_3$ alkyl;
or R$^9$ and R$^8$, together with the atoms to which they are attached, form

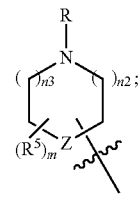

or R$^9$ and R$^{10}$, together with the nitrogen atom to which they are attached, form

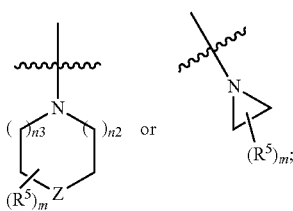

w is 0, 1 or 2;
X is CH or CH$_2$; and
Z is CH, CH$_2$ or O.
2. The compound of claim 1, or a pharmaceutically acceptable salt thereof, wherein A$^1$ is —H.
3. The compound of claim 1, or a pharmaceutically acceptable salt thereof, wherein w is 0.
4. The compound of claim 1, or a pharmaceutically acceptable salt thereof, wherein n1 is 1.
5. The compound of claim 1, or a pharmaceutically acceptable salt thereof, wherein n1 is 2.

6. The compound of claim 1 of Formula (I-1):

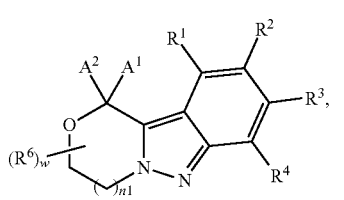

(I-1)

or a pharmaceutically acceptable salt thereof, wherein:
$R^1$, $R^2$, $R^3$ and $R^4$ are independently —H, halo, —OH, —NH$_2$, —CH$_3$, —CH$_2$F, —CHF$_2$ or —CF$_3$.

7. The compound of claim 6, or a pharmaceutically acceptable salt thereof, wherein $R^1$, $R^2$, $R^3$ and $R^4$ are independently —H, —F or —Cl.

8. The compound of claim 1 of Formula (I-2):

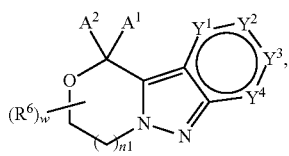

(I-2)

or a pharmaceutically acceptable salt thereof, wherein:
$Y^1$ is N or $CR^{1'}$;
$Y^2$ is N or $CR^{2'}$;
$Y^3$ is N or $CR^{3'}$; and
$Y^4$ is N or $CR^{4'}$;
wherein 1 to 3 of $Y^1$, $Y^2$, $Y^3$ and $Y^4$ are N; and
$R^{1'}$, $R^{2'}$, $R^{3'}$, and $R^{4'}$ are independently —H, halo, —OH, —NH$_2$, —CH$_3$, —CH$_2$F, —CHF$_2$ or —CF$_3$.

9. The compound of claim 8, or a pharmaceutically acceptable salt thereof, wherein $Y^3$ is N.

10. The compound of claim 1 of Formula (I-3):

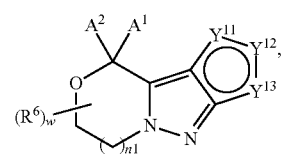

(I-3)

or a pharmaceutically acceptable salt thereof, wherein:
$Y^{11}$ is $CR^{1''}$ or a heteroatom selected from O, S, N and $NR^{11}$;
$Y^{12}$ is $CR^{2''}$ or a heteroatom selected from O, S, N and $NR^{12}$; and
$Y^{13}$ is $CR^{3''}$ or a heteroatom selected from O, S, N and $NR^{13}$;
wherein at least one of $Y^{11}$, $Y^{12}$ and $Y^{13}$ is a heteroatom;
$R^{1''}$, $R^{2''}$ and $R^{3''}$ are independently —H, halo, —OH, —NH$_2$, —CH$_3$, —CH$_2$F, —CHF$_2$ or —CF$_3$; and
$R^{11}$, $R^{12}$ and $R^{13}$ are independently —H or —CH$_3$.

11. The compound of claim 10, or a pharmaceutically acceptable salt thereof, wherein $Y^{11}$ is S.

12. The compound of claim 6, of formula (II-1):

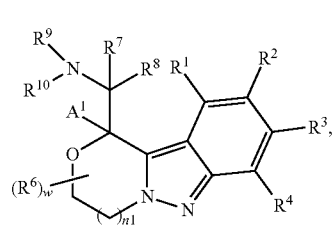

(II-1)

or a pharmaceutically acceptable salt thereof.

13. The compound of claim 12, of formula (II-1a):

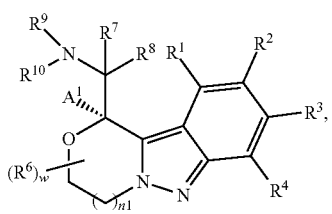

(II-1a)

or a pharmaceutically acceptable salt thereof.

14. The compound of claim 12, or a pharmaceutically acceptable salt thereof, wherein $R^9$ and $R^{10}$, together with the nitrogen atom to which they are attached, form

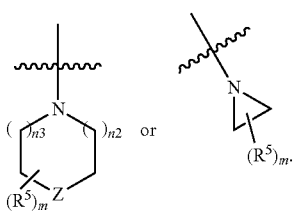

15. The compound of claim 6, of formula (III-1):

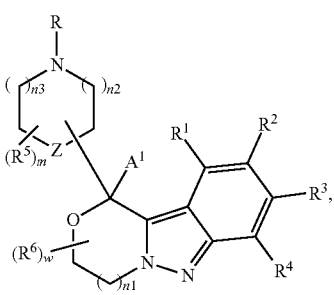

(III-1)

or a pharmaceutically acceptable salt thereof.

16. The compound of claim 15, of formula (III-1a):

(III-1a)

or a pharmaceutically acceptable salt thereof.

17. The compound of claim 6, of formula (IV-1):

(IV-1)

or a pharmaceutically acceptable salt thereof.

18. A composition comprising the compound of claim 1, or a pharmaceutically acceptable salt thereof, and a pharmaceutically acceptable carrier, adjuvant, or vehicle.

19. A method for treating a neurological or psychiatric disorder in a patient, comprising administering to said patient an effective amount of the compound according to claim 1, or a pharmaceutically acceptable salt thereof, wherein said neurological or psychiatric disorder is selected from depression, anxiety, psychosis, or attention-deficit hyperactivity disorder.

20. The method according to claim 19, wherein the neurological or psychiatric disorder is depression.

21. The method according to claim 20, wherein the depression is treatment-resistant depression (TRD), major depressive disorder (MDD), unipolar depression, bipolar depression or depression associated with another disease or disorder.

22. The compound of claim 1 selected from a compound shown below, or a pharmaceutically acceptable salt thereof:

US 9,758,529 B2

| | |
|---|---|
| 24 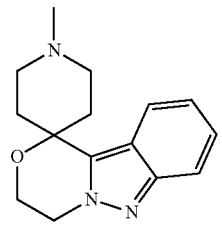 [SMILES: CN1CCC2(CC1)OCCn1nc3ccccc3c12] | 31 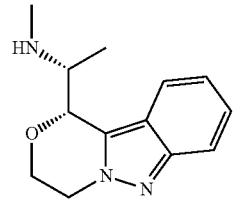 |
| 25 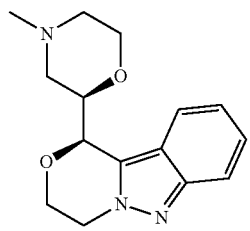 [SMILES: CN1CCO[C@@H]([C@@H]2OCCn3nc4ccccc4c32)C1] | 32 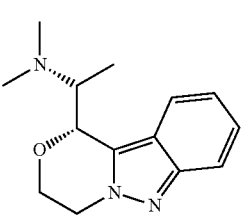 |
| 26 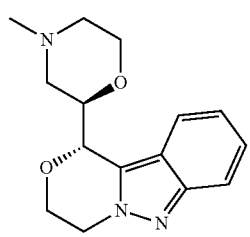 [SMILES: CN1CCO[C@@H]([C@H]2OCCn3nc4ccccc4c32)C1] | 33 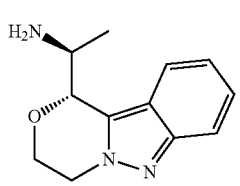 [SMILES: C[C@H](N)[C@H]1OCCn2nc3ccccc3c21] |
| 27 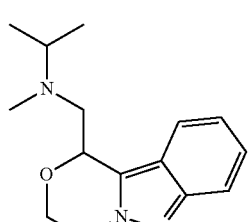 | 34 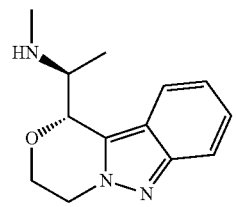 [SMILES: CN[C@@H](C)[C@H]1OCCn2nc3ccccc3c21] |
| 28 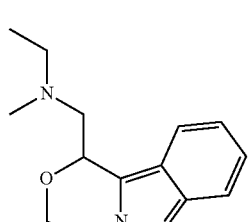 | 35 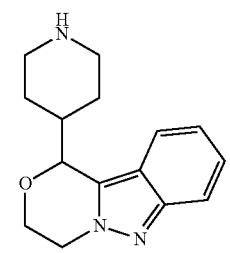 [SMILES: c1ccc2c3n(nc2c1)CCOC3C1CCNCC1] |
| 29 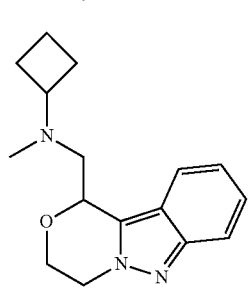 | 36 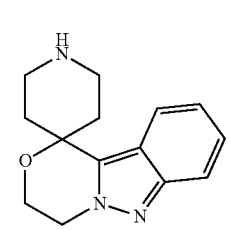 [SMILES: c1ccc2c3n(nc2c1)CCOC31CCNCC1] |
| 30 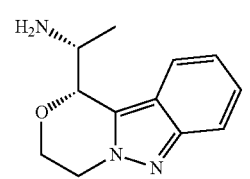 | 37 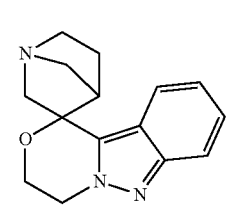 [SMILES: c1ccc2c3n(nc2c1)CCOC31CN2CCC1C2] |

| | |
|---|---|
| 38 | 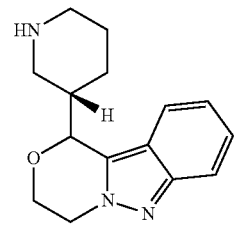 [SMILES: c1ccc2c3n(nc2c1)CCOC3[C@H]1CCCNC1] |
| 39 | 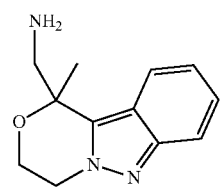 [SMILES: CC1(CN)OCCn2nc3ccccc3c21] |
| 40 | 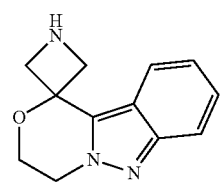 [SMILES: c1ccc2c3n(nc2c1)CCOC31CNC1] |
| 41 | 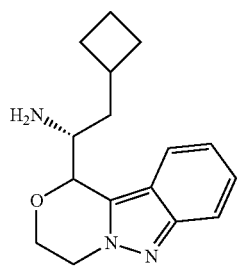 [SMILES: N[C@H](CC1CCC1)C1OCCn2nc3ccccc3c21] |
| 42 | 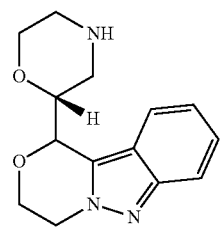 [SMILES: c1ccc2c3n(nc2c1)CCOC3[C@H]1CNCCO1] |
| 43 | 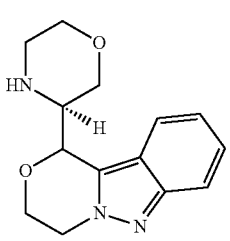 [SMILES: c1ccc2c3n(nc2c1)CCOC3[C@@H]1COCCN1] |
| 44 | 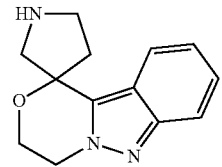 [SMILES: c1ccc2c3n(nc2c1)CCOC31CCNC1] |
| | |
|---|---|
| 45 | 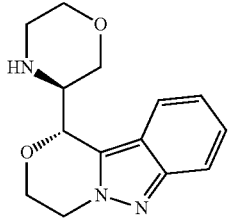 [SMILES: c1ccc2c3n(nc2c1)CCO[C@@H]3[C@@H]1COCCN1] |
| 46 | 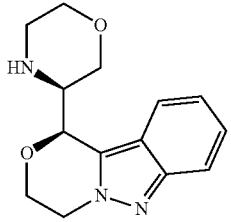 [SMILES: c1ccc2c3n(nc2c1)CCO[C@H]3[C@@H]1COCCN1] |
| 47 | 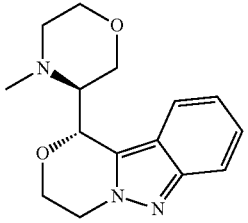 [SMILES: CN1CCOC[C@H]1[C@H]1OCCn2nc3ccccc3c21] |
| 48 | 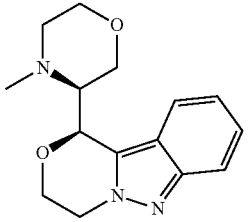 [SMILES: CN1CCOC[C@H]1[C@@H]1OCCn2nc3ccccc3c21] |
| 49 | 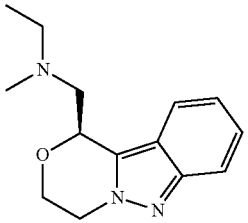 [SMILES: CCN(C)C[C@@H]1OCCn2nc3ccccc3c21] |
| 50 | 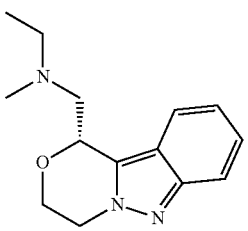 |
| 51 |  |

| 133 -continued | | 134 -continued | |
|---|---|---|---|
| 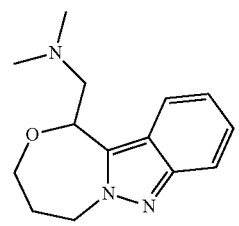 [SMILES: CN(C)CC1OCCCn2nc3ccccc3c21] | 52 | 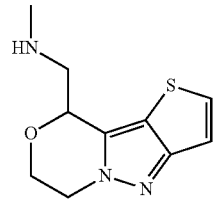 | 58 |
| 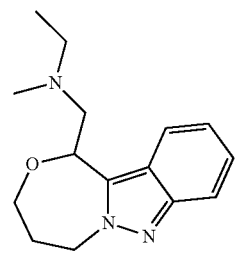 [SMILES: CCN(C)CC1OCCCn2nc3ccccc3c21] | 53 | 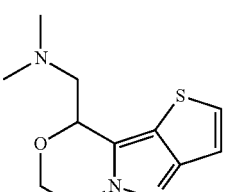 | 59 |
| | | 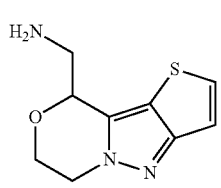 | 60 |
| 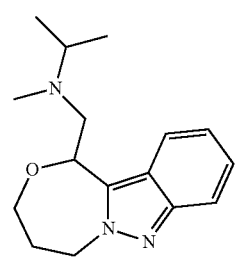 [SMILES: CC(C)N(C)CC1OCCCn2nc3ccccc3c21] | 54 | 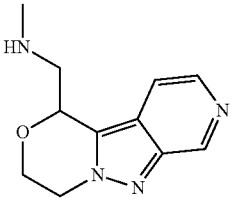 | 61 |
| 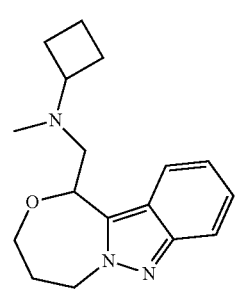 [SMILES: CN(CC1OCCCn2nc3ccccc3c21)C1CCC1] | 55 | 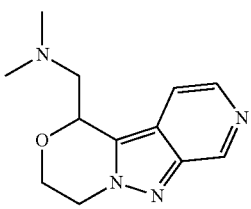 | 62 |
| | | 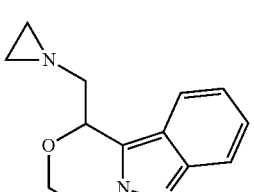 | 63 |
| 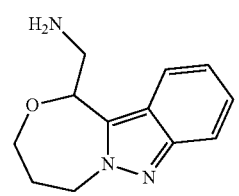 [SMILES: NCC1OCCCn2nc3ccccc3c21] | 56 | 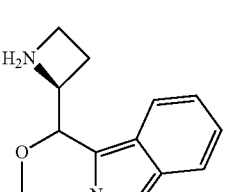 | 64 |
| 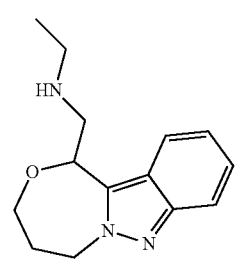 [SMILES: CCNCC1OCCCn2nc3ccccc3c21] | 57 | 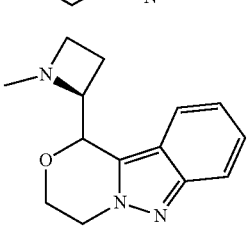 | 65 |

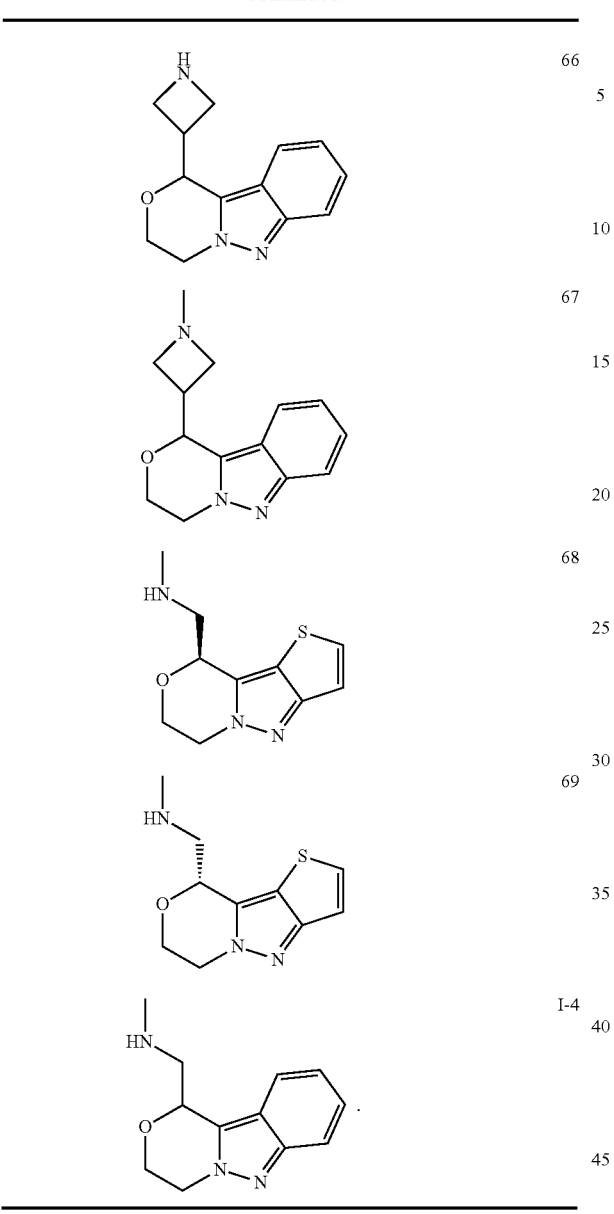

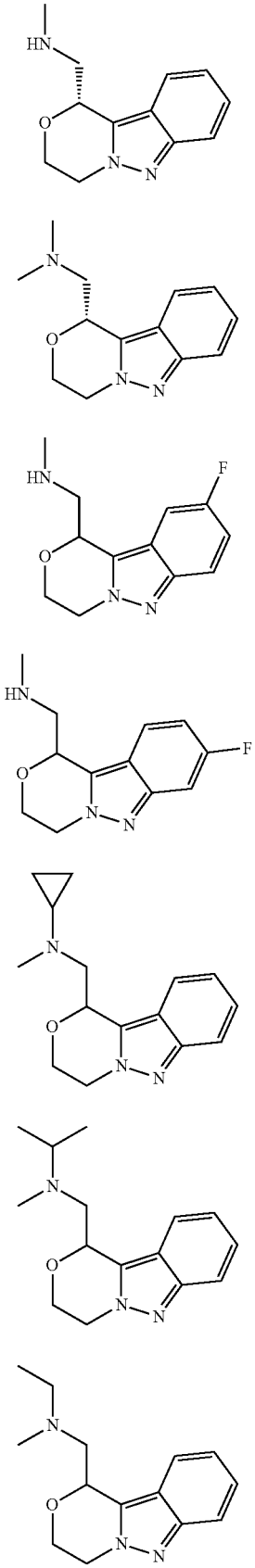

23. A composition comprising the compound of claim 22, or a pharmaceutically acceptable salt thereof, and a pharmaceutically acceptable carrier, adjuvant, or vehicle.

24. A method for treating a neurological or psychiatric disorder in a patient, comprising administering to said patient an effective amount of the compound according to claim 22, or a pharmaceutically acceptable salt thereof, wherein said neurological or psychiatric disorder is selected from depression, anxiety, psychosis, or attention-deficit hyperactivity disorder.

25. The method according to claim 24, wherein the neurological or psychiatric disorder is depression.

26. The method according to claim 25, wherein the depression is treatment-resistant depression (TRD), major depressive disorder (MDD), unipolar depression, bipolar depression or depression associated with another disease or disorder.

27. The compound of claim 22, or a pharmaceutically acceptable salt thereof, selected from:

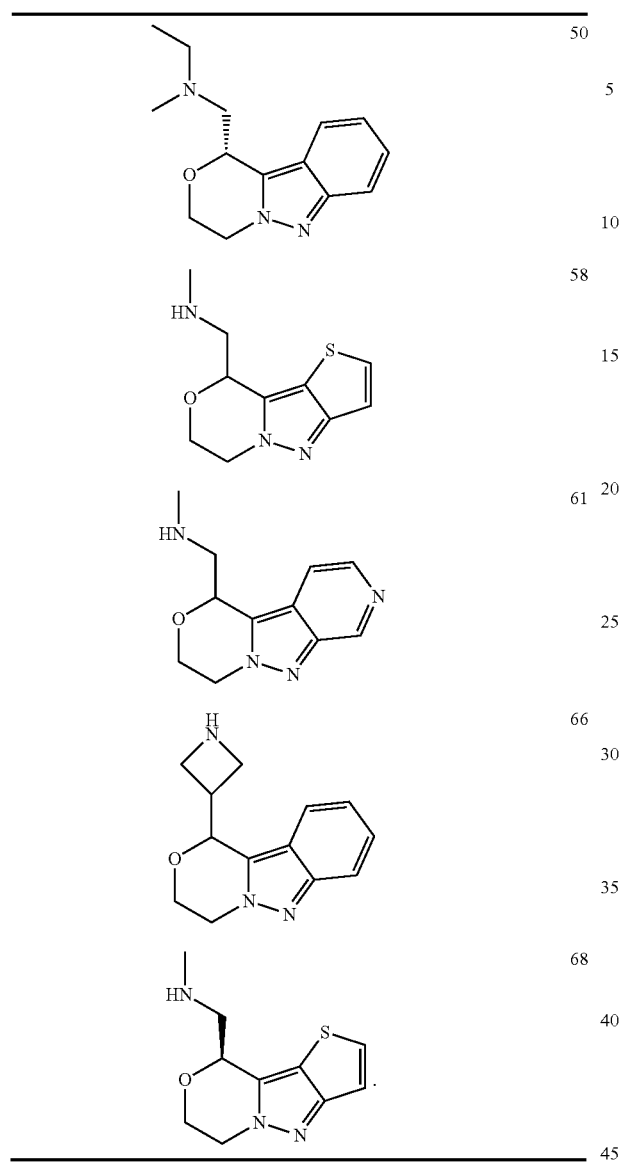
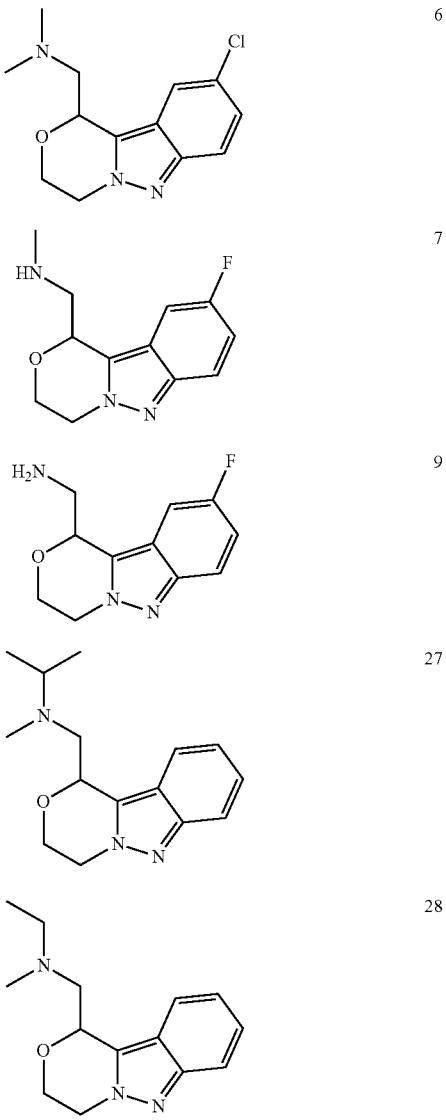
28. The compound of claim 22, or a pharmaceutically acceptable salt thereof, selected from:
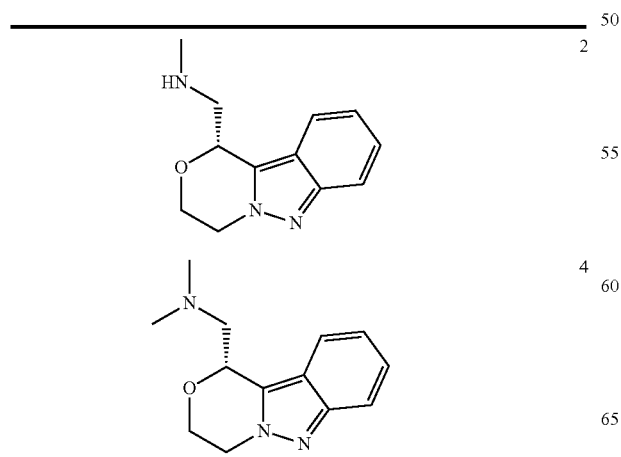
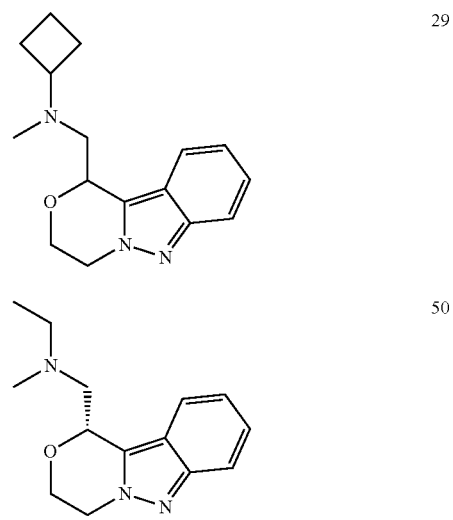

61

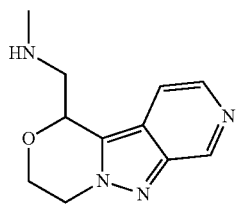 [SMILES: CNCC1OCCn2nc3cnccc3c21]

68

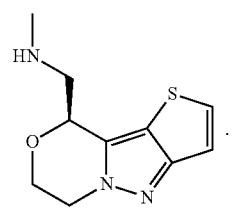

29. The compound of claim 27, or a pharmaceutically acceptable salt thereof, selected from:

2

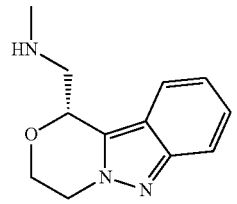 [SMILES: CNC[C@H]1OCCn2nc3ccccc3c21]

4

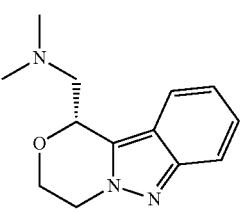 [SMILES: CN(C)C[C@H]1OCCn2nc3ccccc3c21]

7

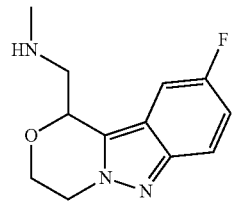 [SMILES: CNCC1OCCn2nc3ccc(F)cc3c21]

27

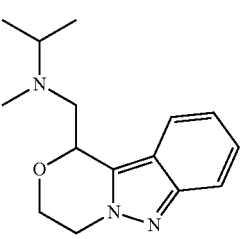 [SMILES: CC(C)N(C)CC1OCCn2nc3ccccc3c21]

28

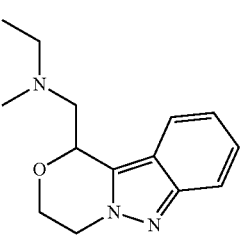 [SMILES: CCN(C)C[C@H]1OCCn2nc3ccccc3c21]

50

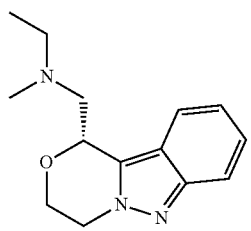

61

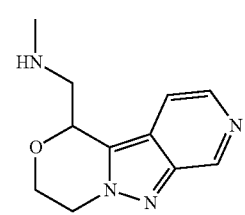

68

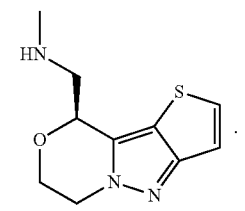

30. The compound of claim 12, or a pharmaceutically acceptable salt thereof, wherein:

$R^7$ is —H;

$R^8$ is —H or —CH$_3$, $R^9$ is —H, C$_1$-C$_3$ alkyl, cyclopropyl or cyclobutyl; and $R^{10}$ is —H or C$_1$-C$_2$ alkyl.

31. The compound of claim 12, or a pharmaceutically acceptable salt thereof, wherein:

n1 is 1;

w is o;

$A^1$ is H;

$R^1$ and $R^4$ are each —H;

$R^2$ and $R^3$ are independently selected from —H, —Cl, or —F, wherein only one of $R^2$ and $R^3$ is not —H;

$R^7$ and $R^8$ are each —H;

$R^9$ is —H or C$_1$-C$_3$ alkyl; and $R^{10}$ is —H or —CH$_3$.

32. The compound of claim 1, wherein the compound is:

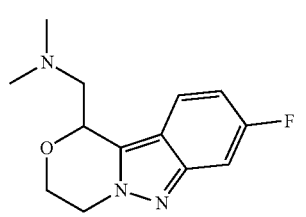

or a pharmaceutically acceptable salt thereof.

33. The compound

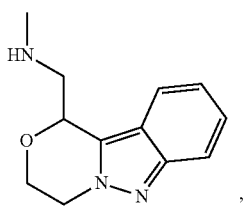

or a pharmaceutically acceptable salt thereof.

34. The compound of claim 22, or a pharmaceutically acceptable salt thereof, selected from:

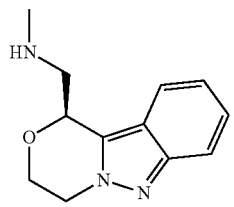 or 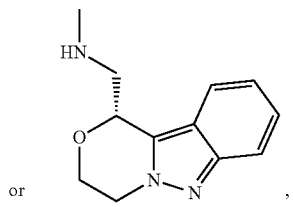

or a mixture thereof.

35. A composition comprising the compound of claim 33, or a pharmaceutically acceptable salt thereof, and a pharmaceutically acceptable carrier, adjuvant, or vehicle.

36. A method for treating a neurological or psychiatric disorder in a patient, comprising administering to said patient an effective amount of the compound according to claim 33, or a pharmaceutically acceptable salt thereof, wherein said neurological or psychiatric disorder is selected from depression, anxiety, psychosis, or attention-deficit hyperactivity disorder.

37. The method according to claim 36, wherein the neurological or psychiatric disorder is depression.

38. The method according to claim 37, wherein the depression is treatment-resistant depression (TRD), major depressive disorder (MDD), unipolar depression, bipolar depression or depression associated with another disease or disorder.

39. The compound

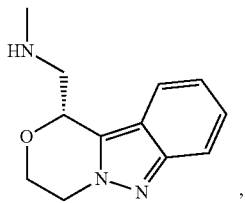

or a pharmaceutically acceptable salt thereof.

40. A composition comprising the compound of claim 39, or a pharmaceutically acceptable salt thereof, and a pharmaceutically acceptable carrier, adjuvant, or vehicle.

41. A method for treating a neurological or psychiatric disorder in a patient, comprising administering to said patient an effective amount of the compound according to claim 39, or a pharmaceutically acceptable salt thereof, wherein said neurological or psychiatric disorder is selected from depression, anxiety, psychosis, or attention-deficit hyperactivity disorder.

42. The method according to claim 41, wherein the neurological or psychiatric disorder is depression.

43. The method according to claim 42, wherein the depression is treatment-resistant depression (TRD), major depressive disorder (MDD), unipolar depression, bipolar depression or depression associated with another disease or disorder.

44. The method according to claim 41, wherein the neurological or psychiatric disorder is anxiety.

45. The method according to claim 41, wherein the neurological or psychiatric disorder is psychosis.

46. The method according to claim 41, wherein the neurological or psychiatric disorder is attention-deficit hyperactivity disorder.

47. A composition according to claim 18, wherein said composition is a pharmaceutically acceptable composition.

48. A composition according to claim 23, wherein said composition is a pharmaceutically acceptable composition.

49. A composition according to claim 35, wherein said composition is a pharmaceutically acceptable composition.

50. A composition according to claim 40, wherein said composition is a pharmaceutically acceptable composition.

51. A method of treating a patient in need of an analgesic or a cognitive enhancer, comprising administering to said patient an effective amount of the compound according to claim 1, or a pharmaceutically acceptable salt thereof.

52. A method of treating a patient in need of an analgesic or a cognitive enhancer, comprising administering to said patient an effective amount of the compound according to claim 22, or a pharmaceutically acceptable salt thereof.

53. A method of treating a patient in need of an analgesic or a cognitive enhancer, comprising administering to said patient an effective amount of the compound according to claim 33, or a pharmaceutically acceptable salt thereof.

54. A method of treating a patient in need of an analgesic or a cognitive enhancer, comprising administering to said patient an effective amount of the compound according to claim 39, or a pharmaceutically acceptable salt thereof.

\* \* \* \* \*

UNITED STATES PATENT AND TRADEMARK OFFICE
CERTIFICATE OF CORRECTION

PATENT NO. : 9,758,529 B2
APPLICATION NO. : 15/041827
DATED : September 12, 2017
INVENTOR(S) : Chytil et al.

It is certified that error appears in the above-identified patent and that said Letters Patent is hereby corrected as shown below:

In the Specification

Column 115, Line 40: Delete "$A^2$ is-$C(R^2)(R^8)$" and insert -- $A^2$ is-$C(R^7)(R^8)$ --

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*